(12) United States Patent
Giordano et al.

(10) Patent No.: US 6,872,850 B2
(45) Date of Patent: Mar. 29, 2005

(54) SMALL MOLECULE INHIBITORS OF SECRETION OF PROTEINS ENCODED BY ARE-MRNAS

(75) Inventors: Tony Giordano, Phoenixville, PA (US); Michael A. Sturgess, Perkasie, PA (US)

(73) Assignee: Message Pharmaceuticals, Malvern, PA (US)

( * ) Notice: Subject to any disclaimer, the term of this patent is extended or adjusted under 35 U.S.C. 154(b) by 0 days.

(21) Appl. No.: 10/117,955

(22) Filed: Apr. 8, 2002

(65) Prior Publication Data

US 2003/0199453 A1 Oct. 23, 2003

Related U.S. Application Data

(60) Provisional application No. 60/282,974, filed on Apr. 10, 2001.

(51) Int. Cl.$^7$ .............................................. C07C 243/12
(52) U.S. Cl. ...................................... 564/147; 564/153
(58) Field of Search .................................. 564/147, 153

(56) References Cited

U.S. PATENT DOCUMENTS

| | | | |
|---|---|---|---|
| 5,892,039 A | | 4/1999 | Shue et al. |
| 5,968,945 A | | 10/1999 | Muller et al. |
| 6,022,900 A | | 2/2000 | Bianchi et al. |
| 6,063,819 A | * | 5/2000 | Marangos et al. .......... 514/634 |

FOREIGN PATENT DOCUMENTS

WO    WO 00/17655    3/2000

OTHER PUBLICATIONS

Bakheet et al., "ARED: Human AU–rich Element–containing mRNA Database Reveals an Unexpectedly Diverse Functional Repertoire of Encoded Proteins," *Nucleic Acids Res.* 2001, 29:246–254.

Cohen et al., "CNI–1493 Inhibits Monocyte/macrophage Tumor Necrosis Factor by Suppression of Translation Efficiency," *Proc. Natl. Acad. Sci. USA.* 1996, 93:3967–3971.

Humphreys et al., "Modes of L929 Cell Death Induced by TNF–alpha and Other Cytotoxic Agents," *Cytokine* 1999, 11:773–782.

Akerlund et al., "Anti–inflammatory Effects of a New Tumour Necrosis Factor–alpha (TNF–alpha) Inhibitor (CNI–1493) in Collagen–induced Arthritis (CIA) in Rats," *Clin. Exp. Immunol.* 1999, 115:32–41.

Molina et al., "CNI–1493 Attenuates Hemodynamic and Pro–inflammatory Responses to LPS," *Shock* 1998, 10:329–334.

\* cited by examiner

*Primary Examiner*—Shailendra Kumar
(74) *Attorney, Agent, or Firm*—Clark & Elbing LLP; Kristina Bieker-Brady, P.C.

(57) ABSTRACT

The invention features compounds that inhibit secretion of a protein encoded by an ARE-mRNA or that modulate regulation of an ARE-mRNA. These compounds are useful for the treatment or prevention of conditions involving proteins encoded by ARE-mRNAs, such as TNFα.

8 Claims, 62 Drawing Sheets

Figure 4

| A LIST OF PREVIOUSLY KNOWN ARE-mRNAs / TRAINING SET ||
|---|---|
| GENE NAME / FUNCTION | GENE NAME / FUNCTION |
| Early lymphocyte activation antigen CD69 | Interleukin-1b (inflammation) |
| 6-phosphofructo-2-kinase (PFK-2)/fructose-2, 6-bisphosphatase | Interleukin-10 (immune response) |
| B-cell leukemia/lymphoma2 oncogene (Bcl-2) | Interleukin-2 (immune response, adaptive) |
| c-fos proto-oncogene (transcription) | Interleukin-3 (hematopoiesis) |
| CHOP/Growth arrest and DNA-damage inducible factor | Interleukin-4 (immune response) |
| c-myb proto-oncogene (transcription) | Interleukin-6 (immune response) |
| c-myc proto-oncogene (transcription) | Interleukin-8 (inflammation) |
| Cyclin D1 (cell cycle) | Interleukin-11 (adipogenesis inhibitory factor) |
| Cyclooxygenase (inflammation) | Lymphotoxin (immune response, inflammation) |
| Endothelin-2 (vascular toning) | K-ras proto-oncogene (signal transduction) |
| Epidermal growth factor receptor | Leukemia inhibitory factor (LIF) |
| Estrogen receptor alpha | Macrophage colony stimulating factor |
| Fibroblast growth factor 2 | Macrophage chemotaxis protein-1 |
| Granulocyte-Colony stimulating factor | Macrophage inflammatory protein-a |
| Glucose Transporter 1 | Macrophage inflammatory protein-b |
| Granulocyte monocyte colony stimulating factor | Macrophage inhibitory protein-2a |
| Gro-a, growth-regulated gene | Mda-7 (melanoma differentiation associated gene) |
| Inducible nitric-oxide synthase | Monocyte Chemotactic Protein-3 |
| Interferon-alpha (immune response, innate) | MYCN (transcription) |
| Intereferon-alphaAA* | Nerve growth factor |
| Interferon-alpha1 | Pim-1 proto-oncogene (singal transduction) |
| Interferon-alpha1B | Plasminogen activator inhibitor type 2 |
| Interferon-alphaF | Platelet derived growth factor/c-sis protooncogene |
| Interferon-alphaG | Thioredexin reductase (metabolism, redox) |
| Interferon-alphaH | Tissue factor (thromboplastin, coagulation) |
| Interferon-b (immune response, innate) | Tumor necrosis factor (inflammation, others) |
| Interferon-g (immune response, adaptive) | Urokinase-type plasminogen (uPA) receptor |
| Interleukin-1a (inflammation) | Urokinase-type plasminogen activator |
| | Vascular endothelial growth factor |

Figure 5

**Group I Cluster
(AUTUAUUUAUUUAUUUAUUUA) stretch:**

| | |
|---|---|
| MMSET type I (MMSET) | AF071594 Cell Growth/Differentiation |
| GDP-L-fucose:beta-D-galactoside 2-alpha-1-Fucosyltransferase | M35531 Metabolism, carbohydrate |
| Cellular growth-regulating protein | L10844 Cell Growth |
| Gro-beta (melanoma stimulating growth factor) | M57731 Cell Growth |
| Pim-1 | M16750 Signal Transduction, oncogenes |
| Neuoron-specific gamma-2 enolase | M22349 Development/Differentiation |
| Nuclear matrix protein NRP/B (NRPB) | AF059611 DNA Transcription/Differentiation |
| Natural killer cell stimulatory factor (IL-12) | M65290 Hematopoiesis, Immune Response |
| Granulocyte-macrophage colony stimulating factor (GM-CSF) | M11220 Hematopoiesis |
| Adipogenesis inhibitory factor (IL-11) | X58377 Hematopoiesis, metabolism |
| Natural resistance-associated macrophage protein | D50402 Immune Response |
| Interleukin 1-beta | M15330 Inflammation |
| Tumor necrosis factor | X01394 Inflammation |

**Group II Cluster
(AUUUAUUUAUUUAUUUA) stretch:**

| | |
|---|---|
| Apoptosis inducing (TRAIL) receptor 2 | AF016849 Apoptosis |
| Death receptor 5 (DR5) | AF012535 Apoptosis |
| K-ras oncogene protein | M54968 Signal Transduction |
| Thioredoxin reductase | S79851 Metabolism, Redox |
| Interleukin-10 receptor | U00672 Immune Regulation, receptors |
| Tyrosine kinase (ELK1) oncogene | M25269 Transcriptional Regulation |
| 6-phosphofructo-2-kinase/fructose 2,6-bisphosphatase (PFKFB) | AF109735 Metabolism, carbohydrate |
| Inducible 6-phosphofructo-2-kinase/fructose 2,6-bisphosphatase (IPFK-2) | AF056320 Metabolism, carbohydrate |
| MOP1, basic-helix-loop-helix-PAS | U29165 Transcriptional Regulation |
| Cytokine-inducible SH2-containing protein (G18) | AF132297 Signal Transduction, inhibitors |
| K-Cl cotransporter KCC4 | AF10536 Nutrient Transport |
| Dishevelled 1 (DVL1) | AF006011 Signal Transduction |
| Guanine nucleotide regulatory factor (LFP40) | U72206 Cellular Motility/biogenesis |
| Zinc finger containing protein ZNF157 (ZNF157) | U28687 DNA Transcription |
| Tubulin-folding cofactor C | U61234 Cellular motility/biogenesis |
| Interferon(LyIFN-alpha-1) | E00102 Immune Response, Innate |
| Alpha-interferon Gx-1 | E00124 Immune Response, Innate |
| Inteferon-alpha | V00542 Immune response, Innate |
| Leukocyte interferon-alpha, clone pIFN105 | M28585 Immune Response, Innate |
| Interferon alpha J | E00052 Immune Response, Innate |
| Messenger RNA for human leukocyte interferon | V00542 Immune Response, Innate |

Figure 5 (cont.)

| | |
|---|---|
| Angiotensin/vasopressin receptor AII/AVP | AF054176 Signal Transduction, receptors |
| c-fos proto-oncogene | V01512 Transcriptional Regulation |

Group III Cluster
(WATUUAUUUAUUUAW) stretch:

| | |
|---|---|
| Interferon (IFN-alpha-M1) | M27318 Immune Response, Innate |
| B-cell leukemia/lymphoma 2 (bcl-2) proto-oncogene | M13994 Apoptosis |
| Condoroitin 6-sulfotransferase | AB017915 Metabolism, sulphate |
| Sodium bicarbonate cotransporter 3 (SLC4A7) | AF047033 Metabolism, Transport |
| Cyclooxygenase-2 (Cox-2) | M90100 Inflammation |
| Neuralized mRNA | AF029729 Development, neural |
| Gro (growth regulated) gene | J03561 Cellular Growth |
| Epiregulin | D30783 Cellular growth |
| A-kinase anchor protein | U17195 Signal Transduction |
| CREB-binding protein | U47741 Transcriptional Regulation |
| L-type amino acid transporter subunit LAT1 | AF104032 Nutrient Transport |
| Zinc-finger DNA-binding motifs (IA-1) | M93119 Transcriptional Regulation |
| Interleukin 3 | M20137 Haematopoiesis |
| E16 | M80244 Signal Transduction, receptors |
| 2-oxoglutarate dehydrogenase | D10523 Metabolism, energy |
| SIRP-beta1 | Y10376 Signal Transduction, inhibitors |
| Putative sulphate transporter (PDS) | AF030880 Nutrient Transport |
| Interleukin 2 (IL2) | U25676 Immune Response, adaptive |
| Post-synaptic density protein 95 (PSD95) | U83192 Neural Regulation |
| Dihydrolipoamide dehydrogenase-binding protein | AF001437 Metabolism, energy |
| Type 2 iodothyronine deiodinase | AF093774 Metabolism, hormones |
| RGP G-protein 3 | U27655 Signal Transduction |
| Alpha endosulfine | AF067170 Nutrient Transport, regulation |
| Tumor necrosis factor alpha inducible A20 zinc finger protein | M59465 Transcriptional Regulation |
| Vascular endothelial growth factor | AF022375 Cellular Growth, angiogenesis |
| Inhibitor of apoptosis protein-1 (MIHC) | AF070674 Apoptosis, regulation |
| A28-RGS14p | U70426 Signal Transduction |
| TNFR2-TRAF signaling complex protein | L49432 Transcriptional Regulation |
| Fibrillin-2 | U03272 Cellular Motility/Biogenesis |
| Farnesylated-proteins converting enzyme 1 | Y13834 Protein modification |
| D-1 dopamine receptor | X58987 Signal Transduction, neural |
| HEB helix-loop-helix protein (HEB) | M80627 Transcriptional Regulation |
| IFN-omega 1 | A12140 Immune Response, innate |
| Interferon beta | X04430 Immune Response, innate |
| Lymphotoxin | E01275 Immune Response |
| Musashi/Nrp-1 | AB012851 Development, neural |
| Thiamine carrier 1 (TC1) | AF153330 Metabolism, nutrient transport |
| Transcription factor (HTF4A) | M83233 Transcription |
| Phospholipase C-beta-2 | M95678 Signal Transduction |
| Onconeural ventral antigen-1 (Nova-1) | U04840 Development/Differentiaion, neural |
| Protein tyrosine kinase mRNA | M59371 Signal Transduction |

Figure 5 (cont.)

| | |
|---|---|
| Tyrosine kinase receptor p145TRK-B (TRK-B) | U12140 Signal Transduction, receptors |
| Protein-tyrosine phosphatase | U27193 Signal Transduction, inhibitors |
| Transcriptional regulatory protein p54 | AF045451 Transcriptional Regulation |
| cAMP phosphodiesterase PDE7 (PDE7A1 | L12052 Signal Transduction |
| Retinoic acid receptor gamma 1 | M38258 Transcriptional Regulation, receptors |
| Tissue factor (thromboplastin) | A19048 Inflammation |
| c-sis/platelet derived growth factor 2 (PDGF2) | AF022375 Cellular growth, oncogenes |
| Endothelial leukocyte adhesion molecule-1 (ELAM-1) | M30640 Inflammation |

Group IV Cluster
(WWWAUUUAUUUAWWW) stretch:
175 sequences available with other group at
http://rc.kfshrc.edu.sa/ared
View Group IV Cluster (text format)

Group V Cluster
(WWWWWAUUUAWWWWW) stretch:
582 sequences available with other group at
http://rc.kfshrc.edu.sa/ared
View Group V Cluster (text format)

Figure 6 Cluster IV ARE-mRNAs

*Homo sapiens* AF-4 mRNA
Accession Number: L13773

*Homo sapiens* EVI5 homolog mRNA
Accession Number: AF008915

*Homo sapiens* mRNA for KIAA0127 gene
Accession Number: D50917

*Homo sapiens* Kallmann syndrome (KAL) mRNA
Accession Number: M97252

*Homo sapiens* mRNA for KIAA0628 protein
Accession Number: AB014528

*Homo sapiens* mRNA for KIAA0936 protein
Accession Number: AB023153

*Homo sapiens* mRNA for KIAA0331 gene
Accession Number: AB002329

*Homo sapiens* mRNA for KIAA0256 gene
Accession Number: D87445

*Homo sapiens* kynurenine 3-hydroxylase mRNA
Accession Number: AF056032

*Homo sapiens* mRNA for prostaglandin E receptor (EP3c)
Accession Number: X83860

*Homo sapiens* mRNA for KIAA0040 gene
Accession Number: D25539

*Homo sapiens* ZFX mRNA for put. transcription activator isoform 2
Accession Number: X59739 X17312

*Homo sapiens* mRNA for KIAA0879 protein
Accession Number: AB020686

*Homo sapiens* CLCA homolog (hCLCA3) mRNA
Accession Number: AF043976

*Homo sapiens* APXL mRNA
Accession Number: X83543

*Homo sapiens* cofilin isoform 2 mRNA
Accession Number: AF134803

*Homo sapiens* cofilin isoform 1 mRNA
Accession Number: AF134802

*Homo sapiens* sodium-hydrogen exchanger 6 (NHE-6) mRNA nuclear gene
    encoding mitochondrial protein
Accession Number: AF030409

*Homo sapiens* glutaminase C mRNA
Accession Number: AF158555

*Homo sapiens* octamer binding transcription factor 1 (OTF1) mRNA
Accession Number: L20433

*Homo sapiens* mRNA for RDC-1 POU domain containing protein
Accession Number: X64624

*Homo sapiens* thrombospondin 2 (THBS2) mRNA
Accession Number: L12350

*Homo sapiens* intersectin long form mRNA
Accession Number: AF064244

*Homo sapiens* hypothetical SBBI03 protein mRNA
Accession Number: AF077599

*Homo sapiens* putative tumor suppressor ST13 (ST13) mRNA
Accession Number: U17714

*Homo sapiens* mRNA for novel gene in Xq28 region
Accession Number: X92396

*Homo sapiens* mRNA for KIAA0835 protein
Accession Number: AB020642

*Homo sapiens* endothelial cell thrombomodulin mRNA
Accession Number: M16552

*Homo sapiens* paired box protein mRNA
Accession Number: L25597

*Homo sapiens* fragile X mental retardation protein FMR2p (FMR2) mRNA
Accession Number: U48436

*Homo sapiens* galactocerebrosidase (GALC) mRNA
Accession Number: L23116

*Homo sapiens* paired-box protein (PAX2) mRNA
Accession Number: M89470

*Homo sapiens* mRNA for KIAA0990 protein
Accession Number: AB023207

*Homo sapiens* mRNA for c-sis gene (clone pSM-1)
Accession Number: X02744

*Homo sapiens* nucleotide binding protein mRNA
Accession Number: L04510

*Homo sapiens* mRNA for HE6 Tm7 receptor
Accession Number: X81892

*Homo sapiens* mRNA for carcinoembryonic antigen family member 2 CGM2
Accession Number: X98311

*Homo sapiens* heparin-binding EGF-like growth factor mRNA
Accession Number: M60278

*Homo sapiens* 150 kDa oxygen-regulated protein ORP150 mRNA
Accession Number: U65785

*Homo sapiens* mRNA for KIAA0688 protein
Accession Number: AB014588

*Homo sapiens* SCA1 mRNA for ataxin
Accession Number: X79204

*Homo sapiens* mRNA for phospholipase C
Accession Number: D42108

*Homo sapiens* N-methyl-D-aspartate receptor subunit NR3 (hNR3) mRNA
Accession Number: U11287

*Homo sapiens* mRNA for 46 kDa coxsackievirus and adenovirus receptor (CAR) protein
Accession Number: Y07593

*Homo sapiens* aggrecanase-1 mRNA
Accession Number: AF148213

*Homo sapiens* monocyte-derived neutrophil-activating protein (MONAP) mRNA
Accession Number: M26383

*Homo sapiens* mRNA for leukemia associated gene 2
Accession Number: Y15228

*Homo sapiens* CGI-111 protein mRNA
Accession Number: AF151869

*Homo sapiens* Hus1-like protein (HUS1) mRNA
Accession Number: AF076844

*Homo sapiens* Ste20-like kinase (MST2) mRNA
Accession Number: U26424

*Homo sapiens* hairy and enhancer of split related-1 (HESR-1) mRNA
Accession Number: AF151522

*Homo sapiens* mRNA for MDNCF (monocyte-derived neutrophil chemotactic factor)
Accession Number: Y00787

*Homo sapiens* epidermal growth factor receptor kinase substrate (Eps8) mRNA
Accession Number: U12535

*Homo sapiens* mRNA for UDP-galactose translocator
Accession Number: D84454

*Homo sapiens* butyrophilin (BTF1) mRNA
Accession Number: U90543

*Homo sapiens* basic fibroblast growth factor (bFGF) 22.5 kd 21 kd and 18 kd protein mRNA
Accession Number: J04513

*Homo sapiens* interleukin 10 (IL10) mRNA
Accession Number: M57627

*Homo sapiens* mRNA for tre oncogene (clone 213)
Accession Number: X63547

*Homo sapiens* (AF1q) mRNA
Accession Number: U16954

*Homo sapiens* mRNA for KIAA0471 protein
Accession Number: AB007940

*Homo sapiens* WD repeat protein WDR3 (WDR3) mRNA
Accession Number: AF083217

*Homo sapiens* mRNA for KIAA0258 gene
Accession Number: D87447

*Homo sapiens* TACC1 (TACC1) mRNA
Accession Number: AF049910

*Homo sapiens* yotiao mRNA
Accession Number: AF026245

*Homo sapiens* unknown protein (BT2.1) mRNA
Accession Number: U90142

*Homo sapiens* decay-accelerating factor mRNA
Accession Number: M31516

*Homo sapiens* KIAA0410 mRNA
Accession Number: AB007870

*Homo sapiens* ZFX mRNA for put. transcription activator isoform 3
Accession Number: X59740 X17312

*Homo sapiens* mRNA for nebulette
Accession Number: Y16241

*Homo sapiens* mRNA for protein kinase PKX1
Accession Number: X85545
*Homo sapiens* C-1 mRNA
Accession Number: U41816

*Homo sapiens* N-methyl-D-aspartate receptor 2B subunit precursor mRNA
Accession Number: U90278

*Homo sapiens* calcineurin A1 mRNA
Accession Number: M29550

*Homo sapiens* mRNA for KIAA0277 gene
Accession Number: D87467

*Homo sapiens* mRNA for KIAA0617 protein
Accession Number: AB014517

*Homo sapiens* mRNA for KIAA0941 protein
Accession Number: AB023158

*Homo sapiens* mRNA for B-HLH DNA binding protein
Accession Number: X99268

*Homo sapiens* putative Cu++-transporting P-type ATPase mRNA
Accession Number: L06133

*Homo sapiens* mRNA for tre oncogene (clone 210)
Accession Number: X63546

*Homo sapiens* estrogen-related receptor gamma mRNA
Accession Number: AF058291

*Homo sapiens* mRNA for KIAA0531 protein
Accession Number: AB011103

*Homo sapiens* mRNA for KIAA0832 protein
Accession Number: AB020639

*Homo sapiens* mRNA for transforming growth factor alpha
Accession Number: X70340

*Homo sapiens* mRNA for glia maturation factor
Accession Number: AB001106

*Homo sapiens* mRNA for HYA22
Accession Number: D88153

*Homo sapiens* CGI-145 protein mRNA
Accession Number: AF151903

*Homo sapiens* LIM protein (LPP) mRNA
Accession Number: U49957

*Homo sapiens* CGI-34 protein mRNA
Accession Number: AF132968

*Homo sapiens* KIAA0426 mRNA
Accession Number: AB007886

*Homo sapiens* EXLM1 mRNA
Accession Number: AB006651

*Homo sapiens* putative opioid receptor mRNA
Accession Number: M84605 cDNA encoding human interferon
Accession Number: E00294 cDNA encoding human lymphotoxin polypeptide
Accession Number: E01275

*Homo sapiens* mRNA for lymphotoxin
Accession Number: X01393

*Homo sapiens* forkhead protein (FKHR) mRNA
Accession Number: AF032885 trkB [human brain mRNA 3194 nt]
Accession Number: S76473

*Homo sapiens* mRNA for KIAA0924 protein
Accession Number: AB023141

*Homo sapiens* common acute lymphoblastic leukemia antigen (CALLA) mRNA
Accession Number: J03779

*Homo sapiens* PRAD1 mRNA for cyclin
Accession Number: X59798 X59485

*Homo sapiens* X2 box repressor mRNA
Accession Number: U22680

*Homo sapiens* mRNA for leukaemia inhibitory factor (LIF/HILDA)
Accession Number: X13967

*Homo sapiens* mRNA for KIAA0316 gene
Accession Number: AB002314

*Homo sapiens* clone CIITA-8 MHC class II transactivator CIITA mRNA
Accession Number: U18259

*Homo sapiens* substance P beta-PPT-A mRNA
Accession Number: U37529

*Homo sapiens* mRNA for 1D-myo-inositol-trisphosphate 3-kinase B isoenzyme
Accession Number: X57206

*Homo sapiens* mRNA for KIAA0952 protein
Accession Number: AB023169

*Homo sapiens* stanniocalcin precursor (STC) mRNA
Accession Number: U25997

*Homo sapiens* WSB-1 isoform mRNA
Accession Number: AF106684

*Homo sapiens* WSB-1 mRNA
Accession Number: AF106683

*Homo sapiens* WSB-1 mRNA
Accession Number: AF069313

*Homo sapiens* mRNA for mannose-binding protein C
Accession Number: X15422

*Homo sapiens* mRNA for KIAA0271 gene
Accession Number: D87461

*Homo sapiens* tumor necrosis factor-inducible (TSG-6) mRNA fragment adhesion receptor CD44 putative CDS
Accession Number: M31165

*Homo sapiens* tropomyosin isoform mRNA
Accession Number: Z24727

*Homo sapiens* mRNA for KIAA0562 protein
Accession Number: AB011134 cDNA encoding endothelin receptorETB-receptor
Accession Number: E07650

*Homo sapiens* mRNA for KIAA0458 protein
Accession Number: AB007927

*Homo sapiens* tropomyosin mRNA
Accession Number: M19267

*Homo sapiens* mRNA for KIAA0565 protein
Accession Number: AB011137

*Homo sapiens* 19.8 kDa protein mRNA
Accession Number: U18914

*Homo sapiens* mRNA for KIAA1101 protein
Accession Number: AB029024

*Homo sapiens* mRNA for oxidative-stress responsive 1
Accession Number: AB017642

*Homo sapiens* mRNA for hRTR/hGCNF protein
Accession Number: X99975

*Homo sapiens* cellular proto-oncogene (c-mer) mRNA
Accession Number: U08023

*Homo sapiens* proto-oncogene (Wnt-5a) mRNA
Accession Number: L20861

*Homo sapiens* cell adhesion protein (vitronectin) receptor alpha subunit mRNA
Accession Number: M14648 J02826 M18365

*Homo sapiens* mRNA for KIAA0285 gene
Accession Number: AB006623

*Homo sapiens* UDP-Gal:glucosylceramide beta-14-galactosyltransferase mRNA
Accession Number: AF097159

*Homo sapiens* dead box X isoform (DBX) mRNA alternative transcript 2
Accession Number: AF000982

*Homo sapiens* cyclin T2a mRNA
Accession Number: AF048731

*Homo sapiens* mRNA capping enzyme (HCE) mRNA
Accession Number: AF025654

*Homo sapiens* insulin receptor substrate-2 (IRS2) mRNA
Accession Number: AF073310

*Homo sapiens* natural killer cell stimulatory factor (NKSF) mRNA
Accession Number: M65291

DNA coding of LeIF B
Accession Number: E00044

*Homo sapiens* glycogen debranching enzyme isoform 4 (AGL) mRNA
alternatively spliced isoform
Accession Number: U84010

*Homo sapiens* glycogen debranching enzyme isoform 3 (AGL) mRNA
alternatively spliced isoform
Accession Number: U84009

*Homo sapiens* glycogen debranching enzyme isoform 6 (AGL) mRNA
alternatively spliced isoform
Accession Number: U84011

*Homo sapiens* glycogen debranching enzyme isoform 1 (AGL) mRNA
alternatively spliced isoform
Accession Number: U84007

*Homo sapiens* glycogen debranching enzyme isoform 2 (AGL) mRNA
alternatively spliced isoform
Accession Number: U84008

*Homo sapiens* bright and dead ringer gene product homologous protein Bdp mRNA
Accession Number: AF116846

*Homo sapiens* glycogen debranching enzyme mRNA
Accession Number: M85168

*Homo sapiens* dead box Y isoform (DBY) mRNA alternative transcript 2
Accession Number: AF000984

*Homo sapiens* mRNA for semaphorin E
Accession Number: AB000220

DNA coding of LeIF I
Accession Number: E00051

*Homo sapiens* mRNA for KIAA0798 protein
Accession Number: AB018341

*Homo sapiens* hVps41p (HVPS41) mRNA
Accession Number: U87309

*Homo sapiens* (clone pAT 464) potential lymphokine/cytokine mRNA
Accession Number: M25315

*Homo sapiens* mRNA for KIAA0705 protein
Accession Number: AB014605

*Homo sapiens* protein translation factor sui1 homolog mRNA
Accession Number: AF077052

*Homo sapiens* brain my047 protein mRNA
Accession Number: AF063605

*Homo sapiens* mRNA for KIAA0480 protein
Accession Number: AB007949

*Homo sapiens* mRNA (clone p5) for archain
Accession Number: X81198

*Homo sapiens* mRNA for KIAA0970 protein
Accession Number: AB023187

*Homo sapiens* glucose transporter-like protein-III (GLUT3)
Accession Number: M20681

*Homo sapiens* GC20 protein mRNA
Accession Number: AF064607

*Homo sapiens* proto-oncogene Wnt7a mRNA
Accession Number: U53476

*Homo sapiens* mRNA for LAK-1
Accession Number: AB005754

*Homo sapiens* mRNA for 26S proteasome subunit p55
Accession Number: AB003103

*Homo sapiens* KIAA0419 mRNA
Accession Number: AB007879

*Homo sapiens* mRNA for TL132
Accession Number: AJ012755

*Homo sapiens* neuropeptide y2 receptor mRNA
Accession Number: U42766

*Homo sapiens* mRNA for thrombospondin
Accession number: X14787

*Homo sapiens* mRNA; cDNA DKFZp564M112 (from clone DKFZp564M112)
Accession Number: AL080070

*Homo sapiens* autosomal dominant polycystic kidney disease type II (PKD2) mRNA
Accession number: U50928

*Homo sapiens* mRNA for glutamate transporter
Accession number: D26443

*Homo sapiens* homeobox-containing protein mRNA
Accession number: U68727

*Homo sapiens* SOX9 mRNA
Accession number: Z46629

*Homo sapiens* mRNA for KIAA0313 gene
Accession number: AB002311

*Homo sapiens* type 2 neuropeptide Y receptor mRNA
Accession number: U32500

DNA coding of interferon(LyIFN-alpha-2)
Accession number: E00104

*Homo sapiens* mRNA for T-cell replacing factor (interleukin-5)
Accession number: X04688

*Homo sapiens* WNT7a mRNA
Accession number: D83175

*Homo sapiens* interferon-alpha type I' mRNA
Accession number: M11026

*Homo sapiens* mRNA for hSLK
Accession number: AB002804

*Homo sapiens* synaptotagmin mRNA
Accession number: M55047 J05710

Figure 7 Cluster V ARE-mRNAs

*Homo sapiens* uPA cDNA
Accession Number: A18397 u-PA receptor
Accession Number: A18757

*Homo sapiens* BTA 1916 mRNA for Pai-2
Accession Number: A21239

*Homo sapiens* BTA 1922 mRNA for Pai-2
Accession Number: A21240

*Homo sapiens* NPY receptor Y1 gene cDNA
Accession Number: A26481

*Homo sapiens* beta-casein cDNA
Accession Number: A30262

*Homo sapiens* u-PA cDNA sequence
Accession Number: A35395

*Homo sapiens* mRNA for TRAF5
Accession Number: AB000509

*Homo sapiens* mRNA for Efs1
Accession Number: AB001466

*Homo sapiens* mRNA for Efs2
Accession Number: AB001467

*Homo sapiens* mRNA for KIAA0294 gene
Accession Number: AB002292

*Homo sapiens* mRNA for KIAA0305 gene
Accession Number: AB002303

*Homo sapiens* mRNA for KIAA0373 gene
Accession Number: AB002371

*Homo sapiens* mRNA for KIAA0377 gene
Accession Number: AB002375

*Homo sapiens* mRNA for Cdc7-related kinase
Accession Number: AB003698

*Homo sapiens* mRNA for KIAA0288 gene
Accession Number: AB006626

*Homo sapiens* mRNA for chemokine LEC precursor
Accession Number: AB007454

*Homo sapiens* KIAA0400 mRNA
Accession Number: AB007860

*Homo sapiens* KIAA0406 mRNA
Accession Number: AB007866

*Homo sapiens* KIAA0414 mRNA partial cds
Accession Number: AB007874

*Homo sapiens* mRNA for KIAA0476 protein
Accession Number: AB007945

*Homo sapiens* FCMD mRNA for fukutin
Accession Number: AB008226

*Homo sapiens* mRNA for KIAA0550 protein
Accession Number: AB011122

*Homo sapiens* mRNA for KIAA0571 protein
Accession Number: AB011143

*Homo sapiens* mRNA for DRAK1
Accession Number: AB011420

*Homo sapiens* mRNA for KIAA0652 protein
Accession Number: AB014552

*Homo sapiens* mRNA for KIAA0660 protein
Accession Number: AB014560

*Homo sapiens* mRNA for KIAA0669 protein
Accession Number: AB014569

*Homo sapiens* mRNA for KIAA0685 protein
Accession Number: AB014585

*Homo sapiens* mRNA for sterol-C5-desaturase
Accession Number: AB016247

*Homo sapiens* HGC6.1.1 mRNA
Accession Number: AB016899

*Homo sapiens* mRNA for KIAA0711 protein
Accession Number: AB018254

*Homo sapiens* mRNA for KIAA0716 protein
Accession Number: AB018259

*Homo sapiens* mRNA for KIAA0736 protein
Accession Number: AB018279

*Homo sapiens* mRNA for KIAA0744 protein
Accession Number: AB018287

*Homo sapiens* mRNA for Gab2
Accession Number: AB018413

*Homo sapiens* PKIG mRNA for protein kinase inhibitor gamma
Accession Number: AB019517

*Homo sapiens* mRNA for dermatan/chondroitin sulfate
    2-sulfotransferase
Accession Number: AB020316

*Homo sapiens* mRNA for KIAA0848 protein
Accession Number: AB020655

*Homo sapiens* mRNA for KIAA0852 protein
Accession Number: AB020659

*Homo sapiens* HFB30 mRNA
Accession Number: AB022663

*Homo sapiens* FUT9 mRNA for alpha-13-fucosyltransferase IX
Accession Number: AB023021

*Homo sapiens* mRNA for KIAA0938 protein
Accession Number: AB023155

*Homo sapiens* mRNA for KIAA0966 protein
Accession Number: AB023183

*Homo sapiens* mRNA for KIAA0971 protein
Accession Number: AB023188

*Homo sapiens* mRNA for KIAA1008 protein
Accession Number: AB023225

*Homo sapiens* mRNA for MALT1
Accession Number: AB026118

*Homo sapiens* mRNA for Kelch motif containing protein
Accession Number: AB026190

*Homo sapiens* mRNA for KIAA1041 protein
Accession Number: AB028964

*Homo sapiens* mRNA for epsilon-adaptin
Accession Number: AB030653

*Homo sapiens* germinal center kinase related protein kinase mRNA
Accession Number: AF000145

*Homo sapiens* cdc14 homolog mRNA
Accession Number: AF000367

*Homo sapiens* ubiquitous TPR motif X isoform (UTX) mRNA
    alternative transcript 2
Accession Number: AF000993

*Homo sapiens* RNA editase (RED1) mRNA
Accession Number: AF001042

*Homo sapiens* lymphoid phosphatase LyP1 mRNA
Accession Number: AF001846

*Homo sapiens* E1B 19K/Bcl-2-binding protein Nip3 mRNA nuclear gene
    encoding mitochondrial protein
Accession Number: AF002697

*Homo sapiens* Jagged1 (JAG1) mRNA
Accession Number: AF003837

*Homo sapiens* germ cell nuclear factor (GCNF) mRNA
Accession Number: AF004291

*Homo sapiens* hUNC18a alternatively-spliced mRNA
Accession Number: AF004562

*Homo sapiens* hUNC18b alternatively-spliced mRNA
Accession Number: AF004563

*Homo sapiens* jerky gene product homolog mRNA
Accession Number: AF004715

*Homo sapiens* CDO mRNA
Accession Number: AF004841

*Homo sapiens* retinoic acid hydroxylase mRNA
Accession Number: AF005418

*Homo sapiens* CHD2 mRNA
Accession Number: AF006514

*Homo sapiens* embryonic lung protein (HUEL) mRNA
Accession Number: AF006621

*Homo sapiens* MDM2-like p53-binding protein (MDMX) mRNA
Accession Number: AF007111

*Homo sapiens* TEB4 protein mRNA
Accession Number: AF009301

*Homo sapiens* homeodomain protein (BAPX1) mRNA
Accession Number: AF009801

*Homo sapiens* eIF4GII mRNA
Accession Number: AF012072

*Homo sapiens* zinc finger protein (ZNF198) mRNA
Accession Number: AF012126

*Homo sapiens* MTG8-like protein MTGR1b mRNA
Accession Number: AF013970

*Homo sapiens* Cdc7 (CDC7) mRNA
Accession Number: AF015592

*Homo sapiens* chromosome 1 atrophin-1 related protein (DRPLA) mRNA
Accession Number: AF016005 AF001845

*Homo sapiens* maltase-glucoamylase mRNA
Accession Number: AF016833

*Homo sapiens* receptor activator of nuclear factor kappa B ligand
    (RANKL) mRNA
Accession Number: AF019047

*Homo sapiens* heparan sulfate 3-O-sulfotransferase-1 precursor
    (3OST1) mRNA
Accession Number: AF019386

*Homo sapiens* macrophage inhibitory cytokine-1 (MIC-1) mRNA
Accession Number: AF019770

*Homo sapiens* DNA damage-inducible RNA binding protein (A18hnRNP)
    mRNA
Accession Number: AF021336

*Homo sapiens* homeodomain protein (OG12) mRNA
Accession Number: AF022654

*Homo sapiens* protein phosphatase with EF-hands-2 long form (PPEF-2)
    mRNA
Accession Number: AF023456

*Homo sapiens* serine/threonine kinase RICK (RICK) mRNA
Accession Number: AF027706

*Homo sapiens* transmembrane protein Jagged 1 (HJ1) mRNA
Accession Number: AF028593

*Homo sapiens* glypican-4 (GPC4) mRNA
Accession Number: AF030186

*Homo sapiens* epithelial V-like antigen precursor (EVA) mRNA
Accession Number: AF030455

*Homo sapiens* acyl-CoA synthetase 4 (ACS4) mRNA
Accession Number: AF030555

*Homo sapiens* interleukin 15 precursor (IL-15) mRNA
Accession Number: AF031167

*Homo sapiens* cell cycle related kinase mRNA
Accession Number: AF035013

*Homo sapiens* FGFR signalling adaptor SNT-2 mRNA
Accession Number: AF036718

*Homo sapiens* pre-mRNA splicing factor (PRP17) mRNA
Accession Number: AF038392

*Homo sapiens* atrophin-1 interacting protein 1 (AIP1) mRNA
Accession Number: AF038563

*Homo sapiens* anti-death protein (IEX-1L) mRNA
Accession Number: AF039067

*Homo sapiens* cadherin-10 (CDH10) mRNA
Accession Number: AF039747

*Homo sapiens* TATA binding protein associated factor (TAFII150) mRNA
Accession Number: AF040701

*Homo sapiens* spindle pole body protein spc98 homolog GCP3 mRNA
Accession Number: AF042378

*Homo sapiens* lithium-sensitive myo-inositol monophosphatase A1 (IMPA1) mRNA Accession Number: AF042729

*Homo sapiens* HCG-1 protein (HCG-1) mRNA
Accession Number: AF044221

*Homo sapiens* protein regulating cytokinesis 1 (PRC1) mRNA
Accession Number: AF044588

*Homo sapiens* cytokine receptor related protein 4 (CYTOR4) mRNA

Accession Number: AF046059

*Homo sapiens* ribosomal protein L33-like protein mRNA
Accession Number: AF047440

*Homo sapiens* spleen mitotic checkpoint BUB3 (BUB3) mRNA
Accession Number: AF047472

*Homo sapiens* MMS2 (MMS2) mRNA
Accession Number: AF049140

*Homo sapiens* Src-associated adaptor protein (SAPS) mRNA
Accession Number: AF051323

*Homo sapiens* supervillin mRNA
Accession Number: AF051850

*Homo sapiens* 15 kDa selenoprotein mRNA
Accession Number: AF051894

*Homo sapiens* neuronal double zinc finger protein (ZNF231) mRNA
Accession Number: AF052224

*Homo sapiens* mitotic checkpoint component Bub3 (BUB3) mRNA
Accession Number: AF053304

*Homo sapiens* osteoprotegerin ligand mRNA
Accession Number: AF053712

*Homo sapiens* clone 24695 guanine nucleotide-binding protein alpha-i subunit (GNAZ) mRNA
Accession Number: AF055013

*Homo sapiens* monotactin-1 mRNA
Accession Number: AF055467 1

*Homo sapiens* leucine-rich glioma-inactivated protein precursor (LGI1) mRNA
Accession Number: AF055636

*Homo sapiens* sarcosin mRNA
Accession Number: AF056929

*Homo sapiens* actin binding protein MAYVEN mRNA

Accession Number: AF059569

*Homo sapiens* serum-inducible kinase mRNA
Accession Number: AF059617

*Homo sapiens* Gz-selective GTPase-activating protein (ZGAP1) mRNA
Accession Number: AF060877

*Homo sapiens* UDP-glucose dehydrogenase (UGDH) mRNA
Accession Number: AF061016

*Homo sapiens* protocadherin (PCDH8) mRNA
Accession Number: AF061573

*Homo sapiens* diacylglycerol kinase iota (DGKi) mRNA
Accession Number: AF061936

*Homo sapiens* keratan sulfate proteoglycan mRNA
Accession Number: AF063301

*Homo sapiens* low-density lipoprotein receptor-related protein 5 (LRP5) mRNA
Accession Number: AF064548

*Homo sapiens* haemopoietic progenitor homeobox HPX42B (HPX42B) mRNA
Accession Number: AF068006

*Homo sapiens* choline/ethanolaminephosphotransferase (CEPT1) mRNA
Accession Number: AF068302

*Homo sapiens* cytohesin binding protein HE mRNA
Accession Number: AF068836

*Homo sapiens* MTG8-like protein MTGR1a mRNA
Accession Number: AF069747

*Homo sapiens* OPA-containing protein mRNA
Accession Number: AF071309

*Homo sapiens* small EDRK-rich factor 1 short isoform (SERF1) mRNA
Accession Number: AF073518

*Homo sapiens* cytokine-inducible SH2 protein 6 (CISH6) mRNA
Accession Number: AF073958

*Homo sapiens* HSPC012 mRNA
Accession Number: AF077036

*Homo sapiens* SIH002 mRNA
Accession Number: AF077041

*Homo sapiens* HSPC019 mRNA
Accession Number: AF077205

*Homo sapiens* LDL receptor member LR3 mRNA
Accession Number: AF077820

*Homo sapiens* conductin mRNA
Accession Number: AF078165

*Homo sapiens* ubiquitin-like protein activating enzyme (UBA2) mRNA
Accession Number: AF079566

*Homo sapiens* testis-specific chromodomain Y-like protein (CDYL) mRNA
alternatively processed
Accession Number: AF081259

*Homo sapiens* sirtuin type 1 (SIRT1) mRNA
Accession Number: AF083106

*Homo sapiens* cyclin-D binding Myb-like protein mRNA
Accession Number: AF084530

*Homo sapiens* xenotropic and polytropic murine leukemia virus receptor (X3) mRNA
Accession Number: AF0897

*Homo sapiens* SUMO-1-activating enzyme E1 C subunit (UBA2) mRNA
Accession Number: AF090384

*Homo sapiens* clone 628 unknown mRNA complete sequence
Accession Number: AF091083

*Homo sapiens* beta-13-N-acetylglucosaminyltransferase mRNA
Accession Number: AF092051

*Homo sapiens* Ste-20 related kinase SPAK mRNA

Accession Number: AF099989

*Homo sapiens* ARF-family of Ras related GTPases mRNA
Accession Number: AF100740

*Homo sapiens* connective tissue growth factor related protein WISP-1 (WISP1) mRNA  Accession Number: AF100779

*Homo sapiens* bone morphogenetic protein 10 (BMP10) mRNA
Accession Number: AF101441

*Homo sapiens* placenta-specific ATP-binding cassette transporter (ABCP) mRNA
Accession Number: AF103796

*Homo sapiens* decoy receptor 3 (DcR3) mRNA
Accession Number: AF104419

*Homo sapiens* heparan sulfate D-glucosaminyl 3-O-sulfotransferase-3B (3OST3B1) mRNA
Accession Number: AF105377

*Homo sapiens* mitochondrial inner membrane preprotein translocase Tim17a mRNA nuclear gene encoding mitochondrial protein
Accession Number: AF106622

*Homo sapiens* stromal cell-derived receptor-1 beta mRNA
Accession Number: AF109126

*Homo sapiens* Mcd4p homolog mRNA
Accession Number: AF109219

*Homo sapiens* eukaryotic translation initiation factor 2 alpha kinase PEK mRNA
Accession Number: AF110146

*Homo sapiens* fibroblast growth factor 19 (FGF19) mRNA
Accession Number: AF110400

*Homo sapiens* TDE homolog mRNA
Accession Number: AF112227

*Homo sapiens* integral inner nuclear membrane protein MAN1 mRNA
Accession Number: AF112299

*Homo sapiens* clone HH114 unknown mRNA
Accession Number: AF114263

*Homo sapiens* host cell factor 2 (HCF-2) mRNA
Accession Number: AF117210

*Homo sapiens* thyroid hormone receptor-associated protein complex component TRAP240 mRNA
Accession Number: AF117754

*Homo sapiens* cytokine receptor-like molecule 9 (CREME9) mRNA
Accession Number: AF120151

*Homo sapiens* CAAX prenyl protein protease RCE1 (RCE1) mRNA
Accession Number: AF121951

*Homo sapiens* API2-MLT fusion protein (API2-MLT) mRNA
Accession Number: AF123094

*Homo sapiens* SH2-containing protein Nsp2 mRNA
Accession Number: AF124250

*Homo sapiens* bisphosphate 3'-nucleotidase mRNA
Accession Number: AF125042

*Homo sapiens* HSPC040 protein mRNA
Accession Number: AF125101

*Homo sapiens* MALT lymphoma associated translocation (MLT) mRNA
Accession Number: AF130356

*Homo sapiens* CGI-10 protein mRNA
Accession Number: AF132944

*Homo sapiens* CGI-26 protein mRNA
Accession Number: AF132960

*Homo sapiens* titin-like protein (TTID) mRNA
Accession Number: AF133820

*Homo sapiens* corin mRNA
Accession Number: AF133845

*Homo sapiens* AKT3 protein kinase mRNA
Accession Number: AF135794

*Homo sapiens* origin recognition complex subunit 6 (ORC6) mRNA
Accession Number: AF139658

*Homo sapiens* CGI-79 protein mRNA
Accession Number: AF151837

*Homo sapiens* CGI-107 protein mRNA
Accession Number: AF151865

*Homo sapiens* CGI-123 protein mRNA
Accession Number: AF151881

*Homo sapiens* CGI-141 protein mRNA
Accession Number: AF151899

*Homo sapiens* CGI-148 protein mRNA
Accession Number: AF151906

*Homo sapiens* ras-related GTP-binding protein 4b (RAB4B) mRNA
Accession Number: AF165522

Homo Sapiens RP58 cDNA for complete mRNA
Accession Number: AJ001388

*Homo sapiens* mRNA for X-like 1 protein
Accession Number: AJ005821

*Homo sapiens* mRNA for cartilage-associated protein (CASP)
Accession Number: AJ006470

*Homo sapiens* mRNA for Rho guanine nucleotide-exchange factor splice variant NET1A
Accession Number: AJ010046

*Homo sapiens* mRNA for Six9 protein
Accession Number: AJ011785

*Homo sapiens* mRNA for NAALADase II protein
Accession Number: AJ012370

*Homo sapiens* mRNA for protein kinase
Accession Number: AJ132545

*Homo sapiens* mRNA for matrilin-3
Accession Number: AJ224741

*Homo sapiens* mRNA for ZNF198 protein
Accession Number: AJ224901

*Homo sapiens* mRNA for centaurin beta2
Accession Number: AJ238248

*Homo sapiens* mRNA for phospholipase A2 activating protein
Accession Number: AJ238243

*Homo sapiens* mRNA for alpha-3-fucosyltransferase
Accession Number: AJ238701

Novel human mRNA similar to mouse gene PICK1 (TR:Q62083)
Accession Number: AL049654

*Homo sapiens* mRNA; cDNA DKFZp566D213 (from clone DKFZp566D213)
Accession Number: AL050275

*Homo sapiens* mRNA; cDNA DKFZp434K151 (from clone DKFZp434K151)
Accession Number: AL080177

*Homo sapiens* mRNA; cDNA DKFZp434F122 (from clone DKFZp434F122)
Accession Number: AL080200

*Homo sapiens* mRNA for phosphoribosyl pyrophosphate synthetase subunit I
Accession Number: D00860

*Homo sapiens* mRNA for FMLP-related receptor (HM63)
Accession Number: D10922

*Homo sapiens* mRNA for HM89
Accession Number: D10924

*Homo sapiens* mRNA for transcription factor E4TF1-47
Accession Number: D13316

*Homo sapiens* mRNA for KIAA0003 gene

Accession Number: D13628

*Homo sapiens* mRNA for ITK
Accession Number: D13720

*Homo sapiens* mRNA for Id-2H
Accession Number: D13891

*Homo sapiens* mRNA for MGC-24
Accession Number: D14043

*Homo sapiens* mRNA for transcription factor AREB6
Accession Number: D15050

*Homo sapiens* mRNA for 6-pyruvoyl-tetrahydropterin synthase
Accession Number: D17400

*Homo sapiens* mRNA for protein tyrosine phosphatase (PTP-BAS type 1)
Accession Number: D21209 NID g452189

*Homo sapiens* mRNA for protein tyrosine phosphatase (PTP-BAS type 2)
Accession Number: D21210 NID g452191

*Homo sapiens* mRNA for protein tyrosine phosphatase (PTP-BAS type 3)
Accession Number: D21211

*Homo sapiens* mRNA for KIAA0032 gene
Accession Number: D25215

*Homo sapiens* mRNA for Tec protein-tyrosine kinase
Accession Number: D29767

*Homo sapiens* DRPLA mRNA for ORF
Accession Number: D31840
*Homo sapiens* mRNA for KIAA0059 gene
Accession Number: D31883

*Homo sapiens* mRNA for KIAA0087 gene
Accession Number: D42038 numan mRNA for SCM-1 (single cysteine motif-1)
Accession Number: D43768

*Homo sapiens* apM1 mRNA for GS3109 (novel adipose specific collagen-like factor) Accession Number: D45371

*Homo sapiens* mRNA for eotaxin
Accession Number: D49372

*Homo sapiens* NAK1 mRNA for DNA binding protein
Accession Number: D49728

*Homo sapiens* mRNA for RNA helicase (HRH1)
Accession Number: D50487

*Homo sapiens* mRNA for apolipoprotein E receptor 2
Accession Number: D50678

*Homo sapiens* mRNA for placental leucine aminopeptidase
Accession Number: D50810

*Homo sapiens* mRNA for ceramide glucosyltransferase
Accession Number: D50840

*Homo sapiens* mRNA for KIAA0141 gene
Accession Number: D50931

*Homo sapiens* mRNA for KIAA0142 gene
Accession Number: D63476

*Homo sapiens* mRNA for T-cluster binding protein
Accession Number: D64015

*Homo sapiens* mRNA for CIRP
Accession Number: D78134

*Homo sapiens* mRNA for neuron derived orphan receptor
Accession Number: D78579

*Homo sapiens* mRNA for KIAA0171 gene
Accession Number: D79993

*Homo sapiens* mRNA for NeuroD
Accession Number: D82347

*Homo sapiens* mRNA for nel-related protein

Accession Number: D83017

*Homo sapiens* mRNA for ankyrin repeat protein
Accession Number: D83197

*Homo sapiens* WS-3 mRNA
Accession Number: D84145

*Homo sapiens* mRNA for CD38
Accession Number: D84276

*Homo sapiens* mRNA for hyaluronan synthase
Accession Number: D84424

*Homo sapiens* mRNA for fungal sterol-C5-desaturase homolog
Accession Number: D85181

*Homo sapiens* mRNA for KIAA0203 gene
Accession Number: D86958

*Homo sapiens* mRNA for KIAA0204 gene
Accession Number: D86959

*Homo sapiens* mRNA for KIAA0226 gene
Accession Number: D86979

*Homo sapiens* mRNA for HCS
Accession Number: D87328

*Homo sapiens* mRNA for KIAA0247 gene
Accession Number: D87434

*Homo sapiens* mRNA for l-caldesmon I
Accession Number: D90452

*Homo sapiens* mRNA for l-caldesmon II
Accession Number: D90453

DNA coding of LeIF E
Accession Number: E00047

DNA coding of interferon-gamma
Accession Number: E00095 cDNA encoding human interferon-8'(1)
Accession Number: E00173 cDNA encoding human interferon-alpha-3
Accession Number: E00176 cDNA encoding human interleukin-2
Accession Number: E00372

DNA coding for human interferon gamma
Accession Number: E00380 cDNA encoding human interleukin-1 precursor
Accession Number: E01058 cDNA encoding human G-CSF
Accession Number: E01219

DNA encoding human prourokinase
Accession Number: E01467 cDNA encoding T cell replacing factor
Accession Number: E01483

DNA encoding human B-cell differentiation factor
Accession Number: E01537 cDNA encoding human TL-4
Accession Number: E02167

DNA encoding human NGF-like peptide
Accession Number: E03588

DNA encoding the pro regionNGF2/NT-3 and its vicinity
Accession Number: E07862

*Homo sapiens* serum response factor (SRF) mRNA
Accession Number: J03161

*Homo sapiens* parathyroid-like protein (associated with humoral hypercalcemia of malignancy) mRNA
Accession Number: J03580

*Homo sapiens* renal carcinoma parathgrad hormone-like peptide mRNA
Accession Number: J03802

*Homo sapiens* phosphatase 2A mRNA
Accession Number: J03804

*Homo sapiens* liver glucose transporter-like protein (GLUT2)
Accession Number: J03810

*Homo sapiens* activation (Act-2) mRNA
Accession Number: J04130

*Homo sapiens* endothelin 3 (EDN3) mRNA
Accession Number: J05081

*Homo sapiens* calcitonin receptor mRNA complete cds
Accession Number: L00587

*Homo sapiens* zinc finger protein basonuclin mRNA
Accession Number: L03427

*Homo sapiens* excision repair protein ERCC6 mRNA
Accession Number: L04791

*Homo sapiens* transcription factor mRNA
Accession Number: L06633

*Homo sapiens* (clone L5) orphan G protein-coupled receptor mRNA
Accession Number: L06797

*Homo sapiens* CD40-ligand mRNA
Accession Number: L07414

*Homo sapiens* transforming growth factor-beta type III receptor (TGF-beta)
mRNA Accession Number: L07594

*Homo sapiens* T cell-specific tyrosine kinase mRNA
Accession Number: L10717

*Homo sapiens* TR3 orphan receptor mRNA
Accession Number: L13740

*Homo sapiens* MHC class I-related protein mRNA
Accession Number: L14848

*Homo sapiens* glutamate decarboxylase (GAD67) mRNA
Accession Number: L16888

*Homo sapiens* AH-receptor mRNA
Accession Number: L19872

*Homo sapiens* I-plastin mRNA
Accession Number: L20826

*Homo sapiens* phosphodiesterase mRNA
Accession Number: L20971

*Homo sapiens* plasma membrane calcium ATPase isoform 2 (ATP2B2) mRNA
Accession Number: L20977

*Homo sapiens* (PWD) gene mRNA 3' end
Accession Number: L25591

*Homo sapiens* X104 mRNA
Accession Number: L27476

*Homo sapiens* beta2-chimaerin mRNA
Accession Number: L29126

*Homo sapiens* ras GTPase-activating-like protein (IQGAP1) mRNA
Accession Number: L33075

*Homo sapiens* receptor protein-tyrosine kinase (HEK11) mRNA
Accession Number: L36642

*Homo sapiens* GT198 mRNA complete ORF
Accession Number: L38933

*Homo sapiens* transcription factor SL1 mRNA
Accession Number: L39060

*Homo sapiens* COX17 mRNA
Accession Number: L77701

*Homo sapiens* protein tyrosine phosphatase mRNA

Accession Number: L77886

*Homo sapiens* inwardly rectifying potassium channel (Kir3.2) mRNA
Accession Number: L78480

*Homo sapiens* cap-binding protein mRNA
Accession Number: M15353

*Homo sapiens* pro-urokinase mRNA
Accession Number: M15476

*Homo sapiens* c-yes-1 mRNA
Accession Number: M15990

*Homo sapiens* steroid sulfatase (STS) mRNA
Accession Number: M16505

*Homo sapiens* mineralocorticoid receptor mRNA (hMR)
Accession Number: M16801

*Homo sapiens* homeo box c8 protein mRNA
Accession Number: M16938

*Homo sapiens* parathyroid hormone-related protein mRNA
Accession Number: M17183

*Homo sapiens* plasminogen activator inhibitor 2 (PAI-2) mRNA
Accession Number: M18082

*Homo sapiens* transforming growth factor-beta-2 mRNA
Accession Number: M19154

*Homo sapiens* insulin-like growth factor (IGF) binding protein mRNA
Accession Number: M20841

*Homo sapiens* steroid receptor TR2 mRNA
Accession Number: M21985

*Homo sapiens* secreted T cell protein (H400; SIS-gamma) mRNA
Accession Number: M23502

*Homo sapiens* parathymosin mRNA
Accession Number: M24398

*Homo sapiens* triiodothyronine recptor (THRA1 ear1) mRNA
Accession Number: M24898

*Homo sapiens* natriuretic peptide precursor mRNA
Accession Number: M25296

*Homo sapiens* (clone pAT 744) potential lymphokine/cytokine mRNA
Accession Number: M25316

*Homo sapiens* muscle phosphofructokinase (PFKM) mRNA
Accession Number: M26066

*Homo sapiens* nuclear-encoded mitochondrial branched chain alpha-keto acid dehydrogenase transacylase subunit (E2b) mRNA
Accession Number: M27093

*Homo sapiens* interleukin 1 receptor mRNA
Accession Number: M27492

*Homo sapiens* transactivator protein (CREB) mRNA
Accession Number: M27691

*Homo sapiens* cystic fibrosis mRNA encoding a presumed transmembrane conductance regulator (CFTR)
Accession Number: M28668

*Homo sapiens* hnRNP B1 protein mRNA
Accession Number: M29064

*Homo sapiens* hnRNP A2 protein mRNA
Accession Number: M29065

*Homo sapiens* calcineurin A2 mRNA
Accession Number: M29551

*Homo sapiens* zinc finger protein X-linked (ZFX) mRNA
Accession Number: M30608

*Homo sapiens* amphiregulin (AR) mRNA complete cds clones lambda-AR1 and lambda-AR2
Accession Number: M30704

*Homo sapiens* calcineurin B mRNA
Accession Number: M30773

*Homo sapiens* insulin-like growth factor binding protein mRNA
Accession Number: M31145

*Homo sapiens* papillary thyroid carcinoma-encoded protein mRNA Accession Number: M31213

*Homo sapiens* sorcin CP-22 mRNA
Accession Number: M32886

*Homo sapiens* cytokine (GRO-gamma) mRNA
Accession Number: M36821

*Homo sapiens* macrophage-specific colony-stimulating factor (CSF-1) mRNA
Accession Number: M37435

*Homo sapiens* p58/GTA (galactosyltransferase associated protein kinase) mRNA
Accession Number: M37712

*Homo sapiens* MEM-102 glycoprotein mRNA
Accession Number: M37766

*Homo sapiens* interferon-alpha mRNA
Accession Number: M54886 M38682

*Homo sapiens* interleukin 6 mRNA
Accession Number: M54894 M38669

*Homo sapiens* iduronate 2-sulfatase mRNA
Accession Number: M58342 M38371

*Homo sapiens* ELAM-1 ligand fucosyltransferase (ELFT) mRNA
Accession Number: M58597

*Homo sapiens* pan-leukocyte antigen (CD48) mRNA
Accession Number: M59904

*Homo sapiens* transforming growth factor-beta (tgf-beta) mRNA
Accession Number: M60315 M38693 M38694

*Homo sapiens* keratinocyte growth factor mRNA

Accession Number: M60828 M25295

*Homo sapiens* cleavage signal 1 protein mRNA
Accession Number: M61199

*Homo sapiens* gamma-aminobutyric acid receptor type A rho-1 subunit (GABA-A rho-1) mRNA
Accession Number: M62400 M62323

*Homo sapiens* luteinizing hormone-choriogonadrotropin receptor mRNA
Accession Number: M63108

*Homo sapiens* rac protein kinase alpha mRNA
Accession Number: M63167

*Homo sapiens* phospholamban mRNA
Accession Number: M63603

*Homo sapiens* caldesmon mRNA
Accession Number: M64110

*Homo sapiens* endothelin 2 (ET2) mRNA
Accession Number: M65199

*Homo sapiens* cdc2-related protein kinase mRNA
Accession Number: M68520

*Homo sapiens* phosphatidylcholine 2-acylhydrolase (cPLA2) mRNA
Accession Number: M68874

*Homo sapiens* GATA-binding protein (GATA2) mRNA
Accession Number: M68891

*Homo sapiens* MAD-3 mRNA encoding IkB-like activity
Accession Number: M69043

*Homo sapiens* lutropin/choriogonadotropin receptor (LHCGR) mRNA
Accession Number: M73746

*Homo sapiens* HK-ATPase beta subunit mRNA
Accession Number: M75110

*Homo sapiens* transcription factor GATA-2 (GATA-2) mRNA

Accession Number: M77810

*Homo sapiens* glutamate decarboxylase (GAD67) mRNA
Accession Number: M81883

*Homo sapiens* aorta caldesmon mRNA
Accession Number: M83216

*Homo sapiens* formyl peptide receptor-like receptor (FPRL1) mRNA
Accession Number: M84562

*Homo sapiens* skeletal muscle alpha 2 actinin (ACTN20 mRNA
Accession Number: M86406

*Homo sapiens* fibroblast growth factor receptor (K-sam) mRNA
Accession Number: M87770

*Homo sapiens* D3-type cyclin (CCND3) mRNA
Accession Number: M90814

*Homo sapiens* cyclin D3 (CCND3) mRNA
Accession Number: M92287

*Homo sapiens* homeobox 2.1 protein (HOX2A) mRNA
Accession Number: M92299

*Homo sapiens* zinc finger transcriptional regulator mRNA
Accession Number: M92843

*Homo sapiens* cholesterol 7-alpha hydroxylase (CYP7) mRNA
Accession Number: M93133

*Homo sapiens* protein tyrosine phosphatase zeta-polypeptide (PTPRZ) mRNA
Accession Number: M93426

*Homo sapiens* striated muscle contraction regulatory protein (Id2B) mRNA
Accession Number: M96843

*Homo sapiens* nucleolysin TIAR mRNA
Accession Number: M96954

*Homo sapiens* beta-16-N-acetylglucosaminyltransferase mRNA
Accession Number: M97347

*Homo sapiens* rolipram-sebsitive cAMP-specific phosphodiesterase (PDE2)
mRNA Accession Number: M97515

GADD153=growth arrest and DNA-damage-inducible gene [human
Genomic/mRNA 895 nt]
Accession Number: S40706 calcineurin A catalytic subunit [human testis mRNA 2134 nt]
Accession Number: S46622

TLS/CHOP=hybrid gene {translocation breakpoint} [human myxoid liposarcomas
cells mRNA Mutant 1682 nt]
Accession Number: S62138

RBP1=retinoblastoma binding protein 1 [human Nalm-6 pre-B cell leukemia
mRNA 4834 nt]
Accession Number: S66427

CD36=collagen type I/thrombospondin receptor {one exon} [human mRNA
Partial 369 nt]
Accession Number: S67044 glycogen synthase [human liver mRNA 2912 nt]
Accession Number: S70004

AgX-1 antigen [human infertile patient testis mRNA 2279 nt]
Accession Number: S73498

A-myb=DNA-binding transactivator {3' region} [human CCRF-CEM
T-leukemia line mRNA Partial 831 nt]
Accession Number: S75881 voltage-gated chloride channel [human placenta Genomic/mRNA 3440
nt]
Accession Number: S77770 nuc2 homolog [human fibroblasts mRNA 3320 nt]
Accession Number: S78234

N8=tumor expression-enhanced gene [human NCI H-69 cell line mRNA
2185 nt]
Accession Number: S82081

Evi-1=Evi-1 protein {3' region deletion region} [human
    megakaryoblastoid cell line MOLM-1 chronic myelocytic leukemia
    patient mRNA Partial Mutant 916 nt]
Accession Number: S82592 interleukin-2 [human placenta term placentas obtained by cesarean
    section mRNA 1028 nt]
Accession Number: S82692

HOXC6=homeodomain-containing protein {clone 211} [human MCF7
    mRNA 1608 nt]
Accession Number: S82986 germ cell nuclear factor [human embryonal carcinoma NT2/D1 mRNA
    1916 nt]
Accession Number: S83309

*Homo sapiens* glutamine PRPP amidotransferase (GPAT) mRNA
Accession Number: U00238

*Homo sapiens* guanine nucleotide regulatory protein (NET1) mRNA
Accession Number: U02081

*Homo sapiens* dioxin-inducible cytochrome P450 (CYP1B1) mRNA
Accession Number: U03688

*Homo sapiens* maspin mRNA
Accession Number: U04313

*Homo sapiens* POU domain protein (Brn-3b) mRNA
Accession Number: U06233

*Homo sapiens* steroid hormone receptor Ner-I mRNA
Accession Number: U07132

*Homo sapiens* ISL-1 (Islet-1) mRNA
Accession Number: U07559

*Homo sapiens* NAD(H)-specific isocitrate dehydrogenase alpha subunit
    precursor mRNA
Accession Number: U07681

*Homo sapiens* aldehyde dehydrogenase 6 mRNA
Accession Number: U07919

*Homo sapiens* urokinase-type plasminogen activator receptor mRNA
Accession Number: U08839

*Homo sapiens* serine kinase mRNA
Accession Number: U09564

*Homo sapiens* glutamate receptor flip isoform (GluR3-flip) mRNA
Accession Number: U10301

*Homo sapiens* ileal sodium-dependent bile acid transporter (SLC10-A2) mRNA
Accession Number: U10417

*Homo sapiens* calcium dependent potassium channel alpha subunit (MaxiK)
mRNA Accession Number: U11058

*Homo sapiens* copper transporting ATPase mRNA
Accession Number: U11700

*Homo sapiens* protein tyrosine phosphatase 1E (PTP1E) mRNA
Accession Number: U12128

*Homo sapiens* mitogen induced nuclear orphan receptor (MINOR) mRNA
Accession Number: U12767

*Homo sapiens* nuclear respiratory factor-2 subunit gamma 1 mRNA
Accession Number: U13047

*Homo sapiens* nuclear respiratory factor-2 subunit gamma 2 mRNA
Accession Number: U13048

*Homo sapiens* forkhead protein FREAC-1 mRNA
Accession Number: U13219

*Homo sapiens* large-conductance calcium-activated potassium channel (hSlo)
mRNA Accession Number: U13913

*Homo sapiens* TFIIA gamma subunit mRNA
Accession Number: U14193

*Homo sapiens* interleukin 15 (IL15) mRNA

Accession Number: U14407

*Homo sapiens* glioma pathogenesis-related protein (GliPR) mRNA
Accession Number: U16307

*Homo sapiens* nuclear autoantigen GS2NA mRNA
Accession Number: U17989

*Homo sapiens* spinal muscular atrophy gene product mRNA
Accession Number: U18423

*Homo sapiens* putative transmembrane protein mRNA
Accession Number: U19252

*Homo sapiens* transmembrane protein mRNA
Accession Number: U19878

*Homo sapiens* Tg737 mRNA
Accession Number: U20362

*Homo sapiens* atrophin-1 mRNA
Accession Number: U23851

*Homo sapiens* phosphofructokinase (PFKM) mRNA
Accession Number: U24183

*Homo sapiens* heterochromatin protein HP1Hs-gamma mRNA
Accession Number: U26312

*Homo sapiens* beta2-chimaerin mRNA
Accession Number: U28926

*Homo sapiens* G protein gamma-10 subunit mRNA
Accession Number: U31383

*Homo sapiens* IL-17 mRNA
Accession Number: U32659

*Homo sapiens* retinoic acid- and interferon-inducible 58K protein RI58
    mRNA
Accession Number: U34605

*Homo sapiens* kinesin-like spindle protein HKSP (HKSP) mRNA

Accession Number: U37426

*Homo sapiens* Mch3 isoform beta (Mch3) mRNA
Accession Number: U37449

*Homo sapiens* dlg3 mRNA
Accession Number: U37707

*Homo sapiens* Rab27a mRNA
Accession Number: U38654

*Homo sapiens* mab-21 cell fate-determining protein homolog (CAGR1) mRNA
Accession Number: U38810

*Homo sapiens* clone hGIRK1 G-protein coupled inwardly rectifying potassium
channel mRNA
Accession Number: U39196

*Homo sapiens* MAP kinase kinase 6 (MKK6) mRNA
Accession Number: U39657

*Homo sapiens* cysteine protease CMH-1 mRNA
Accession Number: U40281

*Homo sapiens* CDK inhibitor p19INK4d mRNA
Accession Number: U40343

*Homo sapiens* metalloprotease/disintegrin/cysteine-rich protein precursor
(MDC9) mRNA
Accession Number: U41766

*Homo sapiens* cardiotrophin-1 (CTF1) mRNA
Accession Number: U43030

*Homo sapiens* vascular endothelial growth factor related protein VRP mRNA
Accession Number: U43142

*Homo sapiens* myotubularin (MTM1) mRNA
Accession Number: U46024

*Homo sapiens* eotaxin precursor mRNA
Accession Number: U46573

*Homo sapiens* occludin mRNA
Accession Number: U49184

*Homo sapiens* serotonin 5-HT2c receptor mRNA
Accession Number: U49516

*Homo sapiens* LIM protein MLP mRNA
Accession Number: U49837

*Homo sapiens* guanine nucleotide exchange factor p532 mRNA
Accession Number: U50078

*Homo sapiens* adenosine kinase mRNA
Accession Number: U50196

*Homo sapiens* betaine:homocysteine methyltransferase mRNA
Accession Number: U50929

*Homo sapiens* G protein-activated inwardly rectifying potassium channel
   HGIRK1/Kir3.1 mRNA
Accession Number: U50964

*Homo sapiens* G/T mismatch-specific thymine DNA glycosylase mRNA
Accession Number: U51166

*Homo sapiens* hexokinase III (HK3) mRNA
Accession Number: U51333

*Homo sapiens* inwardly rectifying potassium channel Kir3.2 mRNA
Accession Number: U52153

*Homo sapiens* GOK (STIM1) mRNA
Accession Number: U52426

*Homo sapiens* periodic tryptophan protein 2 (PWP2) mRNA
Accession Number: U56085

*Homo sapiens* Fc alpha receptor b deltaS2 mRNA
Accession Number: U56237

*Homo sapiens* lysophosphatidic acid acyltransferase-alpha mRNA
Accession Number: U56417

*Homo sapiens* putative serine/threonine protein kinase PRK (prk) mRNA
Accession Number: U56998

*Homo sapiens* fetal brain oculocerebrorenal syndrome (OCRL1) mRNA
Accession Number: U57627

*Homo sapiens* retinitis pigmentosa GTPase regulator (RPGR) mRNA
Accession Number: U57629

*Homo sapiens* hyaluronan synthase mRNA
Accession Number: U59269

*Homo sapiens* haemochromatosis protein (HLA-H) mRNA
Accession Number: U60319

*Homo sapiens* transmembrane protein Jagged 1 (HJ1) mRNA
Accession Number: U61276

*Homo sapiens* GT334 protein (GT334) gene mRNA
Accession Number: U61500

*Homo sapiens* cyclin G1 interacting protein (1500GX1) mRNA
Accession Number: U61835

*Homo sapiens* enterocyte differentiation associated factor EDAF-1
    mRNA
Accession Number: U62136

*Homo sapiens* oxytocinase variant 2 mRNA
Accession Number: U62769

*Homo sapiens* canalicular multispecific organic anion transporter (cMOAT)
    mRNA
Accession Number: U63970

*Homo sapiens* Lice2 beta cysteine protease mRNA
Accession Number: U67319

*Homo sapiens* Lice2 gamma cysteine protease mRNA
Accession Number: U67320

*Homo sapiens* beige protein homolog (chs) mRNA

Accession Number: U67615

*Homo sapiens* megakaryocyte stimulating factor mRNA
Accession Number: U70136

*Homo sapiens* ataxin-2 (SCA2) mRNA
Accession Number: U70323

*Homo sapiens* snRNA activating protein complex 50kD subunit (SNAP50) mRNA
Accession Number: U71300

*Homo sapiens* telencephalin precursor mRNA
Accession Number: U72671

*Homo sapiens* dsRNA adenosine deaminase DRADA2a (DRADA2a) mRNA
Accession Number: U76420

*Homo sapiens* dsRNA adenosine deaminase DRADA2b (DRADA2b) mRNA
Accession Number: U76421

*Homo sapiens* 68 kDa type I phosphatidylinositol-4-phosphate 5-kinase alpha
mRNA clone PIP5KIa1
Accession Number: U78575

*Homo sapiens* clone 23733 mRNA
Accession Number: U79274

*Homo sapiens* basic-leucine zipper nuclear factor (JEM-1) mRNA
Accession Number: U79751

*Homo sapiens* TFIID subunit TAFII100 mRNA
Accession Number: U80191

*Homo sapiens* orphan nuclear receptor GCNF mRNA
Accession Number: U80802

*Homo sapiens* basic-leucine zipper transcription factor MafG (MAFG)
mRNA
Accession Number: U84249

*Homo sapiens* CX3C chemokine precursor mRNA alternatively spliced
Accession Number: U84487

*Homo sapiens* lysyl hydroxylase isoform 2 (PLOD2) mRNA
Accession Number: U84573

*Homo sapiens* putative endothelin receptor type B-like protein mRNA
Accession Number: U87460

*Homo sapiens* placental bone morphogenic protein PLAB mRNA
Accession Number: U88323

*Homo sapiens* dentin matrix acidic phosphoprotein 1 (DMP1) mRNA
Accession Number: U89012

*Homo sapiens* proneurotensin/proneuromedin N mRNA
Accession Number: U91618

*Homo sapiens* CX3C chemokine precursor mRNA alternatively spliced
Accession Number: U91835

*Homo sapiens* retina-derived POU-domain factor-1 mRNA
Accession Number: U91934

*Homo sapiens* retina-derived POU-domain factor-1 mRNA alternatively spliced
Accession Number: U91935

*Homo sapiens* metabotropic glutamate receptor 8 mRNA
Accession Number: U92459

*Homo sapiens* Toll protein homolog mRNA and LINE-1 reverse transcriptase homolog pseudogene
Accession Number: U93091

*Homo sapiens* RNA polymerase III subunit (RPC39) mRNA
Accession Number: U93869

Messenger RNA for human leukocyte (alpha) interferon
Accession Number: V00551

*Homo sapiens* mRNA encoding phosphoglycerate kinase
Accession Number: V00572

*Homo sapiens* mRNA for interleukin 1-alpha
Accession Number: X02531

*Homo sapiens* mRNA for interleukin-1 precursor (pre IL-1)
Accession Number: X02851

*Homo sapiens* mRNA for alpha-glucocorticoid receptor (clone OB7)
Accession Number: X03225

*Homo sapiens* mRNA of trk oncogene
Accession Number: X03541

*Homo sapiens* mRNA for Na/K-ATPase beta subunit
Accession Number: X03747

*Homo sapiens* tonsillar lymphocyte LD78 mRNA induced by TPA or PHA TPA =
12-o-tetradecanoyl phorbol-13 acetate (tumor promoter) PHA =
phytohemagglutinin (T-cell mitogen)
Accession Number: X03754

*Homo sapiens* erythrocyte 23-bisphosphoglycerate mutase mRNA EC 2.7.5.4.
Accession Number: X04327

*Homo sapiens* IFN-beta 2a mRNA for interferon-beta-2
Accession Number: X04430

*Homo sapiens* mRNA for thrombomodulin precursor
Accession Number: X05495

*Homo sapiens* mRNA for trk-2h oncogene
Accession Number: X06704 Y00100

*Homo sapiens* mRNA for protein phosphatase 2A (alpha-type)
Accession Number: X12646 M36951

*Homo sapiens* 12S RNA induced by poly(rI) poly(rC) and Newcastle disease
    virus
Accession Number: X13956

*Homo sapiens* mRNA for pro-alpha-1 type 3 collagen
Accession Number: X14420

*Homo sapiens* mRNA for GABA-A receptor alpha 1 subunit
Accession Number: X14766

*Homo sapiens* mRNA for transmembrane carcinoembryonic antigen BGPb
(formerly TM2-CEA)
Accession Number: X14831 X14784

*Homo sapiens* mRNA for transmembrane carcinoembryonic antigen BGPa
(formerly TM1-CEA)
Accession Number: X16354 X14784

*Homo sapiens* mRNA for NAD-dependent methylene tetrahydrofolate
dehydrogenase cyclohydrolase (EC 1.5.1.15)
Accession Number: X16396

*Homo sapiens* c-abl mRNA encoding p150 protein
Accession Number: X16416

*Homo sapiens* HOX2H mRNA from the Hox2 locus
Accession Number: X16665

*Homo sapiens* mRNA for integrin alpha-4 subunit
Accession Number: X16983 X15356

*Homo sapiens* mRNA for integrin alpha-2 subunit
Accession Number: X17033 M28249

*Homo sapiens* mRNA for beta-casein
Accession Number: X17070

*Homo sapiens* mRNA for n-chimaerin
Accession Number: X51408

*Homo sapiens* endothelin 3 mRNA
Accession Number: X52001

*Homo sapiens* mRNA for uracil-DNA glycosylase
Accession Number: X52486

*Homo sapiens* mRNA for beta nerve growth factor
Accession Number: X52599

*Homo sapiens* mRNA for cardiac gap junction protein
Accession Number: X52947

*Homo sapiens* LAG-1 mRNA

Accession Number: X53683

*Homo sapiens* mRNA for macrophage inflammatory protein-2beta (MIP2beta)
Accession Number: X53800

*Homo sapiens* cDNA for CREB protein
Accession Number: X55545

*Homo sapiens* mRNA for pM5 protein
Accession Number: X57398

*Homo sapiens* serotonin 5-HT2 receptor mRNA
Accession Number: X57830

*Homo sapiens* D13S106 mRNA for a highly charged amino acid sequence
Accession Number: X59131

*Homo sapiens* RR2 mRNA for small subunit ribonucleotide reductase
Accession Number: X59618 S40301 S40302

*Homo sapiens* TCF-1 mRNA for T cell factor 1 (splice form B)
Accession Number: X59870 X55329

*Homo sapiens* TCF-1 mRNA for T cell factor 1 (splice form C)
Accession Number: X59871 X55328

*Homo sapiens* KALIG-1 mRNA for neural cell adhesion and axonal
    path-finding molecule homologue
Accession Number: X60299

*Homo sapiens* polypyrimidine tract-binding (PTB) mRNA for polypyrimidine
    tract-binding protein (pPTB)
Accession Number: X60648

*Homo sapiens* mRNA for P2 protein of peripheral myelin
Accession Number: X62167

*Homo sapiens* mRNA (TRK-T1) for 55 KD protein
Accession Number: X62947

*Homo sapiens* mRNA for serum response factor-related protein
    RSRFC4
Accession Number: X63381

*Homo sapiens* mRNA for plasma membrane calcium ATPase
Accession Number: X63575 S37350 S95738 S95743 S95758 S95777 S95783

*Homo sapiens* mRNA for APO-1 cell surface antigen
Accession Number: X63717

*Homo sapiens* mRNA for transacylase (DBT)
Accession Number: X66785 S48130

*Homo sapiens* MaTu MN mRNA for p54/58N protein
Accession Number: X66839

*Homo sapiens* mRNA for heterogeneous nuclear ribonucleoprotein
Accession Number: X66975 S41306

*Homo sapiens* mRNA for CD40 ligand
Accession Number: X67878 S50586

*Homo sapiens* mRNA for myocyte-specific enhancer factor 2 (MEF2)
Accession Number: X68505

*Homo sapiens* TRAP mRNA for ligand of CD40
Accession Number: X68550 S49008

*Homo sapiens* interleukin-13 mRNA
Accession Number: X69079

*Homo sapiens* mRNA for calcitonin receptor
Accession Number: X69920

*Homo sapiens* FMR-1 mRNA
Accession Number: X69962

*Homo sapiens* mRNA for FUS-CHOP protein fusion
Accession Number: X71427

*Homo sapiens* ERGIC-53 mRNA
Accession Number: X71661

*Homo sapiens* mRNA encoding Rev-ErbAalpha (internal fragment)
Accession Number: X72632 X53327

*Homo sapiens* mRNA for nicein B2 chain
Accession Number: X73902

*Homo sapiens* p130 mRNA for 130K protein
Accession Number: X76061

*Homo sapiens* mRNA for vacuolar H+ ATPase E subunit
Accession Number: X76228

*Homo sapiens* mRNA for 2-5A binding protein
Accession Number: X76388

*Homo sapiens* mRNA for cathepsin-O
Accession Number: X77383

*Homo sapiens* GD3 synthase mRNA
Accession Number: X77922

*Homo sapiens* HZF10 mRNA for zinc finger protein
Accession Number: X78933

*Homo sapiens* AUH mRNA
Accession Number: X79888

*Homo sapiens* ERK3 mRNA
Accession Number: X80692

*Homo sapiens* hTFIIAs mRNA for smallest (gamma) TFIIA subunit
Accession Number: X81713

*Homo sapiens* HOK-2 mRNA for zinc finger protein
Accession Number: X82125

*Homo sapiens* Staf50 mRNA
Accession Number: X82200

*Homo sapiens* mRNA for alpha-centractin
Accession Number: X82206

*Homo sapiens* Brain 4 mRNA
Accession Number: X82324

*Homo sapiens* SMA4 mRNA

Accession Number: X83300

*Homo sapiens* mRNA for phosphatidylinositol 3 kinase gamma
Accession Number: X83368

*Homo sapiens* mRNA for TRPC1 protein
Accession Number: X89066

*Homo sapiens* mRNA for ESM-1 protein
Accession Number: X89426

*Homo sapiens* mRNA for microsomal triglyceride transfer protein
Accession Number: X91148

*Homo sapiens* mRNA for MHC class I mic-B antigen
Accession Number: X91625

*Homo sapiens* mRNA for translin associated protein X
Accession Number: X95073

*Homo sapiens* mRNA for PWP2 protein
Accession Number: X95263

*Homo sapiens* mRNA for translational inhibitor protein p14.5.
Accession Number: X95384

*Homo sapiens* mRNA for TAFII100 protein
Accession Number: X95525

*Homo sapiens* mRNA for C1D protein
Accession Number: X95592

*Homo sapiens* mRNA for canalicular multidrug resistance protein
Accession Number: X96395

*Homo sapiens* mRNA for TIM17 preprotein translocase
Accession Number: X97544

*Homo sapiens* mRNA for protein induced by vitamin D
Accession Number: X98091

*Homo sapiens* mRNA for FAA protein
Accession Number: X99226

*Homo sapiens* hap mRNA encoding a DNA-binding hormone receptor
Accession Number: Y00291

*Homo sapiens* mRNA for Arg-Serpin (plasminogen activator-inhibitor 2 PAI-2)
Accession Number: Y00630

*Homo sapiens* mRNA for muscle phosphofructokinase (E.C. 2.7.1.11).
Accession Number: Y00698

*Homo sapiens* mRNA for insulin-like growth factor binding protein IBP-1 (IGF-binding protein)
Accession Number: Y00856

*Homo sapiens* mRNA for WNT11 gene
Accession Number: Y12692

*Homo sapiens* mRNA for FIM protein
Accession Number: Y13472

*Homo sapiens* mRNA for farnesylated-proteins converting enzyme 2
Accession Number: Y13835

*Homo sapiens* mRNA for DIF-2 protein
Accession Number: Y14551

*Homo sapiens* mRNA for
    UDP-galactose:2-acetamido-2-deoxy-D-glucose3beta-
    galactosyltransferase
Accession Number: Y15014

*Homo sapiens* mRNA for serum response factor-related protein
    RSRFC9
Accession Number: Y16312

*Homo sapiens* mRNA for CDS2 protein
Accession Number: Y16521

*Homo sapiens* mRNA for monocyte chemotactic protein-2
Accession Number: Y16645

*Homo sapiens* mRNA for protein phosphatase 1 (PPP1R6)
Accession Number: Y18206

*Homo sapiens* mRNA for N-Oct 3 N-Oct5a and N-Oct 5b proteins
Accession Number: Z11933

*Homo sapiens* mRNA for laminin
Accession Number: Z15008 S47028

*Homo sapiens* ALK-2 mRNA
Accession Number: Z22534

*Homo sapiens* ALK-3 mRNA
Accession Number: Z22535

*Homo sapiens* a2-chimaerin mRNA
Accession Number: Z22641

*Homo sapiens* (23k/3) mRNA for ubiquitin-conjugating enzyme UbcH2
Accession Number: Z29331

*Homo sapiens* mRNA for 43 kDa inositol polyphosphate 5-phosphatase
Accession Number: Z31695

*Homo sapiens* mRNA for membrane transport protein (XK gene)
Accession Number: Z32684

*Homo sapiens* HK2 mRNA for hexokinase II
Accession Number: Z46376

*Homo sapiens* CTLA8 mRNA
Accession Number: Z58820

*Homo sapiens* mRNA for phosphotyrosine phosphatase kappa
Accession Number: Z70660

*Homo sapiens* mRNA for TRPC1A
Accession Number: Z73903

*Homo sapiens* mRNA for CC-chemokine eotaxin variant (clone 53)
Accession Number: Z75668

SEQUENCE LISTING

<160> NUMBER OF SEQ ID NOS: 7

<210> SEQ ID NO 1
<211> LENGTH: 13
<212> TYPE: RNA
<213> ORGANISM: Artificial Sequence
<220> FEATURE:
<223> OTHER INFORMATION: consensus motif

<400> SEQUENCE: 1
wwwuauuuau www                                              13

<210> SEQ ID NO 2
<211> LENGTH: 7
<212> TYPE: RNA
<213> ORGANISM: Artificial Sequence
<220> FEATURE:
<223> OTHER INFORMATION: consensus motif

<400> SEQUENCE: 2 uauuuau                                                     7

<210> SEQ ID NO 3
<211> LENGTH: 21
<212> TYPE: RNA
<213> ORGANISM: Artificial Sequence
<220> FEATURE:
<223> OTHER INFORMATION: consensus motif

<400> SEQUENCE: 3
auuuauuuau uauuuauuu a                                      21

<210> SEQ ID NO 4
<211> LENGTH: 17
<212> TYPE: RNA
<213> ORGANISM: Artificial Sequence
<220> FEATURE:
<223> OTHER INFORMATION: consensus motif

<400> SEQUENCE: 4
auuuauuuau uuauuua                                          17

```
<210> SEQ ID NO 5
<211> LENGTH: 15
<212> TYPE: RNA
<213> ORGANISM: Artificial Sequence
<220> FEATURE:
<223> OTHER INFORMATION: consensus motif

<400> SEQUENCE: 5
wauuuauuua uuuaw                                             15

<210> SEQ ID NO 6
<211> LENGTH: 13
<212> TYPE: RNA
<213> ORGANISM: Artificial Sequence
<220> FEATURE:
<223> OTHER INFORMATION: consensus motif

<400> SEQUENCE: 6
wwauuuauuu aww                                               13

<210> SEQ ID NO 7
<211> LENGTH: 13
<212> TYPE: RNA
<213> ORGANISM: Artificial Sequence
<220> FEATURE:
<223> OTHER INFORMATION: consensus motif

<400> SEQUENCE: 7
wwwwauuuaw www                                               13
```

SMALL MOLECULE INHIBITORS OF SECRETION OF PROTEINS ENCODED BY ARE-MRNAS

CROSS-REFERENCE TO RELATED APPLICATION

This application claims the benefit of the filing date of U.S. provisional application No. 60/282,974, filed Apr. 10, 2001.

BACKGROUND OF THE INVENTION

In general, the invention relates to methods and compounds that decrease secretion of proteins encoded by ARE-mRNAs, such as Tumor Necrosis Factor (TNFα), or that modulate regulation of ARE-mRNAs.

ARE-mRNAs are mRNA molecules that contain an adenylate uridylate (AU)-rich element. AREs are usually found in the 3' untranslated region (3' UTR) of mRNAs rather than in the coding region. ARE regulatory regions modulate the rate of mRNA degradation and the rate of translation. A database of human mRNAs containing an ARE consensus sequence was recently reported (Bakheet et al., Nucleic Acids Research 29:246–254, 2001).

One such ARE-mRNA encodes TNFα, which is a pleiotropic cytokine produced predominantly by activated monocytes/macrophages. TNFα is a primary mediator of numerous immune functions, including hemorrhagic cytotoxicity, inflammation, and regulation of antiviral and immune proliferative and activation responses. As a central member of the cytokine network, TNFα has been implicated in a variety of disease states, including cachexia, endotoxic (septic) shock, acute respiratory distress syndrome, and a number of necrotic, proliferative, and autoimmune diseases.

TNFα exhibits a potent cytolytic and cytostatic activity towards a variety of cells, including tumor cell lines and virally infected cells. For example, TNFα is a potent mediator of monocyte/macrophage migration, activation, and differentiation. In addition, TNFα stimulates activated T-cells and B-cells and enhances neutrophil chemotaxis and phagocytic activity. Endothelial cells are also primary targets of TNFα activity; for example, TNFα induces the release of IL-1 from endothelial cells and promotes endothelial cell procoagulant activity and neutrophil adhesion, which are involved in local inflammatory responses. TNFα also stimulates fibroblast migration, proliferation, and cytokine production.

SUMMARY OF THE INVENTION

The present invention features compounds and methods for inhibiting secretion of proteins encoded by ARE-mRNAs, such as Tumor Necrosis Factor (TNFα), or modulating regulation of ARE-mRNAs. The compounds of the present invention may be used as therapeutics to inhibit TNFα secretion in a desired cell, such as a cell of the immune system (e.g., a macrophage, monocyte, T-cell, B-cell, granulocyte, eosinophil, mast cell, fibroblast, smooth muscle cell, chondrocyte, osteoblast, glial cell, keratinocyte, or endothelial cell). These compounds are useful for treating or preventing a number of diseases, including but not limited to inflammatory conditions, arthritis, autoimmune diseases, septic shock, blood clots, and stroke.

Accordingly, in one aspect, the invention features a compound having the formula:

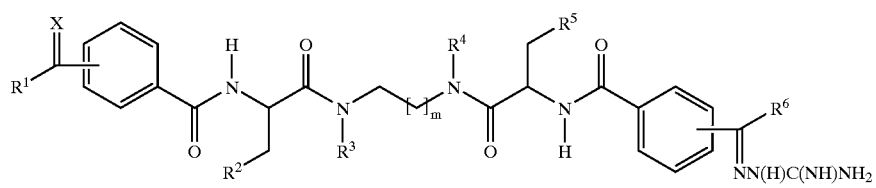

or a derivative thereof. $R^1$ and $R^6$ are independently selected from the group consisting of an alkyl and an aryl group; $R^2$ and $R^5$ are independently selected from the group consisting of hydrogen, an alkyl, and an aryl group; and $R^3$ and $R^4$ are independently selected from the group consisting of hydrogen and an alkyl group. X is oxygen or $H_2N(HN)C(H)NN—$, and m is at least one. In various embodiments, m is between 1 and 15, 1 and 10, or 1 and 5, inclusive. In other embodiments, m is one or two. In still other embodiments, $R^1$ or $R^6$ is a methyl group. In yet other embodiments, $R^2$ or $R^5$ is a phenyl, 4-Cl-phenyl, 4-I-phenyl, 4-F-phenyl, 4-nitro-phenyl, 4-phenyl-phenyl, or 4-methoxy-phenyl group. In other embodiments, $R^3$ and $R^4$ are hydrogen. In still other embodiments, $R^2$ is a phenyl group and $R^5$ is an isopropyl group, or $R^2$ is an isopropyl group and $R^5$ is a phenyl group.

In a related aspect, the invention features a compound having the formula:

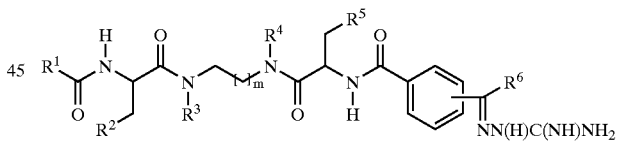

or a derivative or salt thereof. $R^1$ and $R^6$ are independently selected from the group consisting of an alkyl and an aryl group; $R^2$ and $R^5$ are independently selected from the group consisting of hydrogen, an alkyl, and an aryl group; $R^3$ and $R^4$ are independently selected from the group consisting of hydrogen and an alkyl. M is at least one. In various embodiments, m is between 1 and 15, 1 and 10, or 1 and 5, inclusive. In other embodiments, m is one or two. In still other embodiments, $R^2$ or $R^6$ is a methyl or phenyl group. In other embodiments, $R^2$ or $R^5$ is a phenyl, 4-Cl-phenyl, 4-I-phenyl, 4-F-phenyl, 4-nitro-phenyl, 4-phenyl-phenyl, or 4-methoxy-phenyl group. In yet other embodiments, $R^3$ and $R^4$ are hydrogen. In another embodiment, $R^2$ is a phenyl group and $R^5$ is an isopropyl group, or $R^2$ is an isopropyl group and $R^5$ is a phenyl group.

In another aspect, the invention provides a compound having the formula:

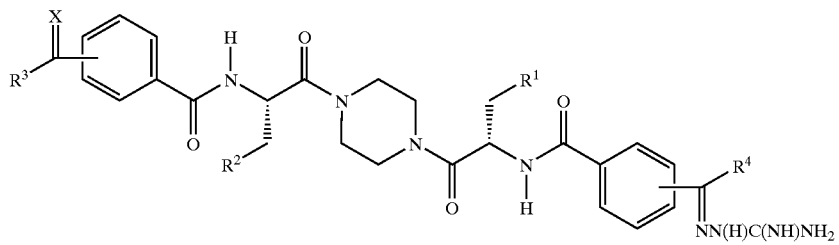

or a derivative or salt thereof. $R^1$ and $R^2$ are independently selected from the group consisting of hydrogen, an alkyl, and an aryl group; $R^3$ and $R^4$ are independently selected from the group consisting of an alkyl and an aryl group. X is oxygen or $H_2N(HN)C(H)NN—$. In various embodiments, $R^3$ or $R^4$ is a phenyl or methyl group. In particular embodiments, $R^1$ or $R^2$ is a phenyl, 4-Cl-phenyl, 4-I-phenyl, 4-F-phenyl, 4-nitro-phenyl, 4-phenyl-phenyl, or 4-methoxy-phenyl group. In still other embodiments, $R^1$ is a phenyl group and $R^2$ is an isopropyl group, or $R^1$ is an isopropyl group and $R^2$ is a phenyl group.

In another aspect, the invention provides a compound having the formula:

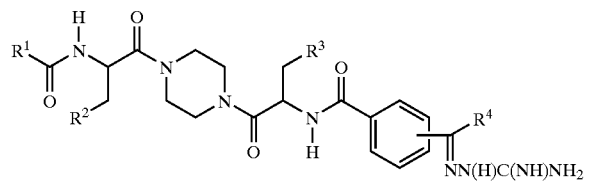

or a derivative or salt thereof. $R^1$ and $R^4$ are independently selected from the group consisting of an alkyl or an aryl group. $R^2$ and $R^3$ are independently selected from the group consisting of hydrogen, an alkyl, and an aryl group. In various embodiments, $R^1$ or $R^4$ is a phenyl or methyl group. In other embodiments, $R^2$ or $R^3$ is a phenyl, 4-Cl-phenyl, 4-I-phenyl, 4-F-phenyl, 4-nitro-phenyl, 4-phenyl-phenyl, or 4-methoxy-phenyl group. In still other embodiments, $R^2$ is a phenyl group and $R^3$ is an isopropyl group, or $R^2$ is an isopropyl group and $R^3$ is a phenyl group.

In a related aspect, the invention features a compound having the formula:

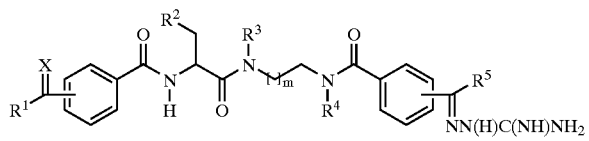

or a derivative or salt thereof. $R^1$ and $R^5$ are independently selected from the group consisting an aryl or alkyl group; $R^2$ is hydrogen, an alkyl, or aryl group. $R^3$ and $R^4$ are independently selected from the group consisting of hydrogen and an alkyl group. X is oxygen or $H_2N(HN)C(H)NN—$; and m is at least one. In various embodiments, m is between 1 and 15, 1 and 10, or 1 and 5, inclusive. In particular embodiments, m is one or two, and $R^1$ or $R^5$ is a methyl or phenyl group. In other embodiments, $R^2$ is a phenyl, 4-Cl-phenyl, 4-I-phenyl, 4-F-phenyl, 4-nitro-phenyl, 4-phenyl-phenyl, or 4-methoxy-phenyl group. In still other embodiments, $R^3$ and $R^4$ are hydrogen.

In a related aspect, the invention features a compound having the formula:

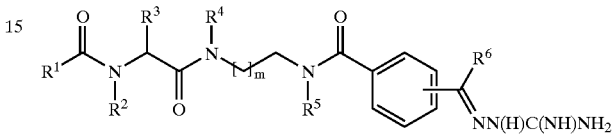

or a derivative or salt thereof. $R^1$ and $R^6$ are independently selected from the group consisting of an alkyl and an aryl group; $R^3$ is hydrogen, an alkyl, or an aryl group. $R^2$, $R^4$, and $R^5$ are independently selected from the group consisting of hydrogen and an alkyl. M is at least one. In other embodiments, m is between 1 and 15, 1 and 10, or 1 and 5, inclusive. In particular embodiments, m is one or two. In other embodiments, $R^1$ or $R^6$ is a methyl or phenyl group. In still other embodiments, wherein $R^3$ is a benzyl, 4-Cl-benzyl, 4-I-benzyl, 4-F-benzyl, 4-nitro-benzyl, 4-phenyl-benzyl, or 4-methoxy-benzyl group phenyl, 4-Cl-phenyl, 4-I-phenyl, 4-F-phenyl, 4-nitro-phenyl, 4-phenyl-phenyl, or 4-methoxy-phenyl group. In still other embodiments, $R^2$, $R^4$, and $R^5$ are hydrogen.

In another aspect, the invention provides a compound having the formula:

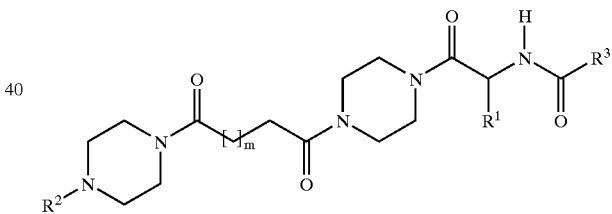

or a derivative or salt thereof. $R^1$ and $R^2$ are independently selected from the group consisting of hydrogen, an alkyl, and an aryl group. $R^3$ is an aryl group. M is at least one. In various embodiments, m is between 1 and 15, 1 and 10, or 1 and 5, inclusive. In other embodiments, m is one or two. In still other embodiments, $R^1$ or $R^2$ is a methyl, isopropyl, or phenyl group. In yet other embodiments, $R^3$ is a phenyl, 4-Cl-phenyl, 4-I-phenyl, 4-F-phenyl, 4-nitro-phenyl, 4-phenyl-phenyl, or 4-methoxy-phenyl group. In various other embodiments, $R^3$ is an aryl group that has a substituent bound to carbon 4 of the aromatic ring.

The compounds of the present invention are useful for the prevention and treatment of a variety of conditions involving ARE-mRNAs or proteins encoded by ARE-mRNAs. Accordingly, the invention features a pharmaceutical composition that includes one or more of the compounds of the present invention in a pharmaceutically acceptable carrier.

A compound described in any of the embodiments of the above aspects of the invention may be used in any of the following clinical applications.

One such method for treating or preventing a condition in a subject involves administering a compound to the subject in an amount sufficient to inhibit secretion of a protein encoded by an ARE-mRNA or modulate regulation of an ARE-mRNA in the subject. The compound has the formula:

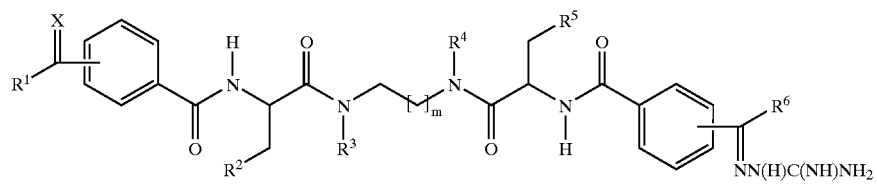

or a derivative or salt thereof. $R^1$ and $R^6$ are independently selected from the group consisting of an alkyl and an aryl group; $R^2$ and $R^5$ are independently selected from the group consisting of hydrogen, an alkyl, and an aryl group; $R^3$ and $R^4$ are independently selected from the group consisting of hydrogen and an alkyl group. X is oxygen or $H_2N(HN)C(H)NN-$; and m is at least one.

In a related aspect, the invention provides another method for treating or preventing a condition in a subject that involves administering a compound to the subject in an amount sufficient to inhibit secretion of a protein encoded by an ARE-mRNA or modulate regulation of an ARE-mRNA in the subject. The compound has the formula:

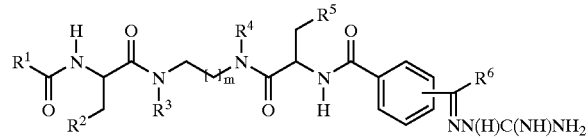

or a derivative or salt thereof. $R^1$ and $R^6$ are independently selected from the group consisting of an alkyl and an aryl group; $R^2$ and $R^5$ are independently selected from the group consisting of hydrogen, an alkyl, and an aryl group. $R^3$ and $R^4$ are independently selected from the group consisting of hydrogen and an alkyl. M is at least one.

In a related aspect, the invention provides yet another method for treating or preventing a condition in a subject that involves administering a compound to the subject in an amount sufficient to inhibit secretion of a protein encoded by an ARE-mRNA or modulate regulation of an ARE-mRNA in the subject. The compound has the formula:

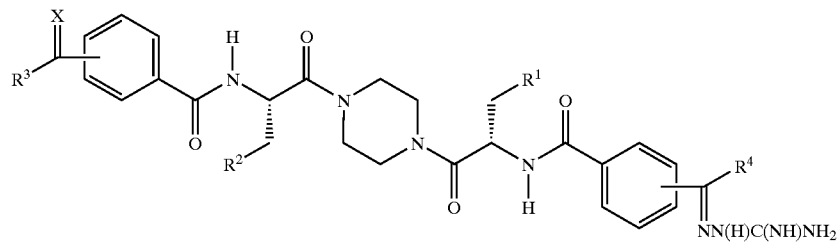

or a derivative or salt thereof. $R^1$ and $R^2$ are independently selected from the group consisting of hydrogen, an alkyl, and an aryl group. $R^3$ and $R^4$ are independently selected from the group consisting of an alkyl and an aryl group. X is oxygen or $H_2N(HN)C(H)NN-$.

In a related aspect, the invention provides still another method for treating or preventing a condition in a subject that involves administering a compound to the subject in an amount sufficient to inhibit secretion of a protein encoded by an ARE-mRNA or modulate regulation of an ARE-mRNA in the subject. The compound has the formula:

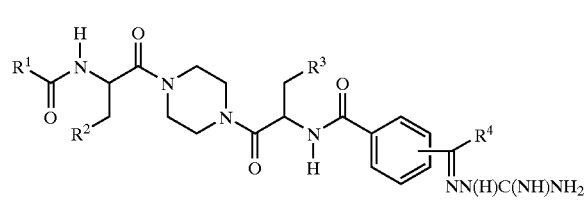

or a derivative or salt thereof. $R^1$ and $R^4$ are independently selected from the group consisting of an alkyl and an aryl group; and $R^2$ and $R^3$ are independently selected from the group consisting of hydrogen, an alkyl, and an aryl group.

In a related aspect, the invention provides another method for treating or preventing a condition in a subject that involves administering a compound to the subject in an amount sufficient to inhibit secretion of a protein encoded by an ARE-mRNA or modulate regulation of an ARE-mRNA in the subject. The compound has the formula:

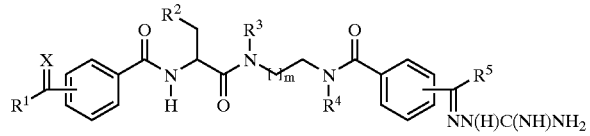

or a derivative or salt thereof. $R^1$ and $R^5$ are independently selected from the group consisting an aryl or alkyl group; $R^2$ is hydrogen, an alkyl, or aryl group; $R^3$ and $R^4$ are independently selected from the group consisting of hydrogen and an alkyl group. X is oxygen or $H_2N(HN)C(H)NN-$; and m is at least one.

In another related aspect, the invention provides a method for treating or preventing a condition in a subject that involves administering a compound to the subject in an amount sufficient to inhibit secretion of a protein encoded by an ARE-mRNA or modulate regulation of an ARE-mRNA in the subject. The compound has the formula:

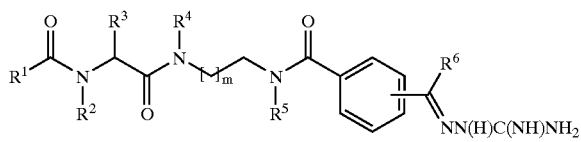

or a derivative or salt thereof. $R^1$ and $R^6$ are independently selected from the group consisting of an alkyl and an aryl group; $R^3$ is hydrogen, an alkyl, and an aryl group. $R^2$, $R^4$, and $R^5$ are independently selected from the group consisting of hydrogen and an alkyl, and m is at least one.

In a related aspect, the invention provides another method for treating or preventing a condition in a subject that involves administering a compound to the subject in an amount sufficient to inhibit secretion of a protein encoded by an ARE-mRNA or modulate regulation of an ARE-mRNA in the subject. The compound has the formula:

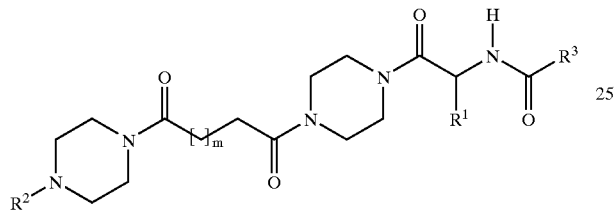

or a derivative or salt thereof. $R^1$ and $R^2$ are independently selected from the group consisting of hydrogen, an alkyl, and an aryl group. $R^3$ is an aryl group, and m is at least one. In various embodiments, $R^3$ is an aryl group that has a substituent bound to carbon 4 of the aromatic ring.

In another aspect, the invention features a method of forming a compound of interest by reacting (a) a first compound having the formula:

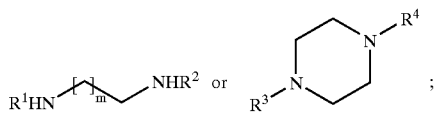

(b) a second compound having the formula:

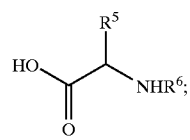

(c) a third compound having the formula:

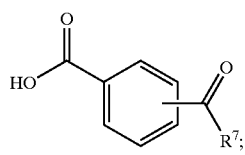

(d) a fourth compound having the formula:

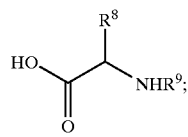

(e) a fifth compound having the formula:

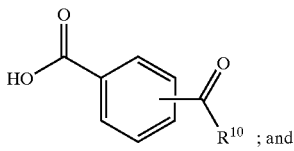; and (f) a sixth compound having the formula:

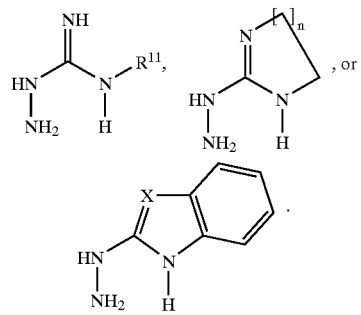

$R^1$ $R^3$, $R^6$ and $R^9$ are each a protecting group. $R^2$ and $R^4$ are independently selected from the group consisting of hydrogen and an alkyl. $R^5$, $R^7$, $R^8$, $R^{10}$, and $R^{11}$ are independently selected from the group consisting of hydrogen, an alkyl, and an aryl group. X is carbon, nitrogen, oxygen, or sulfur; and m and n are at least one. In various embodiments, m or n is between 1 and 15, 1 and 10, or 1 and 5, inclusive. In particular embodiments, m or n is one or two. In other embodiments, $R^5$ or $R^8$ is a benzyl, 4-Cl-benzyl, 4-I-benzyl, 4-F-benzyl, 4-nitro-benzyl, 4-phenyl-benzyl, 4-methoxy-benzyl, 3-acetyl-benzoyl, 4-benzyol-benzoyl, phenyl, 4-Cl-phenyl, 4-I-phenyl, 4-F-phenyl, 4-nitro-phenyl, 4-phenyl-phenyl, or 4-methoxy-phenyl group. In yet other embodiments, $R^2$, $R^4$, or $R^9$ is hydrogen. In particular embodiments, $R^7$ or $R^{10}$ is a methyl or phenyl group. In other embodiments, $R^5$, $R^7$, $R^8$, $R^{10}$, or $R^{11}$ includes, or is modified to include, a protecting group, such as a t-butyloxycarbonyl or benzyloxycarbonyl group. In various embodiments, either one or two sixth compounds are incorporated into the compound of interest. In still other embodiments, the method further includes reacting another sixth compound. In yet other embodiments, the method also includes reacting the second, third, fourth, or fifth compound with a condensing agent to accelerate its rate of reaction with another compound. The method may also include removing a protecting group from an intermediate or from the compound of interest. If desired, other third or fifth compounds that have additional substituents on the benzene ring may be used in this method. Additionally, a first compound having a substituent in place of one or both hydrogens of a methylene group (—$CH_2$—) may be used.

In another aspect, the invention features a method of forming a compound of interest by reacting (a) a first compound having the formula:

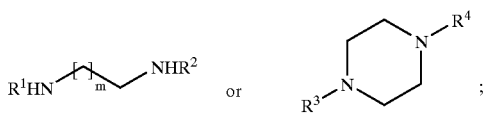

(b) a second compound having the formula:

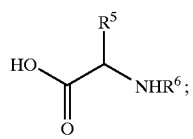

(c) a third compound having the formula:

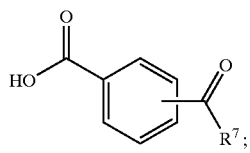

(d) a fourth compound having the formula:

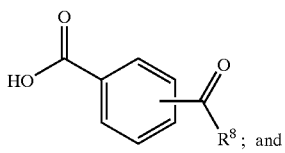

(e) a fifth compound having the formula:

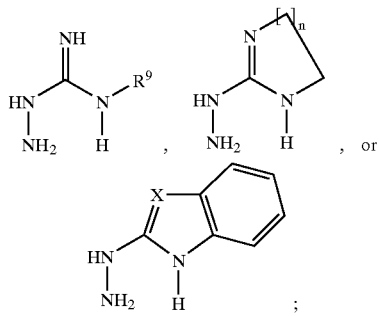

$R^1$, $R^3$, and $R^6$ are each a protecting group. $R^2$ and $R^4$ are independently selected from the group consisting of hydrogen and an alkyl group. $R^5$, $R^7$, $R^8$, and $R^9$ are independently selected from the group consisting of hydrogen, an alkyl, and an aryl group. X is carbon, nitrogen, oxygen, or sulfur; and m and n are at least one. In various embodiments, m is between 1 and 15, 1 and 10, or 1 and 5, inclusive. In particular embodiments, m is one or two. In other embodiments, $R^5$ is a benzyl, 4-Cl-benzyl, 4-I-benzyl, 4-F-benzyl, 4-nitro-benzyl, 4-phenyl-benzyl, 4-methoxy-benzyl, 3-acetyl-benzoyl, 4-benzyol-benzoyl, phenyl, 4-Cl-phenyl, 4-I-phenyl, 4-F-phenyl, 4-nitro-phenyl, 4-phenyl-phenyl, or 4-methoxy-phenyl group. In still other embodiments, $R^2$ or $R^4$ is hydrogen. In particular embodiments, $R^7$ or $R^8$ is a methyl or phenyl group. In other embodiments, $R^5$, $R^7$, $R^8$, or $R^9$ includes, or is modified to include, a protecting group, such as a t-butyloxycarbonyl or benzyloxycarbonyl group. In various embodiments, either one or two fifth compounds are incorporated into the compound of interest. In still other embodiments, the method further includes reacting another fifth compound. In yet other embodiments, the method also includes reacting the second, third, or fourth compound with a condensing agent to accelerate its rate of reaction with another compound. The method may also include removing a protecting group from an intermediate or from the compound of interest. If desired, other third or fourth compounds that have additional substituents on the benzene ring may be used in this method. Additionally, a first compound having a substituent in place of one or both hydrogens of a methylene group (—$CH_2$—) may be used.

In another aspect, the invention features a method of forming a compound of interest by reacting (a) a first compound having the formula:

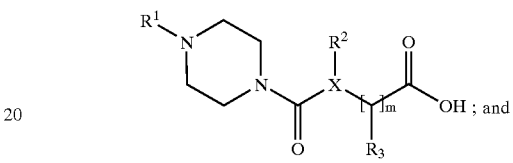

(b) a second compound having the formula:

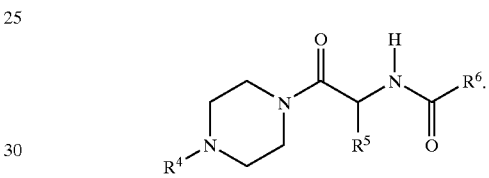

$R^4$ is hydrogen; $R^1$, $R^2$, $R^3$, $R^5$, and $R^6$ are independently selected from the group consisting of hydrogen, an alkyl, and an aryl group. X is carbon or nitrogen, and m is at least one. In various embodiments, m is between 1 and 15, 1 and 10, or 1 and 5, inclusive. In particular embodiments, m is one or two. In other embodiments, $R^1$, $R^2$, $R^3$, or $R^5$ is a benzyl, 4-Cl-benzyl, 4-I-benzyl, 4-F-benzyl, 4-nitro-benzyl, 4-phenyl-benzyl, 4-methoxy-benzyl, 3-acetyl-benzoyl, 4-benzyol-benzoyl, phenyl, 4-Cl-phenyl, 4-I-phenyl, 4-F-phenyl, 4-nitro-phenyl, 4-phenyl-phenyl, or 4-methoxy-phenyl group. In yet other embodiments, $R^6$ is an aryl group, such as a phenyl, 4-Cl-phenyl, 4-I-phenyl, 4-F-phenyl, 4-nitro-phenyl, 4-phenyl-phenyl, or 4-methoxy-phenyl group. In various other embodiments, $R^6$ is an aryl group that has a substituent bound to carbon 4 of the aromatic ring. In other embodiments, $R^1$, $R^2$, $R^3$, $R^5$, or $R^6$ includes, or is modified to include, a protecting group, such as a t-butyloxycarbonyl or benzyloxycarbonyl group. In yet other embodiments, the method also includes reacting the first compound with a condensing agent to accelerate its rate of reaction with the second compound. The method may also include removing a protecting group from the compound of interest.

In various embodiments of any of the aspects of the invention, the alkyl group is a linear or branched saturated hydrocarbon group of 1 to 5, 1 to 10, 1 to 20, 1 to 50, or 1 to 100 carbon atoms; such as a methyl, ethyl, n-propyl, isopropyl, n-butyl, isobutyl, t-butyl, octyl, decyl, or tetradcyl group; or a cycloalkyl group, such as a cyclopentyl or cyclohexyl group. Other suitable alkyl groups include heteroalkyl groups in which one or more carbons have been replaced with another atom, such as nitrogen, sulfur, oxygen, or phosphate. One or more of the hydrogens in an alkyl group may be optionally substituted with a hydroxy, cyano, thio, halo, nitro, amino, or alkoxy group. In other embodiments, the alkyl group is the side-chain of any naturally-occurring or modified L- or D-amino acid with an alkyl or substituted alkyl side-chain (e.g., alanine, beta-alanine, cyclohexylalanine, ethylglycine, valine, norleucine, leucine, norleucine isoleucine, allo-isoleucine, methionine, norvaline, homocysteine, cysteine, threonine, serine, homoserine, or 3-aminobutyric acid).

Desirable aryl groups include monovalent aromatic hydrocarbon radicals consisting of one or more rings in which at least one ring is aromatic in nature, which may optionally be substituted with one of the following substituents: hydroxy, cyano, alkyl, alkoxy, thioalkyl, halo, haloalkyl, hydroxyalkyl, nitro, amino, alkylamino, diakylamino, or acyl. Other suitable aryl groups include heteroaryl groups in which one or more carbons in a ring have been replaced with another atom, such as nitrogen, sulfur, or oxygen. Yet other suitable aryl groups include a phenyl, benzyl, or benzoyl moiety that is either unsubstituted or that contain one or more nitro, halo (e.g., chloro, fluoro, iodo, or bromo), aryl, (e.g., phenyl or benzyl), alkyl, alkoxy (e.g., methoxy), or acyl (e.g. acetyl or benzoyl) substituents. In various embodiments, a substituent is bound to carbon 2, 3, 4, 5, or 6 of one of these moieties. Other suitable aryl groups include benzoyl-NH-benzoyl and groups with fused aromatic rings, such as naphthalene, anthracene, phenanthrene, pyrene, and benzo[a]pyrene. In other embodiments, the aryl group is the side-chain of any naturally-occurring or modified L- or D-amino acid with an aryl or substituted aryl side-chain (e.g., phenylalanine, homophenylalanine, 2-napthylalanine, tyrosine, tryptophan, or tetrahydroisoquinoline-1-carboxylic acid).

Suitable alkoxy groups have the formula —OR, and suitable acyl groups have the formula —C(O)R, wherein R is an alkyl or aryl group as defined above. Examples of alkoxy groups include, but are not limited to, methoxy, ethoxy, and isopropoxy groups. Examples of acyl groups include acetyl and benzoyl groups.

It is also noted that the acyl or guanylhydrozone substituents on the benzene rings in any of the structures shown above (i.e, the RC(O)— or RC[NN(H)C(NH)NH$_2$]— groups) may be bound to any carbon in the ring, such as carbon 2, 3, 4, 5, or 6. Additionally, the benzene rings may be modified to contain other substituents, such as a nitro, halo, aryl, alkyl, alkoxy, or acyl substituent.

In an embodiment of any one of the aspects of the invention, the compound is in a pharmaceutically acceptable carrier. Suitable carriers include, but are not limited to, saline, buffered saline, dextrose, water, glycerol, ethanol, and combinations thereof. The composition can be adapted for the mode of administration and is typically in the form of a pill, tablet, capsule, spray, powder, or liquid.

In embodiments of any of the above methods of the invention, the ARE-mRNA is an ARE-mRNA molecule identified by Bakheet et al. (supra), such as TNFα, an interleukin family member, an interferon family member, cyclooxygenase-1, or cyclooxygenase-2. Other ARE-mRNAs are listed in FIGS. 4–7. In other embodiments, the protein is encoded by any of the ARE-mRNAs identified by Bakheet et al. (supra) (FIGS. 4–7). The condition that is treated or prevented in the clinical applications of the invention may include any condition associated with an ARE-mRNA or a protein encoded by an ARE-mRNA. In various embodiments, the condition is inflammation, fever, arthritis, septic shock, blood clot, stroke, acute respiratory distress syndrome, cachexia, or an autoimmune disease. In another embodiment, administration is oral or intravenous. In yet another embodiment, the subject is a mammal, for example, a human, cow, goat, horse, or mouse. In still other embodiments, a compound of the invention is effective in at least 20, 40, 60, 80, or 90% of the subjects having a condition or an increased risk for a condition. By "effective" is meant ablates, reduces, or stabilizes symptoms in a subject suffering from the condition, prevents the onset of symptoms in a subject at risk for the condition, or results in a later age-at-onset of symptoms in the subject compared to the average age-of-onset for the corresponding untreated subjects.

As used herein, by "ARE-mRNA" is meant an mRNA molecule containing an AU-rich element (ARE). Many ARE-mRNAs have been identified and reported by Bakheet et al. (supra). A list of ARE-mRNAs is available at the ARE Home Page (http://rc.kfshrc.edu.sa/ared/main.htm) which contains a database of human ARE-mRNAs. This database contains five clusters of ARE-mRNAs (http://rc.kfshrc.edu.sa/ared/diversity.htm, FIGS. 5–7). Additional ARE-mRNA molecules may be readily identified by one skilled in the art. For example, the method described by Bakheet et al. (supra) may be used to identify other mRNA molecules that contain the consensus motif WWWUAU-UUAUWWW (SEQ ID NO: 1) with at most one mismatch in each direction of the nucleotides flanking the core UAU-UUAU (SEQ ID NO: 2) pattern.

By "secretion of a protein encoded by an ARE-mRNA" is meant the production of a protein encoded by an ARE-mRNA in a cell and the subsequent secretion of the protein from the cell. Protein production or secretion may be assayed in a number of ways, for example, using a reporter gene assay system, measuring the amount of a protein secreted from a cell, or using protein functional assays (see, for example, Humphreys et al. Cytokine 11:773–782, 1999). An example of a reporter gene assay that may be used to determine the effect of a candidate inhibitor on a step involved in secretion of a protein encoded by an ARE-mRNA is the luciferase assay described herein. Alternatively, a standard Northern blot analysis may be used to measure the amount of ARE-mRNA produced in a cell, or a standard ELISA or Western blot assay may be used to determine the amount of a protein encoded by an ARE-mRNA produced in a cell or secreted from a cell (see, for example, Ausubel et al., Current Protocols in Molecular Biology, John Wiley & Sons, New York, 2000).

By "inhibiting secretion of a protein encoded by an ARE-mRNA" is meant decreasing the amount of a protein encoded by an ARE-mRNA that is secreted by a cell or tissue by administering a candidate inhibitor of secretion of a protein encoded by an ARE-mRNA. Typically, the amount of TNFα secreted by a cell or tissue is compared to that secreted by a control cell or tissue that has not been administered the candidate inhibitor of secretion of a protein encoded by an ARE-mRNA or that has been administered a moderately active inhibitor of secretion of a protein encoded by an ARE-mRNA. Alternatively, the amount of a protein encoded by an ARE-mRNA that is secreted by a cell or tissue after administration of a candidate inhibitor may be compared to that secreted by the cell or tissue before administration of the candidate inhibitor. In various desirable embodiments, secretion of a protein encoded by an ARE-mRNA is decreased by at least 10, 30, 40, 50, 75, 90, or 95% relative to a control cell receiving vehicle only (for example, DMSO or saline). In other embodiments, a compound that inhibits secretion of a protein encoded by an ARE-mRNA reduces or stabilizes the level of ARE-mRNA or the encoded protein, the half-life of ARE-mRNA or the encoded protein, the processing of ARE-mRNA, the binding of ARE-mRNA or the encoded protein to a receptor or to another molecule, or the rate of passive or active diffusion of a protein encoded by an ARE-mRNA out of a cell, as measured using the cell-based assays described herein or in any other standard assay (see, for example, Ausubel et al., supra). If desired, any of the cell-based assays may be performed in the presence of lipopolysaccharide (LPS) or any other activator of TNFα biosynthesis or secretion to increase the level of TNFα secretion, thereby facilitating the detection of a decrease in TNFα secretion caused by a candidate compound. The effect of a compound of the invention on the level of secretion of a protein encoded by an ARE-mRNA in a subject may be determined, if desired, by performing a routine ELISA assay on a serum sample from the subject to determine the amount of the protein that is present.

By a "test compound" or "candidate compound" is meant a naturally-occurring or artificially-derived chemical that is assayed for its ability to modulate secretion of a protein encoded by an ARE-mRNA or modulate ARE-mRNA regulation in one of the assay methods described herein or in any other appropriate assay.

By "treating" is meant subjecting an animal, tissue, cell, cell lysate, cell extract, or molecule to a compound that modulates secretion of a protein encoded by an ARE-mRNA or modulates ARE-mRNA regulation.

By "condition" is meant a state of being or feeling. Conditions include, but are not limited to, inflammation, inflammatory diseases, arthritis, autoimmune diseases, septic shock, blood clots, and injuries.

By "inflammation" is meant an immune reaction that occurs when immunologically competent cells are activated in response to tissue damage, such as damage resulting from trauma, lack of blood supply, hemorrhage, foreign organisms, antigens, chemicals, irritants, allergens, electricity, heat, cold, microorganisms, surgical operations, or ionizing radiation. Examples of possible antigens include viral, bacterial, protozoal, and fungal proteins, carbohydrates, and lipids. Inflammation may be characterized by redness, swelling, heat, or pain, including hypersensitivity at the site of injury (primary hyperalgesia), hypersensitivity in neighboring non-injured tissue (secondary hyperalgesia), and diffuse pain. Additionally, any known animal model for inflammation may be used to test the ability of a compound of the present invention to prevent, stabilize, or treat inflammation. Suitable models of inflammatory pain include unilateral injection of formalin, carrageenan, or complete Freund's adjuvant (CFA) into the hindpaw of rodent, such as a rat or mouse (Honor et al., J. Neruosci 19:7670–7678, 1999). For a model of chronic inflammatory pain, CFA may be used to induce arthritis in mice or rats (Honor et al., supra; Vieira et al., Eur. J. Pharmacol. 407:109–116, 2000).

By "amount sufficient to inhibit secretion of a protein encoded by an ARE-mRNA" is meant an amount of a compound that decreases secretion of a protein encoded by an ARE-mRNA when administered to a subject. In desirable embodiments, the decrease in secretion of a protein encoded by an ARE-mRNA is at least 10%, 30%, 40%, 50%, 75%, or 90% greater in a treated subject than in an untreated, control subject. In other embodiments, the amount of the protein encoded by an ARE-mRNA that is secreted is at least 2, 5, 10, or 20-fold lower in a treated subject than in the same subject prior to the administration of the inhibitor or than in an untreated, control subject.

By "amount sufficient to modulate regulation of an ARE-mRNA" is an amount of a compound that modulates regulation of an ARE-mRNA when administered to a subject. In desirable embodiments, the rate of mRNA degradation, mRNA processing, or mRNA translation in a treated subject is less than 90, 80, 70, 60, 50, 30, or 10% of the corresponding rate in an untreated, control subject. In other desirable embodiments, the amount of an ARE-mRNA or a protein encoded by an ARE-mRNA is at least 2, 5, 10, or 20-fold lower in a treated subject than in the same subject prior to the administration of the inhibitor or than in an untreated, control subject. In a particularly desirable assay, regulation of an ARE-mRNA is measured by determining the decrease in the amount of the encoded protein that is effected by the administration of a compound to a subject.

By a "derivative" is meant a structural derivative having a chemical modification that enhances the bioavailability, solubility, stability, or potency of a compound in vivo or in vitro or that reduces the toxicity of a compound in vivo or in vitro. In other desirable embodiments, the inhibition of secretion of a protein encoded by an ARE-mRNA by the derivative is at least 10%, 30%, 40%, 50%, 75%, 90%, 95%, or 100% of that by the compound from which the derivative was derived. Such modifications are known to those skilled in the field of medicinal chemistry.

By "condensing agent" is meant a compound that accelerates the reaction between an amine and a carboxylic acid. The condensing agent reacts with the carboxylic acid such that the hydroxyl group of the carboxylic acid is converted into a better leaving group for the nucleophilic substitution reaction between this activated carboxylic acid and the amine. Condensing agents are well known in the art of organic synthesis.

Other features and advantages of the invention will be apparent from the following detailed description.

BRIEF DESCRIPTION OF THE DRAWINGS

FIG. 4 is a list of ARE-mRNAs using by Bakheet et al. (supra) in generating the ARE consensus motif (http://rc.kfshrc.edu.sa/ared/methodology.htm).

FIG. 5 is a list of ARE-mRNAs from the human ARE-mRNA database (Bakheet et al. (supra); http://rc.kfshrc.edu.sa/ared/diversity.htm). These ARE-mRNAs were clustered into five groups containing five, four, three, two, or one pentameric repeat within the ARE pattern (SEQ ID NOS: 3–7), respectively. FIG. 5 lists the mRNAs in Clusters 1, 2, and 3. The mRNAs in Cluster 4 are listed in FIG. 6, and the mRNAs in Cluster 5 are listed in FIG. 7.

FIG. 6 is a list of ARE-mRNAs from Cluster 4 of the human ARE-mRNA database (Bakheet et al. (supra); http://rc.kfshrc.edu.sa/ARED/group4cluster.txt).

FIG. 7 is a list of ARE-mRNAs from Cluster 5 of the human ARE-mRNA database (Bakheet et al. (supra); http://rc.kfshrc.edu.sa/ARED/group5cluster.txt).

DETAILED DESCRIPTION OF THE INVENTION

Figure 1:
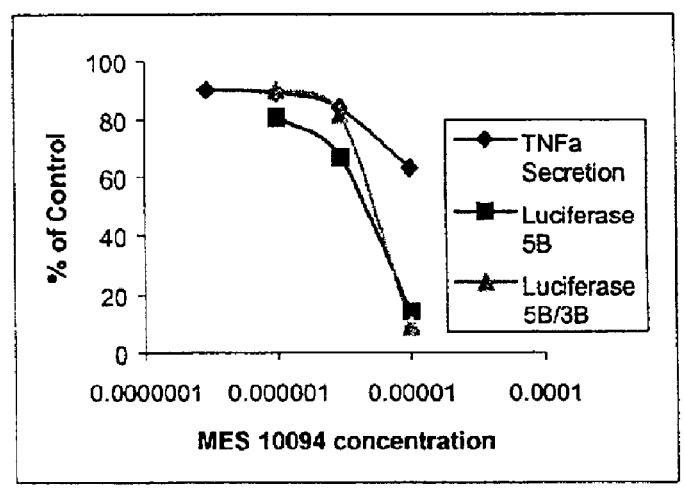
FIG. 1 is a graph showing the effect of MES 10094 on luciferase activity.

We have identified a variety of compounds that inhibit TNFα secretion. These compounds are useful for clinical applications involving the treatment or prevention of diseases or injuries involving TNFα. Because of the high level of sequence identity between the ARE element in the 3'UTR of TNFα and the ARE element in other ARE-mRNAs, these compounds may also be used to inhibit secretion of other proteins encoded by ARE-mRNAs or to modulate the regulation of other ARE-mRNAs.

Some of the inhibitors of TNFα secretion that we identified are mono or bisguanylhydrazones having the formula:

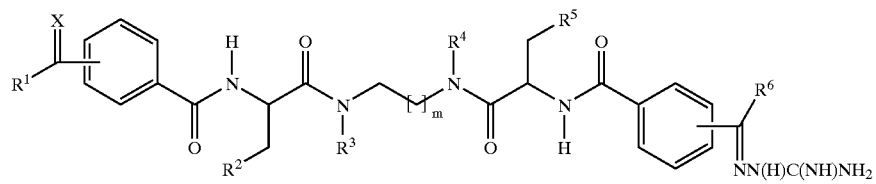

or a derivative or salt thereof. $R^1$ and $R^6$ are independently selected from the group consisting of an alkyl and an aryl group; $R^2$ and $R^5$ are independently selected from the group consisting of hydrogen, an alkyl, and an aryl group; and $R^3$ and $R^4$ are independently selected from the group consisting of hydrogen and an alkyl group. X is oxygen or $H_2N(HN)C(H)NN$—, and m is at least one.

Other inhibitors of TNFα secretion are monoguanylhydrazones having the formula:

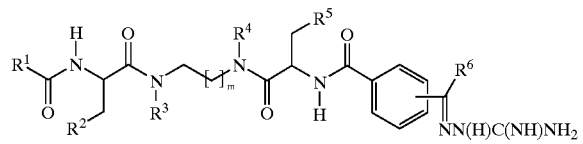

or a derivative or salt thereof. $R^1$ and $R^6$ are independently selected from the group consisting of an alkyl and an aryl group; $R^2$ and $R^5$ are independently selected from the group consisting of hydrogen, an alkyl, and an aryl group; $R^3$ and $R^4$ are independently selected from the group consisting of hydrogen and an alkyl. M is at least one.

Several mono or bisguanylhydrazones with a piperazine linker were also inhibitors of TNFα secretion. These compounds have the formula:

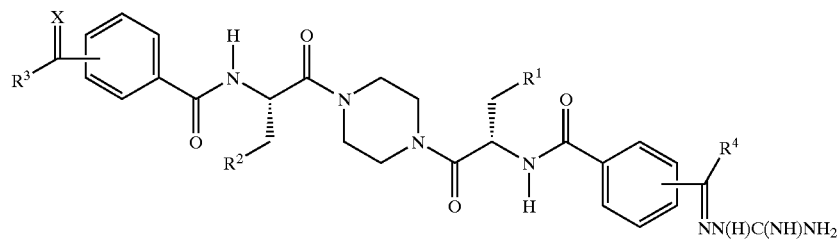

or a derivative or salt thereof. $R^1$ and $R^2$ are independently selected from the group consisting of hydrogen, an alkyl, and an aryl group; $R^3$ and $R^4$ are independently selected from the group consisting of an alkyl and an aryl group. X is oxygen or $H_2N(HN)C(H)NN$—. In various embodiments, $R^3$ or $R^4$ is a phenyl or methyl group. In other embodiments, $R^1$ or $R^2$ is a phenyl, 4-Cl-phenyl, 4-I-phenyl, 4-F-phenyl, 4-nitro-phenyl, 4-phenyl-phenyl, or 4-methoxy-phenyl group. In still other embodiments, $R^1$ is a phenyl group and $R^2$ is an isopropyl group, or $R^1$ is an isopropyl group and $R^2$ is a phenyl group.

Additional inhibitory, monoguanylhydrazone compounds with a piperazine linker have the formula:

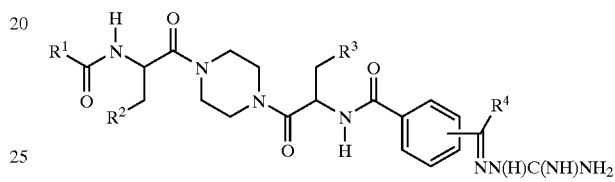

or a derivative or salt thereof. $R^1$ and $R^4$ are independently selected from the group consisting of an alkyl or an aryl group. $R^2$ and $R^3$ are independently selected from the group consisting of hydrogen, an alkyl, and an aryl group.

Additional mono or bisguanylhydrazones that inhibited TNFα secretion have the formula:

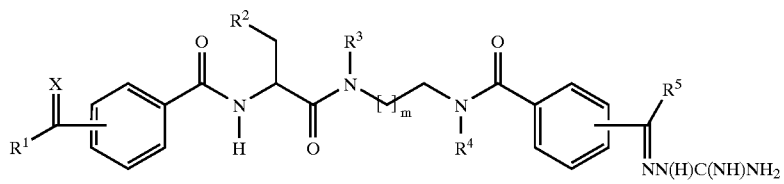

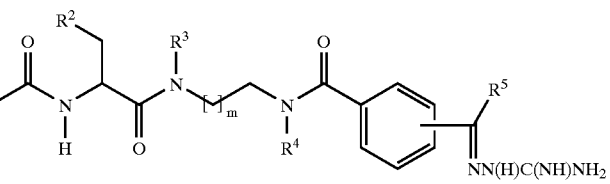

or a derivative or salt thereof. $R^1$ and $R^5$ are independently selected from the group consisting an aryl or alkyl group; $R^2$ is hydrogen, an alkyl, or aryl group. $R^3$ and $R^4$ are independently selected from the group consisting of hydrogen and an alkyl group. X is oxygen or $H_2N(HN)C(H)NN—$; and m is at least one.

Related monoguanylhydrazones that also inhibited TNFα secretion have the formula:

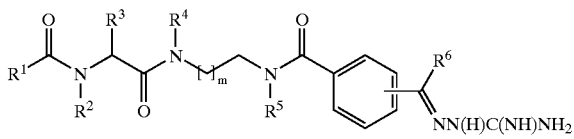

or a derivative or salt thereof. $R^1$ and $R^6$ are independently selected from the group consisting of an alkyl and an aryl group; $R^3$ is hydrogen, an alkyl, or an aryl group. $R^2$, $R^4$, and $R^5$ are independently selected from the group consisting of hydrogen and an alkyl. M is at least one.

In addition to the guanylhydrazone compounds described above, compounds containing a N-phenyl-4-piperazinyl succinate group also inhibited TNFα secretion. These compounds have the formula:

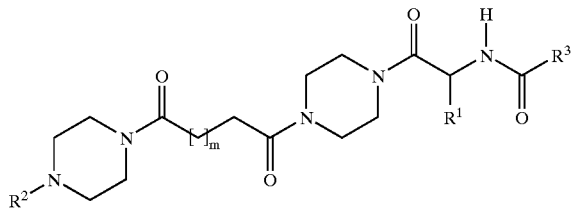

or a derivative or salt thereof. $R^1$, $R^2$, and $R^3$ are independently selected from the group consisting of hydrogen, an alkyl, and an aryl group. M is at least one. In various embodiments, m is between 1 and 15, 1 and 10, or 1 and 5, inclusive.

The ability of these compounds to inhibit TNFα secretion was confirmed in a standard ELISA assay that detected TNFα secreted by cells into the media (described further in Example 1). Additionally, the specificity of the compounds for inhibition of TNFα secretion was tested by comparing luciferase activity in cells expressing luciferase fused to the 3'UTR of TNFα to luciferase activity in control cells expressing luciferase without the heterologous 3'UTR of TNFα (Example 1).

Therapy

A compound identified as capable of inhibiting secretion of a protein encoded by an ARE-mRNA or modulating regulation of an ARE-mRNA using any of the methods described herein may be administered to humans, domestic pets, livestock, or other animals with a pharmaceutically acceptable diluent, carrier, or excipient, in unit dosage form.

The compound be optionally may administered as a pharmaceutically acceptable salt, such as a non-toxic acid addition salt or metal complex that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

The chemical compounds for use in such therapies may be produced and isolated as described herein or by any standard technique known to those in the field of medicinal chemistry. Conventional pharmaceutical practice may be employed to provide suitable formulations or compositions to administer the identified compound to patients suffering from a condition or at increased for a condition involving secreted TNFα. Administration may begin before or after the patient is symptomatic.

Any appropriate route of administration may be employed. For example, the therapy may be administered either directly to the site of inflammation (for example, by injection) or systemically (for example, by any conventional administration technique). Administration of the compound may also be oral, topical parenteral, intravenous, intraarterial, subcutaneous, intramuscular, intracranial, intraorbital, ophthalmalic, intraventricular, intracapsular, intraspinal, intracisternal, intraperitoneal, or intranasal. Alternatively, the compound may be administered as part of a suppository. Therapeutic formulations may be in the form of liquid solutions or suspensions; for oral administration, formulations may be in the form of tablets or capsules; and for intranasal formulations, in the form of powders, nasal drops, or aerosols. The dosage of the therapeutic compounds in a pharmaceutically acceptable formulation depends on a number of factors, including the size and health of the individual patient. The dosage to deliver may be determined by one skilled in the art.

Methods well known in the art for making formulations are found, for example, in "Remington: The Science and Practice of Pharmacy" ((19th ed.) ed. A. R. Gennaro A R., 1995, Mack Publishing Company, Easton, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds that decreases TNFα secretion include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a compound identified according to the methods described above, may be combined with more traditional therapies for a disease characterized by inflammation, such as nonsteroidal anti-inflammatory drugs, or for a procoagulant condition, such as an anticoagulant.

The following examples are provided to illustrate the invention. These examples should not be construed as limiting.

EXAMPLE 1

In Vivo Screening of Candidate Inhibitors of TNFα Secretion

Compounds that inhibit TNFα secretion may be purified or substantially purified, or may be one component of a mixture of compounds, such as a pool of chemical compounds. When assaying of a mixture of compounds, inhibition of TNFα secretion is tested using progressively smaller subsets of the compound pool (e.g., produced by standard purification techniques such as HPLC or FPLC) until a single compound or minimal number of effective compounds is demonstrated to inhibit TNFα secretion. A molecule that inhibits TNFα secretion is considered particularly useful as a therapeutic to decrease TNFα secretion in a patient with a condition in which deleterious TNFα secretion occurs, such as an inflammatory condition, arthritis, an autoimmune disease, fever, or stroke.

The candidate compounds were tested in a high-throughput, cell-based luciferase reporter assay. For this assay, a commercially available mouse macrophage Raw 264.7 cell line was stably transfected with a construct containing the CMV promoter operably linked to the luciferase gene which was modified using standard molecular biology techniques to contain the entire 3' UTR of the TNFα gene. This 3' UTR is important for the stability and translation of TNFα in cells. To control for effects of candidate compounds that are not specific for TNFα, a control cell line, called "3B," was generated by stably transfecting the 264.7 cell line with a commercially available construct containing the luciferase gene (without the addition of the heterologous 3' UTR of the TNFα gene) under the regulation of the CMV promoter.

Both the 3B and 5B cell lines were incubated in the presence of 10 μM of a candidate compound for one hour. Then, lipopolysaccharide (LPS) was added to stimulate TNFα secretion. Luciferase activity was measured by determining the luminescence intensity due to the reaction of lucifern, ATP, $Mg^{2+}$, and molecular $O_2$ (see, for example, Ausubel et al., supra). The luciferase activity in a cell incubated with a candidate compound was reported as a percentage of the luciferase activity for the corresponding cell incubated with DMSO vehicle only.

After correction for any effect caused by the administration of the DMSO only vehicle control, the effect of a candidate compound on luciferase activity in the 3B control cell line represents the global effect of the compound on any step required for expression or activity of luciferase protein, such as luciferase gene transcription, mRNA processing, mRNA stability, translation, protein stability, or enzymatic activity. Thus, in desirable embodiments, a candidate compound that decreases luciferase activity in the 5B cell line which contains the 3' UTR of the qTNFα gene has little or no effect on luciferase activity in the control 3B cell line which does not contain the 3' UTR of the TNFα gene. Such a result suggests that the effect of the candidate compound is predominantly associated with TNFα rather than a global effect on any step required for expression or activity of a protein. In this case, the luciferase activity in the 5B cell line treated with the DMSO vehicle control is similar to the luciferase activity in the control 3B cell line treated with the candidate compound. Thus, the response of the 5B cell line (as a percent of the DMSO control) and the ratio of the luciferase activity in the 5B cell line (as a percent of the DMSO control) to the luciferase activity in the control 3B cell line (as a percent of the DMSO control) are similar. In desirable embodiments, the response of the 5B cell line and the 5B/3B ratio differ by less than 50, 40, 30, 20, 10, or 5%.

For the identification of candidate compounds that modulate the regulation of other ARE-mRNAs, the above luciferase assay may be performed using the heterologous 3'UTR of an ARE-mRNA of interest instead of the 3'UTR of TNFα. The polynucleotide sequences of many ARE-mRNAs are publicly available (see, for example, Bakheet et al., supra). Thus, standard molecular biology techniques may be used to add the 3'UTR of an ARE-mRNA of interest to the luciferase gene, as described above.

The ability of candidate compounds to reduce the amount of secreted TNFα was also directly tested using an ELISA assay. For this assay, cells were incubated with 10 μM candidate compound for one hour, and then LPS was added. A standard ELISA analysis was used to measure the amount of TNFα secreted into the media (see, for example, Ausubel et al., supra). The effect of a candidate compound on TNFα secretion in this assay is reported in the following tables as a percentage of the amount of TNFα secreted by a control cell that was administered a DMSO vehicle control only.

To determine which candidate compounds inhibit the secretion of other proteins encoded by ARE-mRNAs, the above ELISA assay may be performed using an antibody that is reactive with the protein of interest. Optionally, the cells may be treated with a compound that activates secretion of the protein of interest to facilitate the detection of candidate compounds that inhibit this secretion.

Chemical compounds that are found by the methods described above to effectively inhibit secretion of a protein encoded by an ARE-mRNA or to modulate regulation of ARE-mRNA in an in vitro or cell-based system may be tested further in animal models (such as those described in Examples 11 and 12). Particularly useful animal models include mouse and rat models of inflammation (see, for example, Kerland et al., Clin. Exp. Immunol. 115:32–41, 1999; and U.S. Pat. No. 6,022,900, incorporated herein by reference). Compounds that demonstrate an ability to decrease TNFα secretion in animal models may be used as therapeutics in humans to prevent, stabilize, or reduce TNFα secretion.

EXAMPLE 2

Characterization of Identified Inhibitors of TNFα Secretion

The general structure of the members of an initial guanylhydrazone library is listed below.

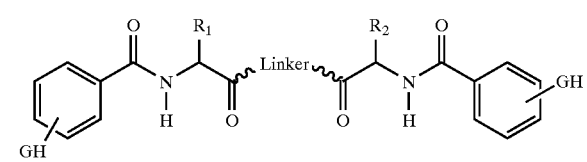

General Structure for Initial Library Members

These compounds were initially tested in the cell-based assays described above as crude synthetic samples containing a predictable number of isomers of mono and bisguanylhydrazones.

The ability of conformationally undefined guanylhydrazones to inhibit TNFα secretion was demonstrated by the inhibitory activity of MES 10094, shown below.

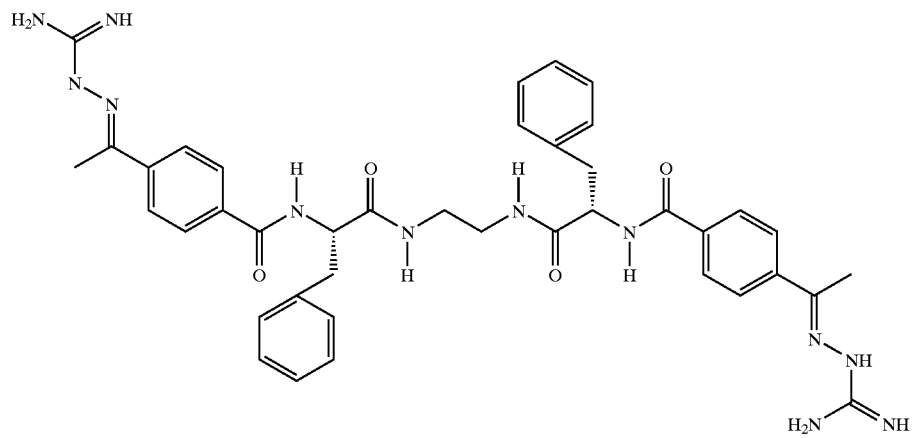

MES 10094

MES 10094 strongly inhibited luciferase activity in the 5B cell line and only weakly inhibited luciferase activity in the 3B cell line, producing a close correlation of the 5B and 5B/3B data (FIG. 1). This result suggests that MES 10094 effects expression or stability of the 3' UTR of TNFα. Additionally, MES 10094 inhibited TNFα secretion after LPS stimulation. HPLC analysis of MES 11094 revealed that this compounds exists as only one bisguanylhydrazone isomer.

Other candidate compounds containing a 1,3-proplyenediamine linker (denoted "Pr") or a conformationally restrained piperazine linker (denoted "P") between the two ends of the molecules were also tested in these assays (Table 1).

The results of the luciferase assay indicated that MES 11461, 11462, 11405, 11408, 11465, 11411, 11561, and 11562 decrease TNFα secretion, with MES 11461, 11462, and 11561 producing the greatest inhibition. Many of the compounds were further tested by assaying directly for TNFα polypeptide secretion. MES 11461, 11462, 11405, 11452, 11561, and 11562 decreased the amount of secreted TNFα. In addition, reversal of the interior component of MES 11462 (MES 11405) resulted in a molecule that displayed TNFα secretion inhibitory activity similar to that of MES 11461 and MES 11462.

HPLC analysis of MES 11461 indicated that the sample was a mixture of four bisguanylhydrazone isomers (MES 10164, 10165, 10166, and 10167, described further below) and probably four monoguanylhydrazone isomers, although

TABLE 1

Inhibition of TNFα Secretion by Guanylhydrazone Library Members

| MES# (10 μM) | GH | $R_1$ | Linker | $R_2$ | GH | Luciferase 5B (% of DMSO control) | Luciferase 5B/3B (% of DMSO control 5B)/ (% of DMSO control 3B) | TNFα Secretion (% of DMSO control) |
|---|---|---|---|---|---|---|---|---|
| 11461 | 4Bn | Phe | P | Leu | 4Bn | 28 | 31 | 44 |
| 11462 | 4Bn | Phe | P | Leu | 3Ac | 24 | 37 | 55 |
| 11405 | 3Ac | Phe | P | Leu | 4Bn | 39 | 49 | 55 |
| 11408 | 4Bn | Leu | P | Leu | 3Ac | 59 | 54 | |
| 11465 | 4Bn | Phe | P | Ala | 3Ac | 72 | 71 | |
| 11452 | 4Ac | Phe | P | Leu | 3Ac | 13 | 50 | 88 |
| 11411 | 4Bn | Ala | Pr | Leu | 3Ac | 65 | 71 | |
| 11561 | 4Bn | Phe | Pr | Leu | 4Bn | 24 | 26 | 41 |
| 11562 | 4Bn | Phe | Pr | Leu | 3Ac | 44 | 38 | 50 |

Figure 2:
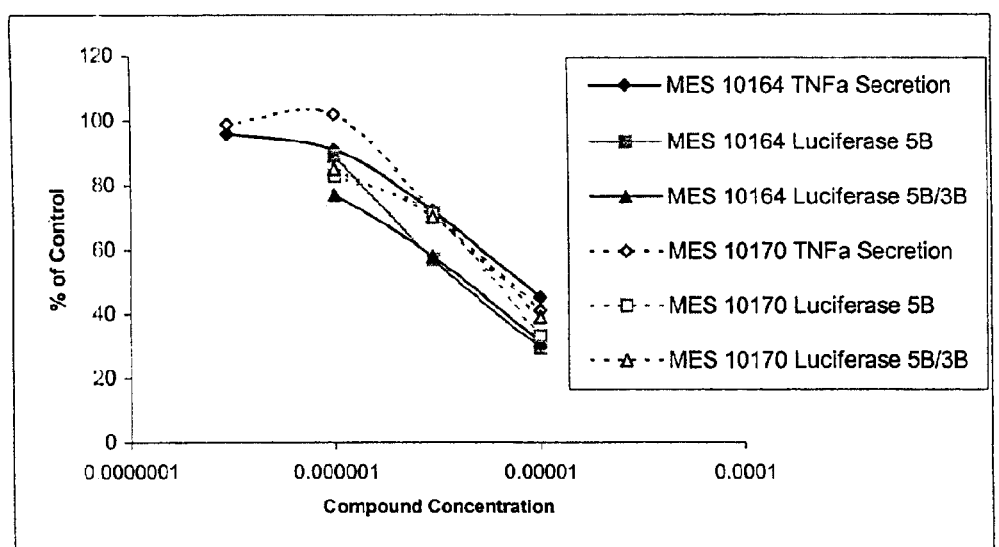
FIG. 2 is a graph showing the effect of MES 10164 or MES 10170 on luciferase activity and TNFα secretion.

For the columns of Table 1 labeled "$R_1$" and "$R_2$," the amino acids listed (i.e., Phe, Leu, and Ala) represent the side chains that were used as the "$R_1$" or "$R_2$," group illustrated in the general structure for initial library members shown above. The "GH" column lists the type of guanylhydrazone present in the compound; for example, "4Bn" refers to a 4-benzoyl-benzamide derived guanylhydrazone moiety, and "3Ac" refers to a 3-acetyl-benzamide derived guanylhydrazone moiety. In subsequent tables, "4-Bn Bn" denotes a 4-benzoyl-benzoyl group (i.e., $C_6H_5$—C(O)—$C_6H_4$—C(O)—). "Ac" denotes an acetyl group (i.e., $CH_3C(O)$—); "Ph" denotes a phenyl group (i.e, $C_6H_5$), and "Bzl" denotes a benzyl group (i.e, $C_6H_5$—$CH_3$—).

only three fractions were observed (MES 10168, 10169, and 10170). These data are consistent with each 4-benzoylbenzamide derived guanylhydrazone existing in either an E or Z configuration relative to the central core. Similarly, MES 11462 was shown to comprise two bisguanylhydrazones (MES 10171 and 10172) and one monoguanylhydrazone (MES 10173). Separation of the components of these mixtures by HPLC and characterization by $^1$H NMR and mass spectrometry confirmed the nature of the individual components. Analysis of the ability of these individual compounds to inhibit TNFα secretion is presented in Tables 2 and 3 and FIG. 2.

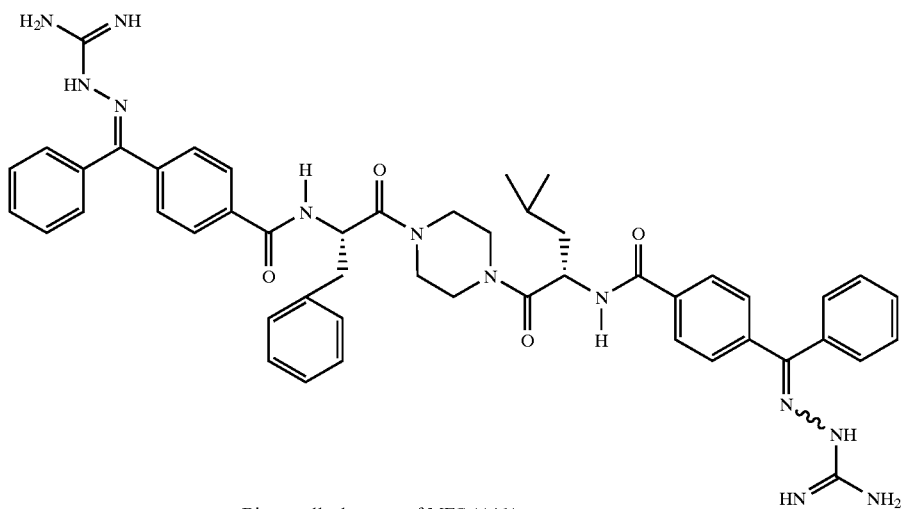

Bisguanylhydrazones of MES 11461

TABLE 2

Inhibition of TNFα Secretion by Components of MES 11461

| MES# 10 μM | Luciferase 5B (% of DMSO control) | Luciferase 5B/3B (% of DMSO control 5B)/(% of DMSO control 3B) | TNFα Secretion (% of DMSO control |
|---|---|---|---|
| MES 11461 | 28 | 31 | 44 |
| MES 10164 | 29 | 31 | 45 |
| MES 10165 | 37 | 63 | 36 |
| MES 10166 | 37 | 43 | 41 |
| MES 10167 | 43 | 42 | 35 |
| MES 10168 | 104 | 127 | 35 |
| MES 10169 | 57 | 59 | 51 |
| MES 10170 | 33 | 39 | 41 |

Figure 3:
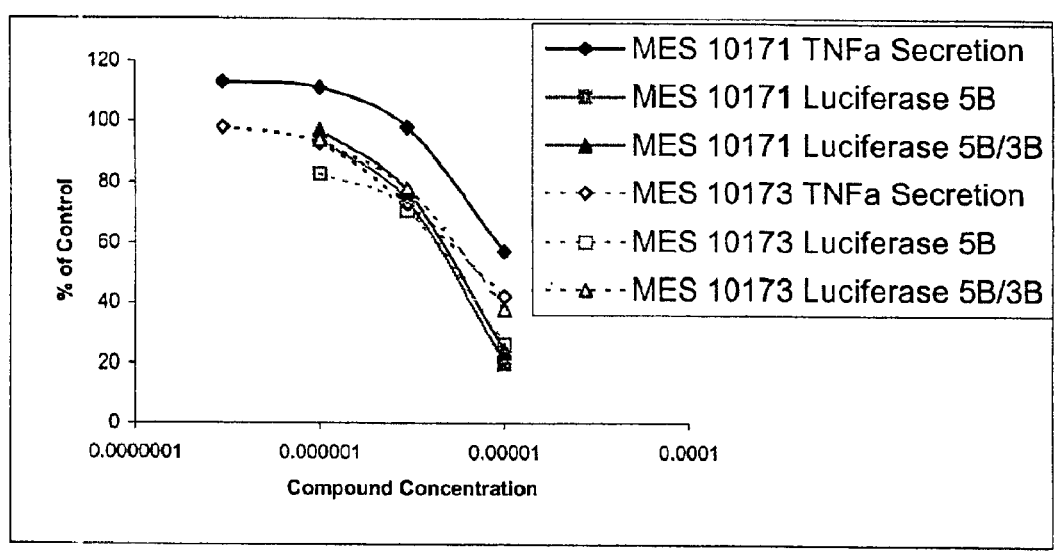
FIG. 3 is a graph showing the effect of MES 10171 or MES 10173 on luciferase activity.

As shown in Table 2, each bisguanylhydrazone component of MES 11461 (MES 10164, 10165, 10166, and 10167) inhibited TNFα secretion, based on the luciferase reporter assay and direct measurement of TNFα secretion. Both MES 10169 and 10170 (an inseparable mixture of the two Z-monoguanylhydrazone species) inhibited luciferase activity in the 5B cell line and had minimal effect on the 3B cell line (FIG. 3). In addition, each of the monoguanylhydrazone components of MES 11461 reduced the amount of secreted TNFα in the direct TNFα secretion assay.

A similar trend was observed for the components of MES 11462 (Table 3). Based on the two cell-based assays, all of the components of MES 11462 inhibit TNFα secretion.

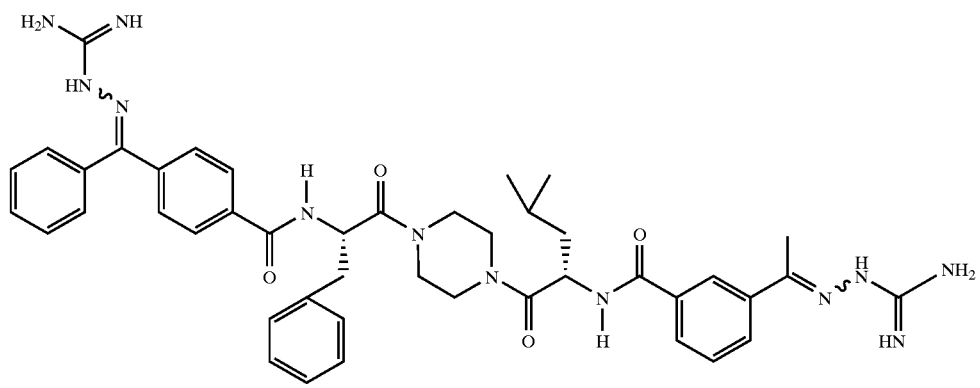

Bisguanylhydrazones of MES 11462

TABLE 3

Inhibition of TNFα Secretion by Components of MES 11462

| 10 μM | Luciferase 5B (% of DMSO control) | Luciferase 5B/3B (% of DMSO control 5B)/(% of DMSO control 3B) | TNFα Secretion (% of DMSO control) |
|---|---|---|---|
| MES 11462 | 24 | 37 | 55 |
| MES 10171 | 20 | 24 | 57 |
| MES 10172 | 38 | 49 | 60 |
| MES 10173 | 26 | 38 | 42 |

EXAMPLE 3

Analogs of MES Library Members

A series of modifications of the MES library members were prepared. These modifications were divided into three groups: (i) amino acid analogs of the guanylhydrazone library members, (ii) a series of analogs of the monoguanylhydrazones, and (iii) a series of N-phenyl-4-piperazinyl succinate derivatives.

Amino Acid Analogs

Several analogs of MES 11461 and 11462 were prepared by independently varying the Phe and Leu residues in these compounds. The inhibitory activity of these analogs in the cell-based assays is reported in Tables 4–7. In these tables, the "Modification" column lists the groups that were used to replace either Phe or Leu in MES 11461 or MES 11462. "Homo Phe" denotes homophenylalanine; "2-Nal" denotes 2-napthylalanine; "Tic" denotes tetrahydroisoquinoline-1-carboxylic acid, and "Chx" denotes cyclohexylalanine.

Within the Phe modifications of MES 11461, all of the analogs inhibited TNFα secretion, based on their activity in the luciferase assay and the direct assay for TNFα secretion (Table 4). Moreover, a modification of the Leu residue of MES 11461, the norleucine analog, also had inhibitory activity (Table 5).

TABLE 4

Modifications of the Phe residue of MES 11461

| 10 μM | Modification | Luciferase 5B (% of DMSO control) | Luciferase 5B/3B (% of DMSO control 5B)/(% of DMSO control 3B) | TNFα Secretion (% of DMSO control) |
|---|---|---|---|---|
| MES 11461 | — | 28 | 31 | 44 |
| MES 10191 | 1-Nal | 46 | 86 | 22 |
| MES 10192 | 4-Cl Phe | 37 | 47 | 17 |
| MES 10193 | 4-Ph Phe | 23 | 38 | 20 |
| MES 10194 | homo Phe | 34 | 49 | 22 |
| MES 10195 | 2-Nal | 36 | 82 | 33 |
| MES 10196 | Tic | 45 | 51 | 35 |

TABLE 4-continued

Modifications of the Phe residue of MES 11461

| 10 μM | Modification | Luciferase 5B (% of DMSO control) | Luciferase 5B/3B (% of DMSO control 5B)/(% of DMSO control 3B) | TNFα Secretion (% of DMSO control) |
|---|---|---|---|---|
| MES 10236 | 4-F Phe | 18 | 25 | 34 |
| MES 10237 | 4-MeO Phe | 20 | 27 | 39 |
| MES 10238 | Chx | 32 | 78 | 23 |

TABLE 5

Modifications of the Leu residue of MES 11461

| 10 μM | Modification | Luciferase 5B (% of DMSO control) | Luciferase 5B/3B (% of DMSO control 5B)/(% of DMSO control 3B) | TNFα Secretion (% of DMSO control) |
|---|---|---|---|---|
| MES 11461 | — | 28 | 31 | 44 |
| MES 10184 | Nle | 22 | 35 | |

The effects of Phe analogs of MES 11462 on TNFα secretion are summarized in Table 6. Based on their activity in one or both of the TNFα secretion assays, these analogs also decreased TNFα secretion. Three Leu analogs of MES 11462 (MES 10181, MES 10183, and MES 10185) also inhibited TNFα secretion (Table 7).

TABLE 6

Modifications of the Phe residue of MES 11462

| 10 μM | Modification | Luciferase 5B (% of DMSO control) | Luciferase 5B/3B (% of DMSO control 5B)/(% of DMSO control 3B) | TNFα Secretion (% of DMSO control) |
|---|---|---|---|---|
| MES 11462 | — | 24 | 37 | 55 |
| MES 10257 | 4-NO$_2$ Phe | 34 | 60 | — |
| MES 10258 | 4-Cl Phe | 43 | 39 | 42 |
| MES 10259 | 4-Ph Phe | 22 | 38 | 36 |
| MES 10261 | 2-Nal | 76 | 71 | 40 |
| MES 10262 | Tic | 47 | 47 | 68 |

TABLE 7
Modifications of the Leu residue of MES 11462

| 10 μM | Modification | Luciferase 5B (% of DMSO control) | Luciferase 5B/3B (% of DMSO control 5B)/(% of DMSO control 3B) | TNFα Secretion (% of DMSO control) |
|---|---|---|---|---|
| MES 11462 | — | 24 | 37 | 55 |
| MES 10181 | Chx | 17 | 49 | |
| MES 10183 | Val | 58 | 57 | |
| MES 10185 | Nle | 31 | 35 | 37 |

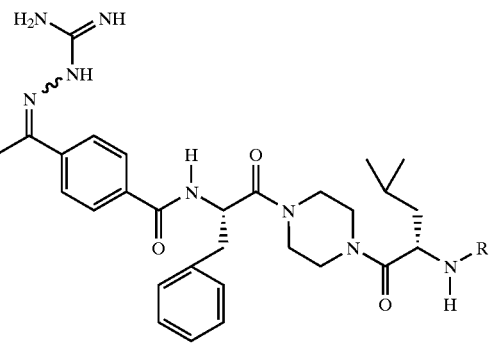

Analogs of MES 10170 Z-Mono Isomer 1

Monoguanylhydrazone Analogs

A series of analogs of the monoguanylhydrazone species compounds were generated by varying the uncharged aromatic end unit. Since MES 10170 was an inseparable mixture of the two Z-monoguanylhydrazones, the monoguanylhydrazone analogs of both species were prepared (Tables 8 and 9). Samples were prepared as unseparated E and Z geometric isomers. Two analogs (MES 10222 and MES 10231) were resynthesized and separated by HPLC. In the luciferase assay, each of the analogs decreased luciferase activity in the 5B cell line and had little effect on luciferase activity in the control 3B cell line. In addition, those analogs that were tested directly for inhibition of TNFα secretion also exhibited this inhibitory activity. In particular, the 4-iodobenzamide (MES 10226) had the greatest inhibitor activity in these assays.

TABLE 8
Modifications of MES 10170: Z-mono isomer 1

| 10 μM | GH | R | Luciferase 5B (% of DMSO control) | Luciferase 5B/3B (% of DMSO control 5R)/(% of DMSO control 3B) | TNFα Secretion (% of DMSO control) |
|---|---|---|---|---|---|
| MES 10170 | Z | 4-Bn Bn | 33 | 39 | 41 |
| MES 10222 | E/Z | Bn | 36 | 49 | 49 |
| MES 10249 | B | Bn | 58 | 68 | 40 |
| MES 10250 | Z | Bn | 37 | 49 | 40 |
| MES 10224 | E/Z | 4-NO$_2$ Bn | 36 | 37 | |
| MES 10226 | E/Z | 4-I Bn | 23 | 26 | |
| MES 10227 | E/Z | 4-Cl Bn | 34 | 39 | |
| MES 10228 | E/Z | 2-Naplithoyl | 38 | 40 | |

"Bn" denotes benzoyl

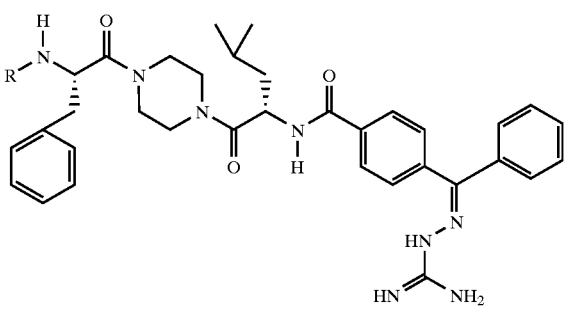

Analogs of MES 10170 Z-mono isomer 2

TABLE 9

Modifications of MES 10170: Z-mono isomer 2

| 10 μM | GH | R | Luciferase 5B (% of DMSO control) | Luciferase 5B/3B (% of DMSO control 5B)/(% DMSO control 3B) | TNFα Secretion (% of DMSO of control) |
|---|---|---|---|---|---|
| MES 10170 | Z | 4-Bn Bn | 33 | 39 | 41 |
| MES 10231 | E/Z | Bn | 34 | 33 | 49 |
| MES 10247 | E | Bn | 37 | 41 | 39 |
| MES 10248 | Z | Bn | 56 | 72 | 39 |
| MES 10233 | E/Z | 4-$NO_2$ Bn | 36 | 40 | 42 |
| MES 10234 | E/Z | 3-pyr-$CH_2CH_2CO$ | 60 | 58 | |
| MES 10235 | E/Z | $C_4H_3N_2CO$ | 70 | 75 | |

"Pyr" denotes pyridinyl;
"$C_4H_3N_2$" denotes pyrazine; and
"Bn" denotes benzoyl.

Similar studies as those described above were carried out on analogs of the monoguanylhydrazone MES 10173. In the luciferase assay, each of the analogs decreased the luciferase activity in the 5B cell line. In addition, all analogs shown below, except MES 10241, inhibited TNFα secretion in the direct assay of this activity.

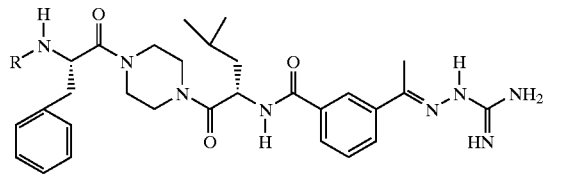

Analogs of MES 10173

TABLE 10

Modifications of MES 10173

| 10 μM | GH | R | Luciferase 5B (% of DMSO control) | Luciferase 5B/3B (% of DMSO control 5B)/(% of DMSO control 3B) | TNFα Secretion (% of DMSO control) |
|---|---|---|---|---|---|
| MES 10173 | E | 4-Bn Bn | 26 | 38 | 42 |
| MES 10241 | E | Bn | 68 | 90 | 100 |
| MES 10242 | E | 4-I Bn | 53 | 50 | 67 |
| MES 10243 | E | 4-$NO_2$ Bn | 81 | 79 | 73 |
| MES 10244 | E | 4-PhBn | 46 | 36 | 48 |
| MES 10306 | E | Ac | 85 | 125 | |
| MES 10307 | E | 4-BzlO-$C_6H_4CO$ | 38 | 40 | 45 |
| MES 10308 | E | 4-BnNH-$C_6H_4CO$ | 77 | 108 | |

Other Guanylhydrazones

Other guanylhydrazones were synthesized as described in Example 10 and assayed for TNFα secretion inhibitory activity (Table 11). These compounds have the general structure shown below in which X is either O or NN(H)C(NH)NH$_2$.

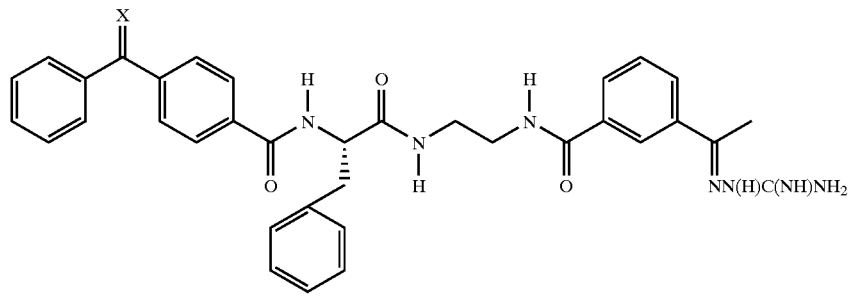

MES 10091-10093

TABLE 11

| | | Luciferase 5B/3B (% of DMSO control 5B)/(% of DMSO control 3B) | | | TNFα Secretion (% of DM80 control) | | |
|---|---|---|---|---|---|---|---|
| | GH | | | | | | |
| concentration of compound (μM) | | 1 μM | 3 μM | 10 μM | 1 μM | 3 μM | 10 μM |
| MES 10091 | E, E | 113 | 68 | 73 | 97 | 41 | 22 |
| MES 10092 | 1-Z, 4-B | 100 | 78 | 69 | 108 | 81 | 107 |
| MES 10093 | 4-B | | | 47 | | | |

N-phenyl-4-piperazinyl Succinate Derivatives

In addition to the guanylhydrazone compounds described above, compounds containing a N-phenyl-4-piperazinyl succinate (NPPS) unit were also synthesized and tested for inhibition of TNFα secretion (Table 12). These compounds were synthesized with either succinyl (denoted "S" in the "Linker" column and corresponding to n=2 in the structure below) or glutaryl linkers (denoted "G" in the "Linker" column and corresponding to n=3 in the structure below). Inhibition of TNFα was greatest in cells treated with analogs containing a large benzamide moiety as an end cap (e.g., 4-Bn-C$_6$H$_4$CO). This result is consistent with that observed for the other series of compounds described above.

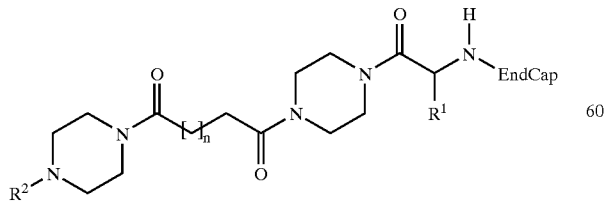

N-phenyl-4-piperazinyl Derivatives

TABLE 12

N-Phenyl-4-Piperazinyl Derivatives

| 10 μM | R¹ | Linker | R² | End Cap | Luciferase 5B (% of DMSO control) | Luciferase 5B/3B (% of DMSO control 5B)/ (% of DMSO control 3B) | TNFα Secretion (% of DMSO control) |
|---|---|---|---|---|---|---|---|
| MES 10229 | Ph | S | Ph | 4-Bn-C₆H₄CO | 31 | 49 | 65 |
| MES 10246 | Ph | G | Ph | 4-Bn-C₆H₄CO | 46 | 74 | |
| MES 10253 | Ph | S | Ph | 4-Ac-C₆H₄CO | 89 | 92 | |
| MES 10255 | Ph | S | Ph | 4-Ac-C₆H₄CO | 107 | 89 | |
| MES 10230 | CHMe₂ | S | Ph | 4-Bn-C₆H₄CO | 41 | 52 | 77 |
| MES 10245 | CHMe₂ | G | Ph | 4-Bn-C₆H₄CO | 38 | 57 | 66 |
| MES 10239 | CHMe₂ | S | Ph | 3-Ac-C₆H₄CO | 114 | 119 | 98 |
| MES 10304 | Me | S | Ph | 4-Bn-C₆H₄CO | 49 | 64 | |
| MES 10240 | (Boc) | S | Ph | H | 107 | 112 | 100 |
| MES 10301 | Ph | S | Me | 4-Bn-C₆H₄CO | 76 | 105 | |

EXAMPLE 4

General Synthetic Strategy for the Compounds of the Present Invention

The general strategy for the synthesis of the compounds of the present invention using commercially available starting materials is illustrated in Scheme 1.

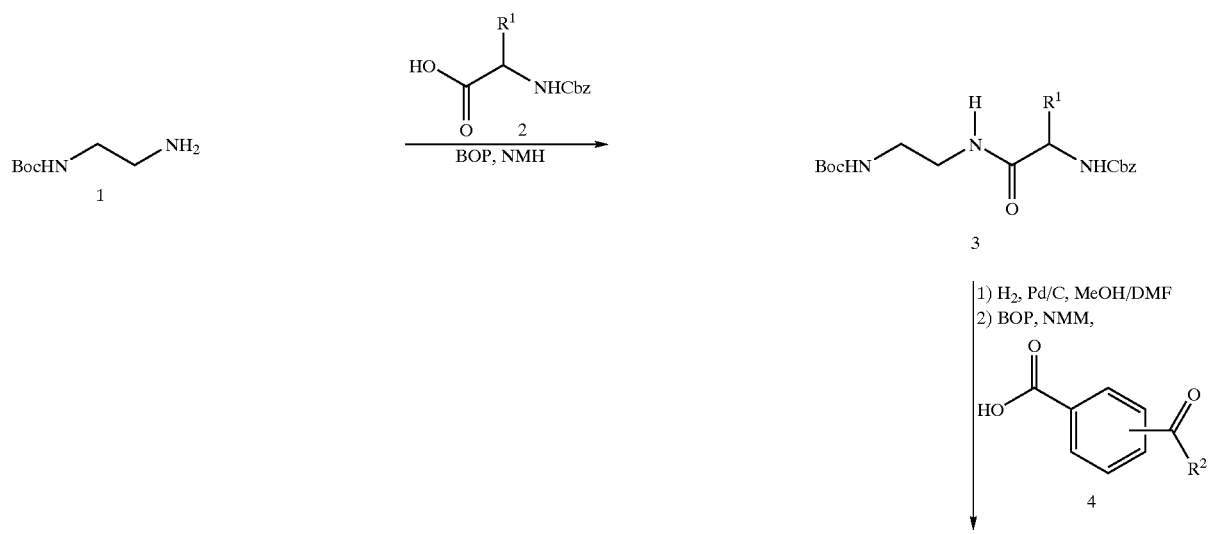

Scheme I

-continued

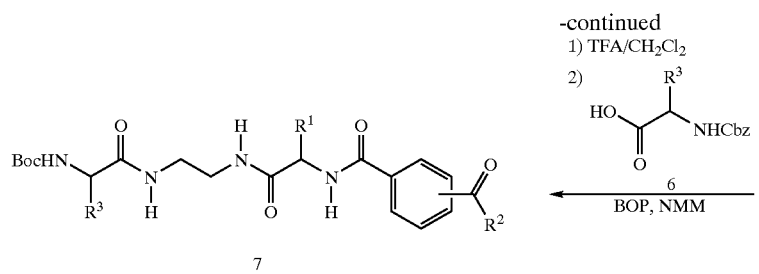

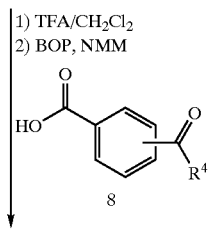

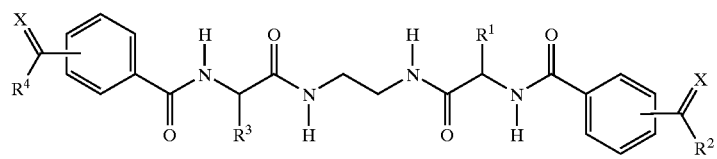

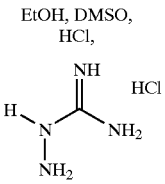

This synthetic method may be used to rapidly synthesize a variety of analogs by varying any of the $R^1$–$R^6$ groups or by using other linker-containing compounds (compound 1). For example, a variety of naturally-occurring and modified amino acids (compounds 2 and 6) may be either obtained from commercial sources (such as Sigma and Novabiochem) as protected amino acids or protected using standard chemical methods. In other embodiments, any of the $R^1$–$R^6$ groups may contain one of the suitable alkyl, aryl, or alkoxy groups described herein. Additionally, various benzoic acids (compounds 6 and 8) may be used in this method, such as those shown below.

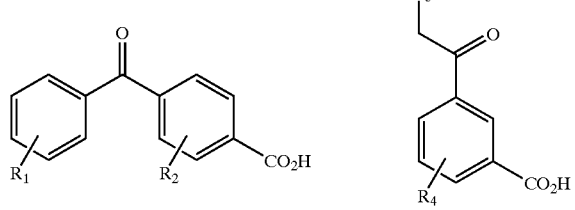

Acylbenzoic Acids

Examples of suitable $R_1$–$R^4$ groups for these acylbenzoic acids include alkyl groups, aryl groups, halogens, and —$OR_5$ groups in which $R_5$ is an alkyl group. Furthermore, other linkers may be incorporated into these compounds by using other diamines with the nitrogen atoms separated by additional hydrocarbon moieties (e.g., 3, 4,5, 6, 7, 8, or more carbons) or with fewer hydrocarbon moieties (i.e., 1 carbon). Alternatively, a piperazine linkage may be formed by using a piperazine containing compound, instead of the diamine compound 1 shown below. Moreover, if desired, one or more hydrogens in an amine group or hydrocarbon moiety of a linker may be substituted with a hydroxy, cyano, alkyl, aryl, alkoxy, thio, halo, nitro, or amino group. Additionally, one or more of the carbons in these linkers may be replaced with another atom, such as nitrogen, sulfur, or oxygen. Other variations can also be introduced into the mono and bisguanylhydrazones through the incorporation of substituted aminoguanidine moieties, such as those shown below.

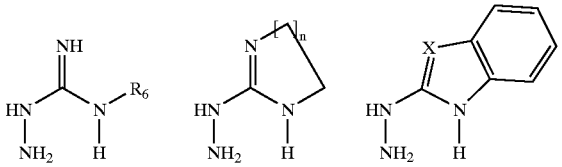

Aminoguanidine Moieties

Suitable $R_6$ groups include any alkyl or aryl group. In various embodiments, n is an integer between 1 and 10, inclusive. X is carbon, nitrogen, oxygen, or sulfur.

Each of the steps illustrated in Scheme I is described further below to illustrate this general synthetic strategy.

General Procedure for the Preparation of 1-Acyl-4-Boc-1,4-diazabutanes (compound 3)

Compound 1 [(t-Butoxycarbonyl)ethylenediamine] (10 mmol) was weighed directly into a flask. Z-protected aminoacid (compound 2) (10 mmol) was added directly to the amine in the flask. Under a nitrogen atmosphere, dry dimethylformamide (30 mL) was added to the flask using a syringe. Benzotriazole-1-yl-oxy-tris-(dimethylamino)-phosphonium hexafluorophosphate (BOP) (10 mmol, 4.43 g) was added to the solution in the flask. N-Methylmorpholine (20 mmol, 2.02 g, 2.20 mL) was added to the solution using a syringe, and the mixture was allowed to stir for 2–3 hours. The reaction mixture was quenched by the addition of 30 mL of water to the reaction flask, and the resultant mixture was partitioned between ethyl acetate (600 mL) and water (600 mL). The ethyl acetate layer was washed successively with saturated aqueous sodium bicarbonate (400 mL), water (4×600 mL), and brine (400 mL) and then dried over magnesium sulfate. Removal of the drying agent by filtration and evaporation of the organic phase to almost dryness (~20–30 mL) yielded a white solid precipitate. Hexanes (~30 mL) were added, and the mixture gently heated to reflux. Cooling to room temperature yielded the semicrystalline product as a white powder. The product was collected by filtration and dried under a stream of air.

General Procedure for the Preparation of 1-(N-Benzoyl-Acyl)-4-Boc-1,4-diazabutanes (Compound 5)

Compound 3 (1-Acyl-4-Boc-1,4-diazabutane) (2 mmol) was dissolved in dimethyl-formamide (6 mL) and methanol (6 mL) in a Parr hydrogenation flask. Trifluoroacetic acid (1.2 equivalents, 2.4 mmol) was added. The flask was flushed with a stream of nitrogen gas and palladium on carbon (5 mol % of 10% on carbon, 106 mg) was carefully added. The flask was refilled with hydrogen gas to 30 psi and allowed to agitate for 30 minutes. Complete hydrogenation was assayed by thin layer chromatography to ensure that no starting material remained.

The catalyst was removed by filtration through a short pad of celite, and the celite was washed with minimal amounts of methanol (1–2 mL). The methanol in the solution was removed under vacuum on a rotary evaporator. To the remaining DMF solution was added the desired benzoic acid (compound 4) (2 mmol), benzotriazole-1-yl-oxy-tris-(dimethylamino)-phosphonium hexafluorophosphate (BOP) (2 mmol, 886 mg), and N-methylmorpholine (3 equivalents, 6 mmol, 606 mg, 660 µL). The resulting solution was stirred overnight. The reaction was quenched by pouring into dilute aqueous sodium hydroxide (0.2 M, 120 mL). The resulting white solid was collected by filtration, and washed with water (2×20 mL). The remaining solid was partially air dried under a stream of air, and fully dried under high vacuum to yield a white powdery solid. If desired, this material may be crystallized from various ratios of ethylacetate/hexanes.

General Procedure for the Preparation of 1-(N-Benzoyl-Acyl)-4-(Acyl-Boc)-1,4-diazabutanes (compound 7)

Compound 5 [1-(N-Benzoyl-Acyl)-4-Boc-1,4-diazabutane] (0.5mmol) was dissolved in a 50/50 mixture of dichloromethane and trifluoroacetic acid (2 mL) and stirred for 30 minutes. Then, the volatile components were removed by rotary evaporation, and toluene (2 mL) was added to the flask. The volatile components were again removed, and the residue was further dried under high vacuum for 5 minutes. The oily residue was dissolved in dimethylformamide (1.5 mL). Benzotriazole-1-yl-oxy-tris-(dimethylamino)-phosphonium hexafluorophosphate (BOP) (1.0 equivalents, 220 mg), the desired N-Boc-protected aminoacid (compound 6) (1.0 equivalent), and N-methylmorpholine (3.0 equivalents, 202 mg, 220 µL) were added, and the resulting mixture was stirred overnight. The reaction mixture was poured into aqueous 0.2N NaOH (30 mL) and stirred for 30 minutes. The resulting white solid was collected by filtration, washed with water (2×5 mL), and dried to leave the desired product.

For compounds with moderate water/DMF solubility, two approaches were taken,. Initially enough NaCl was added to the sodium hydroxide solution to salt out the product, If this was unsuccessful the brine solution was extracted with ethyl acetate (30 mL). The organic phase was washed with 50/50 brine/water (3×30 mL) and dried over magnesium sulfate. Evaporation of the solvent left a foamy residue which was taken up into ethyl acetate (~1 mL) and precipitated from hot ethyl acetate with minimal hexanes (~2 mL). The resulting solid was allowed to precipitate overnight and then collected by filtration.

General Procedure for the Preparation of 1-(N-Benzoyl-Acyl)-4-(Acyl-N-Benzoyl)-1,4-diazabutanes (compound 9)

Compound 7 [1-(N-Benzoyl-Acyl)-4-(Acyl-Boc)-1,4-diazabutane] (0.1 mmol) was dissolved in a 50/50 mixture of dichloromethane and trifluoroacetic acid (1 mL) and stirred for 30 minutes. After which time the volatiles were removed on the rotary evaporator and toluene (2 mL) was added to the flask. The volatiles were again removed, and the residue was further dried under high vacuum for 5 min. The oily residue was dissolved in dimethylformamide (0.5 mL). Benzotriazole-1-yl-oxy-tris-(dimethylamino)-phosphonium hexafluorophosphate (BOP) (1.0 equivalent, 44 mg), the desired benzoic acid (compound 8) (1.0 equivalent), and N-methylmorpholine (4.0 equivalents, 40 mg, 44 µL) were added, and the resulting mixture was stirred overnight. The reaction mixture was poured into aqueous 0.2N NaOH (6 mL) and stirred for 30 minutes. The resulting white solid was collected by filtration, washed with water (2×2 mL). and dried to leave the desired product.

For compounds with moderate water/DMF solubility two approaches were taken. Initially enough NaCl was added to the sodium hydroxide solution to salt out the product, If this was unsuccessful, the brine solution was extracted with ethyl acetate (30 mL). The organic phase was washed with 50/50 brine/water (3×30 mL) and dried over magnesium sulfate. Evaporation of the solvent left a foamy residue which was taken up into ethyl acetate (~1 mL) and precipitated from hot ethyl acetate with minimal hexanes (~2 mL). The resulting solid was allowed to precipitate overnight and was then collected by filtration. Those samples that did not produce solids were evaporated to dryness, and used without further purification.

General Procedure for the Preparation of Bisguanylhydrazones of 1-(N-Benzoyl-Acyl)-4-(Acyl-N-Benzoyl)-1,4-diazabutanes (compound 10)

Compound 9 [1-(N-Benzoyl-Acyl)-4-(Acyl-N-Benzoyl)-1,4-diazabutane] (0.2 mmol) was dissolved in a mixture of DMSO (1 mL) and ethanol (672 µL). To this was added aminoguanidine hydrochloride (3 equivalents) and hydrochloric acid in ethanol (20 mol % of a 99:1 mixture of concentrated EtOH:HCl (~0.12M, 320 µL). The vial was sealed and heated to 110° C. for 5 days. After which time the ethanol was removed under vacuum. If desired, the samples can be stored as 0.2M DMSO solutions in a freezer at −5° C.

Addition of this DMSO solution to a stirred solution of sodium hydroxide (0.2 N) in water (10 mL) resulted in precipitation of a fine white solid, which was collected by filtration, washed with water (3×10 mL), and dried. Hydrochloric acid (0.1 N, 5 mL) in water (20 mL) was added, and the solution was stirred for 30 minutes. The guanylhydrazone solution was filtered and lyophilized to give a white powder. Guanylhydrazones derived from acetylbenzoylamides are formed predominantly(>20:1) in an E-conformation. Other substituted benzamides may form varying amounts of the Z-conformation in addition to the E-conformation. These isomeric forms can be separated by standard chromatographic techniques employing a reverse phase column such as a $C_{18}$-capped silica gel column. Additionally, the differential reactivity of the benzamides with aminoguanidines may be employed to prepare monoguanylhydrazone. These species may be efficiently purified by the same chromatographic techniques.

EXAMPLE 5

Synthesis of the Bisguanylhydrazone MES 10094

To further describe the synthesis of the compounds of the invention, the synthesis of the bisguanylhydrazone MES 10094 is illustrated in Scheme II, and each of the steps are described below.

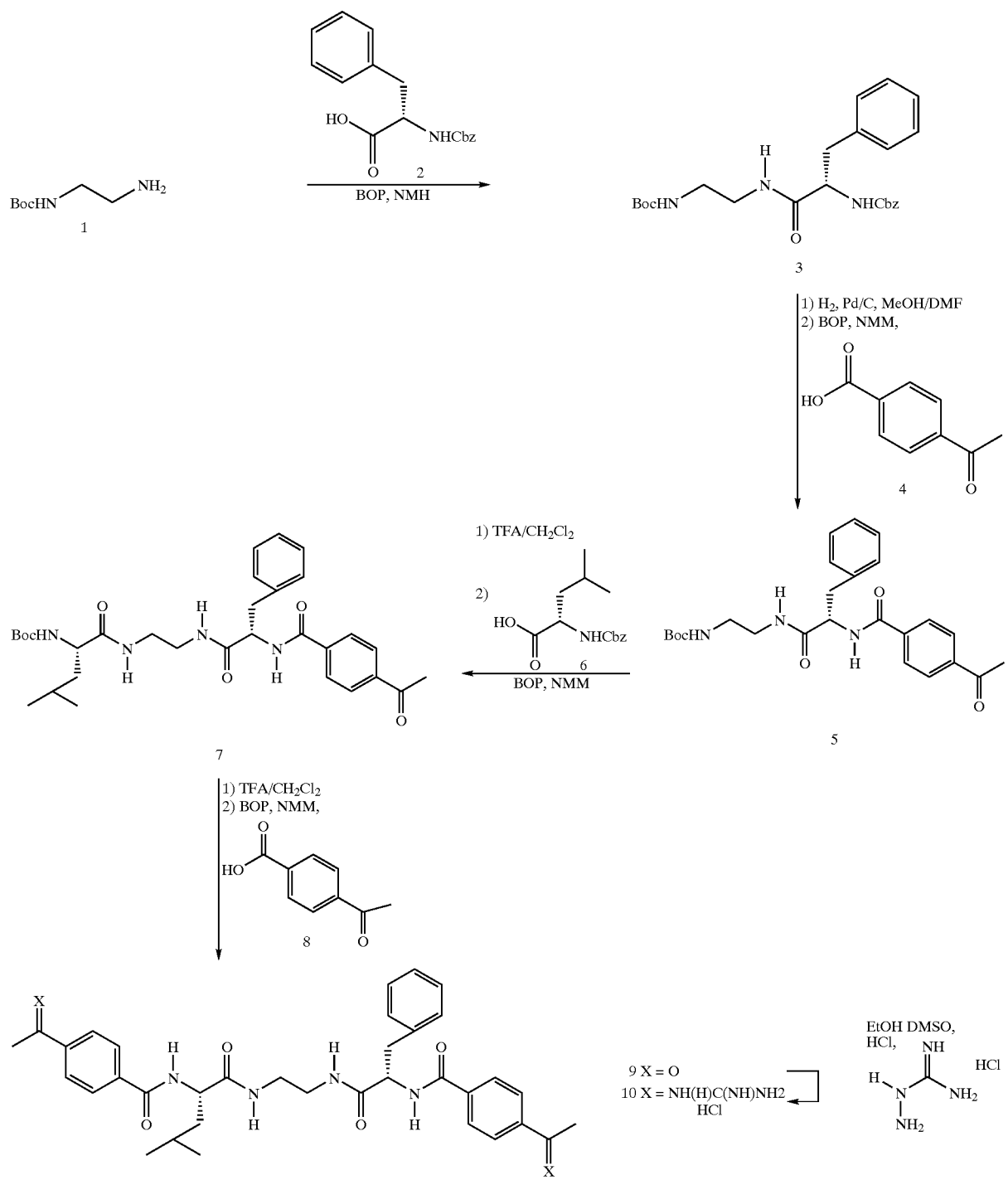

Scheme II

Synthesis of 1-[(S)-N-Cbz-2-Amino-3-phenylpropanoyl)-4-(t-butoxycarbonyl]-1,4-diazabutane (compound 3)

N-(t-Butoxycarbonyl)ethylenediamine (compound 1) (10 mmol) was weighed directly into a clean dry flask, which was then tightly sealed with a stopper. N-Cbz-(S)-Phenylalanine (compound 2) (10 mmol) was added directly to the amine in the flask. Under an inert atmosphere, dry dimethylformamide (30 mL) was added. Benzotriazole-1-yl-oxy-tris-(dimethylamino)-phosphonium hexafluorophosphate (10 mmol, 4.43 g) and then N-methylmorpholine (20 mmol, 2.02 g, 2.20 mL) were added to the solution, and the mixture was allowed to stir for 2–3 hours. The reaction mixture was quenched by the addition of 30 mL of water to the reaction flask, and partitioned between water (600 mL) and ethyl acetate (600 mL. The organic phase was washed successively with saturated sodium bicarbonate (400 mL), water (4×600 mL), and brine (400 mL) and then dried over magnesium sulfate. Filtering off the drying agent and concentration of the organic phase to ~20–30 mL yielded a white solid. Hexanes (~30 mL) were added and the mixture gently heated to reflux. Upon cooling, the semicrystalline product was precipitated as a white powder. This product was collected by filtration and dried.

Synthesis of 1-[(S)-N-(4-Acetylbenzoyl)-2-Amino-3-phenylpropanoyl]-4-(t-butoxycarbonyl)-1,4-diazabutane (compound 5)

Trifluoroacetic acid (1.2 equivalents, 2.4 mmol) was added to a solution of 1-[(S)—N-Cbz-2-Amino-3-phenylpropanoyl]-4-(t-butoxycarbonyl)-1,4-diazabutane (compound 3) (2mmol) in dimethylformamide (6 mL) and methanol (6 mL). Under a stream of nitrogen gas palladium on carbon (5 mol % of 10% on carbon, 106 mg) was carefully added. The reaction mixture was hydrogenated at 30 psi for ~30 minutes. Complete hydrogenation was assayed by thin layer chromatography to ensure that no starting material remains.

The catalyst was removed by filtration through a short pad of celite, and the celite was washed with minimal amounts of methanol (1–2 mL). The resultant solution was evaporated under reduced pressure to remove the methanol. To the remaining DMF solution was added 4-acetylbenzoic acid (compound 4) (2 mmol), benzotriazole-1-yl-oxy-tris-(dimethylamino)-phosphonium hexafluorophosphate (2 mmol, 886 mg) and N-methylmorpholine (3 equivalents, 6 mmol, 606 mg, 660 μL). The resulting solution was stirred overnight. The reaction was quenched by pouring into dilute aqueous sodium hydroxide (0.2 M, 120 mL). The resulting white solid was collected by filtration and washed with water (2×20 mL). The remaining solid was partially air dried under a stream of air, and fully dried under high vacuum to leave a white powdery solid.

Synthesis of 1-[(S)-N-(4-Acetylbenzoyl)-2-amino-3-phenylpropanoyl]-4-[(S)—N-(t-butoxycarbonyl)-2-amino-3-phenylpropanoyl]-1,4-diazabutane (compound 7)

Compound 5 [1-[(S)-N-(4-Acetylbenzoyl)-2-amino-3-phenylpropanoyl]-4-(t-butoxycarbonyl)-1,4-diazabutane] (0.5 mmol) was dissolved in a 50/50 mixture of dichloromethane and trifluoroacetic acid (2 mL) and stirred for 30 minutes. Then, the volatiles were removed on a rotary evaporator and toluene (2 mL) was added to the flask. The volatiles were again removed, and the residue was further dried under high vacuum for 5 minutes. The oily residue was dissolved in dimethylformamide (1.5 mL). Next, benzotriazole-1-yl-oxy-tris-(dimethylamino)-phosphonium hexafluorophosphate (1.0 equivalent, 220 mg) and N-(t-butoxycarbonyl)phenylalanine (compound 6) (1.0 equivalent), and N-methylmorpholine (3.0 equivalents, 202 mg, 220 μL) were added, and the resulting mixture was stirred overnight. The reaction mixture was poured into aqueous 0.2N NaOH (30 mL) and stirred for 30 minutes. The resulting white solid was collected by filtration, washed with water (2×5 mL), and dried to leave the desired product.

Synthesis of 1-[(S)—(N-(4-Acetylbenzoyl)-2-amino-3-phenylpropanoyl]-4-[(S)—(N-(4-acetylbenzoyl)-2-amino-3-phenylylpropanoyl]-1,4-diazabutane (compound 9)

Compound 7 [1-[(S)-N-(4-Acetylbenzoyl)-2-amino-3-phenylpropanoyl]-4-[(S)—(N-(t-butoxycarbonyl)-2-amino-3-phenylpropanoyl]-1,4-diazabutane] (0.1 mmol) was dissolved in a 50/50 mixture of dichloromethane and trifluoroacetic acid (1 μL) and stirred for 30 minutes. After which time the volatiles were removed on the rotary evaporator and toluene (2 mL) was added. The volatiles were again removed, and the residue was further dried under high vacuum for 5 min. The oily residue was dissolved in dimethylformamide (0.5 mL) and to this solution was added benzotriazole-1-yl-oxy-tris-(dimethylamino)-phosphonium hexafluoro-phosphate (1.0 equivalent, 44 mg) and 4-acetylbenzoic acid (compound 8) (1.0 equivalent), and N-methylmorpholine (4.0 equivalents, 40 mg, 44 L). The resulting mixture was stirred overnight, and then the reaction mixture was poured into aqueous 0.2N NaOH (6 mL) and stirred for 30 minutes. The resulting white solid was collected by filtration, washed with water (2×2 mL), and dried to leave the desired product.

Synthesis of Bisguanylhydrazones of 1-[(S)-N-(4-Acetylbenzoyl)-2-amino-3-phenylpropanoyl]-4-[(S)-N-(-4-acetylbenzoyl)-2-amino-3-phenylpropanoyl]-1,4-diazabutane (compound 10)

Compound 9 [1-[(S)-N-(4-Acetylbenzoyl)-2-amino-3-phenylpropanoyl)-4-[(S)-N-(4-acetylbenzoyl)-2-amino-3-phenylpropanoyl]-1,4-diazabutane] (0.2 mmol) was dissolved in a mixture of DMSO (1 mL) and ethanol (672 μL). Aminoguanidine hydrochloride (3 equivalents) and hydrochloric acid in ethanol (20 mol % of a 99:1 mixture of EtOH:HCl$_{(conc)}$ (~0.12 M), 320 μL) were added to this solution. The vial was sealed and heated to 110° C. for 5 days. Then, the ethanol was removed under vacuum. If desired, the samples can be stored as 0.2 M DMSO solutions in a freezer at −5° C.

Addition of this DMSO solution to a stirred solution of sodium hydroxide (0.2 N) in water (10 mL) resulted in precipitation of a fine white solid which was collected by filtration, washed with water (3×10 mL), and dried. Hydrochloric acid (0.1N, 5 mL) in water (20 mL) was added, and the solution was stirred for 30 minutes. The guanylhydrazone solution was filtered and lyophilized to give a white powder. The identity of the desired bisguanylhydrazone [(E,E)-Bisguanylhydrazone of 1-[(S)-N-(4-Acetylbenzoyl)-2-amino-3-phenylpro-panoyl]-4-[(S)-N-(4-acetylbenzoyl)-2-amino-3-phenylpropanoyl]-1,4-diaza-butane bis hydrochloride] was confirmed by mass spectrometry, $^1$H NMR, and $^{13}$C NMR.

M/S (FAB) [M+H]=759.

$^1$H NMR(DMSO) δ=2.34 (s, 6H), 3.0–3.25 (m, 8H), 4.65 (m, 2H), 7.1–7.4 (m, 10H), 7.8 (br s, 8H), 7.84 (d, 4H), 8.02 (d, 4H), 8.26 (bs s, 2H), 8.73 (d, 2H), 11.1 (s, 2H)ppm.

$^{13}$C NMR(DMSO) δ=14.3, 37.2, 38.2, 55.1, 126.1, 126.3, 127.3, 127.9, 129.1, 134.5, 138.4, 139.1, 150.7, 155.8, 165.5, 171.4 ppm.

EXAMPLE 6

Synthesis of MES 11461 (Mixture of Four Bisguanylhydrazones and Four Monoguanylhydrazones)

MES 11461 was prepared in a manner analogous to the above examples employing N-(t-butoxycarbonyl)piperazine (as compound 1), N-Cbz-(S)-Phenylalanine (as compound 2), 4-benzoylbenzoic acid (as compound 4), N-(t-butoxycarbonyl)leucine (as compound 6), and 4-benzoylbenzoic acid (as compound 8). The resulting crude guanylhydrazone product was a mixture of four bisguanylhydrazones and four monoguanylhydrazones which were separated by HPLC chromatography employing a reverse phase $C_{18}$-capped silica gel column and an eluent consisting of 30% (0.5% trifluoroacetic acid in water) and 70% acetonitrile. Results from $^1$H NMR analysis of three of these compounds is listed below.

MES 10164: (E,E)-Bisguanylhydrazone of 1-[(S)-N-(4-benzoylbenzoyl)-2-amino-3-phenylpropanoyl]-4-[(2S)-N-(4-benzoylbenzoyl)-2-amino-4-methylpentanoyl]-1,4-piperazine bis trifluoroacetate.

$^1$H NMR(DMSO) δ=0.89 (m, 6H), 1.48 (m, 1H), 1.69 (m, 2H), 3.0–3.9 (br m, 10H), 4.89 (m, 1H), 5.09 (m, 1H), 6.58 (br s, 4H), 7.1–7.52( m, 12H), 7.68 (m, 9H), 7.80 (d, 1H), 7.80 (br s, 4H), 7.89 (t, 1H), 8.70 (d, 1H), 8.90 (d, 1H), 9.80 (s, 2H)ppm.

MES 10165: (Z,Z)-Bisguanylhydrazone of 1-[(S)-N-(4-benzoylbenzoyl)-2-amino-3-phenylpropanoyl]-4-[(2S)-N-(4-benzoylbenzoyl)-2-amino-4-methylpentanoyl]-1,4-piperazine bis trifluoroacetate.

$^1$H NMR(DMSO) δ=0.89 (d, 6H), 1.48 (m, 1H), 1.69 (m, 2H), 3.05–3.80 (br m, 10H), 4.92 (m, 1H), 5.18,m, 1H), 6.56 (br s, 4H), 7.1–7.5 (br m, 12H), 7.6–7.76 (m, 9H, 7.78 (br s, 4H), 7.91 (t, 1H), 8.13 (d, 1H), 8.73 (br d, 1H), 9.01 (d, 1H), 9.48 (s, 1H), 9.80 (s, 1H)ppm.

MES 10168: (4-E)-Guanylhydrazone of 1-[(S)-N-(4-benzoylbenzoyl)-2-amino-3-phenylpropanoyl]-4-[(2S)-N-(4-benzoylbenzoyl)-2-amino-4-methylpentanoyl]-1,4-piperazine trifluoroacetate.

$^1$H NMR(DMSO) δ=0.90 (m, 6H), 1.49 (m, 1H), 1.69 (m, 2H), 3.06 (m, 2H), 3.20–3.70 (m, 8H), 4.92 (m, 1H), 5.12 (m, 1H), 7.1–7.4 (br m, 7H), 7.59 (t, 2H), 7.62–7.85 (br m, 12H), 7.90 (t, 1H), 7.98 (d, 1H), 8.72 (d, 1H), 9.08 (br t, 1H), 9.79 (s, 1H)ppm

EXAMPLE 7

Synthesis of MES 11462 (Mixture of Two Bisguanylhydrazones and One Monoguanylhydrazone)

MES 1142 was synthesized as described for the above examples. This particular example used N-(t-butoxycarbonyl)piperazine (as compound 1), N-Cbz-(S)-phenylalanine (as compound 2), 4-benzoylbenzoic acid phenylalanine (as compound 4), N-(t-butoxycarbonyl)leucine phenylalanine (as compound 6), and 3-acetylbenzoic acid phenylalanine (as compound 8). The resulting crude guanylhydrazone product was a mixture of two bisguanylhydrazones and one monoguanylhydrazone which were separated by HPLC chromatography employing a reverse phase $C_{18}$-capped silica gel column and an eluent consisting of 30% (0.5% trifluoroacetic acid in water) and 70% acetonitrile. The results of $^1$H NMR analysis of three of these compounds is listed below.

MES 10171: (E,E)-Bisguanylhydrazone of 1-[(S)-N-(4-benzoylbenzoyl)-2-amino-3-phenylpropanoyl]-4-[(2S)-N-(3-acetylbenzoyl)-2-amino-4-methylpentanoyl]-1,4-piperazine bis trifluoroacetate.

$^1$H NMR(DMSO) δ=0.92 (m, 6H), 1.50 (m, 1H), 1.72 (m, 2H), 2.36 (s, 3H), 3.06 (m, 2H), 3.10–3.70 (br m, 8H), 4.94 (m, 1H), 5.11 (m, 1H), 7.10–7.40 (br m, 9H), 7.56 (t, 1H), 7.62 (br s, 8H), 7.68 (m, 4H), 7.87 (d, 1H), 7.96 (t, 1H), 8.22 (t, 1H), 8.29 (m, 1H), 8.75 (d, 1H), 8.92 (d, 1H), 9.78 (s, 1H), 10.57 (s, 1H) ppm.

MES 10172: (1-Z,4-E)-Bisguanylhydrazone of 1-[(S)-N-(4-benzoylbenzoyl)-2-amino-3-phenylpropanoyl]-4-[(2S)-N-(3-acetylbenzoyl)-2-amino-4-methylpentanoyl]-piperazine bis trifluoroacetate.

$^1$H NMR(DMSO) δ=0.93 (d, 6H), 1.51 (m, 1H), 1.62 (m, 2H), 2.36 (s, 3H), 3.08 (m, 2H), 3.15–3.75 (br m, 8H), 4.96 (m, 1H), 5.19 (m, 1H), 7.10–7.90 (br m, 21H), 7.97 (m, 1H), 8.24 (d, 2H), 8.23 (br t, 1H), 8.30 (d, 1H), 8.78 (m, 1H), 9.01 (d, 1H), 9.70 (s, 1H) 10.62 (s, 1H)ppm.

MES 10173: (4-E)-Guanylhydrazone of 1-[(S)-N-(4-benzoylbenzoyl)-2-amino-3-phenylpropanoyl]-4-[(2S)-N-(3-acetylbenzoyl)-2-amino-4-methylpentanoyl]-piperazine trifluoroaceteate.

$^1$H NMR(DMSO) δ=0.91 9 m, 6H), 1.50 (m, 1H), 1.71 9 m, 2H), 2.37 (d, 3H), 3.08 (m, 2H), 3.20–3.78 (br m, 8H), 4.95 (m, 1H), 5.14 (m, 1H), 7.10–7.38 (m, 6H), 7.54 (t, 1H), 7.58 (t, 2H), 7.65–7.85 (m, 8H), 7.94–8.02 (m, 3H), 8.21 (t, 1H), 8.30 (br d, 1H), 8.75 (d, 1H), 9.08 (br t, 1H), 10.61 (d, 1H)ppm.

EXAMPLE 8

Synthesis of Analogs of Monoguanylhydrazone MES 10170

MES 10249 and 10250 were prepared in a manner analogous to the above examples employing N-(t-butoxycarbonyl)piperazine (as compound 1), N-Cbz-(S)-phenylalanine (as compound 2), 4-benzoylbenzoic acid (as compound 4), N-(t-butoxycarbonyl)leucine (as compound 6), and benzoic acid (as compound 8). The resulting crude guanylhydrazone product was a mixture of 2 monoguanylhydrazones which were separated by HPLC chromatography employing a reverse phase $C_{18}$-capped silica gel column and an eluent consisting of 30% (0.5% trifluoroacetic acid in water) and 70% acetonitrile. The $^1$H NMR spectra are described below.

MES 10249: (E)-Guanylhydrazone of 1-[(S)-N-(4-benzoylbenzoyl)-2-amino-3-phenylpropanoyl]-4-[(2S)-N-(benzoyl)-2-amino-4-methylpentanoyl]-1,4-piperazine trifluoroacetate.

$^1$H NMR(DMSO) δ=0.9 (m, 6H), 1.43 (m, 1H), 1.69 (m, 2H), 2.98–3.18 (m, 3H), 3.3–3.75(m, 7H), 4.90 (m, 1H), 5.10 (m, 1H), 7.1–7.4 (m, 11H), 7.68 (m, 4H), 7.70 (br, 4H), 7.80–7.94 (m, 4H), 8.61 (d, 1H), 8.91 (d, 1H), 9.80 (s, 1H)ppm.

MES 10250: (Z)-Guanylhydrazone of 1-[(S)-N-(4-benzoylbenzoyl)-2-amino-3-phenylpropanoyl]-4-[(2S)-N-(benzoyl)-2-amino-4-methylpentanoyl]-1,4-piperazine trifluoroacetate.

$^1$H NMR(DMSO) δ=0.9 (m, 6H), 1.48 (m, 1H), 1.70 (m, 2H), 3.0–3.78 (m, 10H), 4.92 (m, 1H), 5.19 (m, 1H), 7.14–7.56 (m, 13H), 7.6 (br, 4H), 7.62 (d, 2H), 7.89 (t, 2H), 8.12 (d, 2H), 8.64 (br t, 1H), 9.01 (d, 1H), 9.69 (s, 1H)ppm.

EXAMPLE 9

Synthesis of N-phenyl-4-piperazinyl Succinate Derivatives MES 10229 and 10230

For the synthesis of N-phenyl-4-piperazinyl succinate derivative MES 10229, (S)-1-N-(4-Benzylbenzoyl)-2-amino-3-phenylpropanoyl]-4-(t-butoxycarbonyl)-1,4-piperazine (54 mg, 0.1 mmol) was prepared as described above and treated with a 1:1 mixture of trifluoroacetic acid and methylene chloride (2 mL) for 45 minutes at room temperature. Then, the volatile components of the mixture were removed under reduced pressure. Toluene (2 mL) was added, and the volatile components were removed. To the resulting oily residue was added consecutively dimethylformamide (1 mL), (N-phenylpiperazine)succinamide 26 mg, 0.1 mmol), benzotriazole-1-yl-oxy-tris-(dimethylamino)-phosphonium hexafluoro-phosphate (44 mg, 0.1 mmol), and N-methylmorpholine (40 mg, 0.4 mmol). The mixture was stirred for 24 hours and then quenched with 0.2 N aqueous sodium hydroxide (12 mL). Stirring was continued for 3 hours, and then the precipitated solid was collected by filtration, washed with water (3×5 mL), and dried under vacuum to give the desired product (58 mg), 1-[(S)-N-(4-benzoylbenzoyl)-2-amino-3-phenylpropanoyl]-4[1-(4-(N-phenylpiperazine)succinyl]-1,4-piperazine.

$^1$H NMR(DMSO) δ=2.58 (m, 4H), 3.08 (m, 4H), 3.15 (m, 2H), 3.3–3.7 (m, 12H), 5.16 9(dd, 1H), 6.80 (t, 1H), 6.95 (d, 2H), 7.18–7.38 (m, 7H), 7.59 (t, 2H), 7.71 (t, 1H), 7.78 (m, 4H), 8.00 (d, 2H), 9.07 9t, 1H)ppm.

The synthesis of other N-phenyl-4-piperazinyl succinate derivatives was performed as described above for MES 10229. For example, MES 10230 [1-[(S)-N-(4- benzoylbenzoyl)-2-amino-4-methylpentanoyl]-4[1-(4-(N-phenylpiperazine)succinyl]-1,4-piperazine]was prepared by using (S)-1-N-(4-Benzylbenzoyl)-2-amino-4-methylpentanoyl]-4-(t-butoxycarbonyl)-1,4-piperazine as the starting compound.

$^1$H NMR(DMSO) δ=0.92 (d, 6H), 1.50 (m, 1H0, 1.72 (m, 2H), 2.60 (m, 4H), 3.09 (m, 2H), 3.17 (m, 2H), 3.3–3.7 (m, 12H), 4.99 (m, 1H), 6.80 (t, 1H), 6.96 (d, 2H), 7.22 (t, 2H), 7.59 (t, 2H), 7.71 (t, 1H), 7.72–7.85 (m, 4H), 8.06 (d, 2H), 8.89 (br d, 1H)ppm.

Additional NPPS derivatives may be prepared by using other linker-containing compounds such as those shown below.

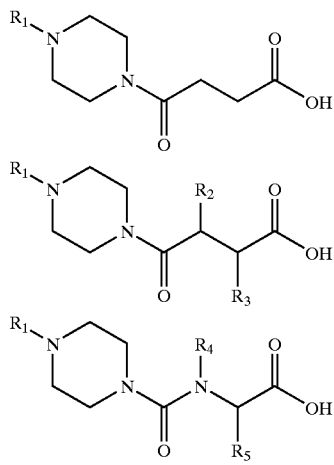

Linker-Containing Compounds

For these compounds, each of the $R_1$–$R_5$ groups may be an alkyl, cycloalkyl, aryl, or heteroaryl group, such as those listed herein.

EXAMPLE 10

Synthesis of Guanylhydrazones

Another group of guanylhydrazones were prepared in a manner analogous to the above examples employing N-(t-butoxycarbonyl)ethylenediamine, N-Cbz-(S)-phenylalanine, 4-benzoylbenzoic acid, and 3-acetylbenzoic acid. The resulting crude guanylhydrazone product was a mixture of two bisguanylhydrazones and one monoguanylhydrazone which were separated by HPLC chromatography employing a reverse phase $C_{18}$-capped silica gel column and an eluent consisting of 30% (0.5% trifluoroacetic acid in water) and 70% acetonitrile. These compounds have the general structure shown below in which X is either O or NN(H)C(NH)NH$_2$.

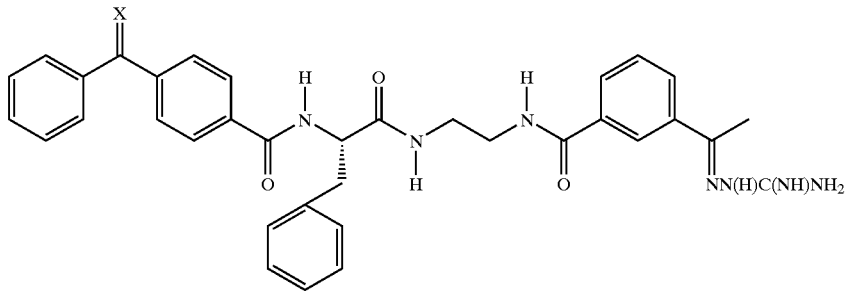

MES 10091: (E,E)-Bisguanylhydrazone of 1-[(S)-N-(4-benzoylbenzoyl)-2-amino-3-phenylpropanoyl]-4-(3-acetylbenzoyl)-1,4-diazabutane bis trifluoroacetate
M/S (FAB) [M+H]=674.
$^1$H NMR(DMSO) δ=2.33 (S, 3H), 2.96 (dd, 1H), 3.12 (dd, 1H), 3.25 (m, 1H), 3.33 (m, 3H), 4.65 (m, 1H), 7.15 (dt, 1H), 7.22 (t, 2H), 7.31 (m, 2H), 7.35 (m, 2H), 7.50 (t, 1H), 7.65 (d, 2H), 7.67 (m, 3H), 7.72 (br s, 4H), 7.78 (d, 2H), 7.87 (br d, 1H), 8.18 (br d, 1H), 8.26 (s, 1H), 8.33 (br t, 1H), 8.59 (br t, 1H), 8.68 (d, 1H), 9.78 (s, 1H), 10.61 (s, 1H)ppm.

MES 10092: (1-Z,4-E)-Bisguanylhydrazone of 1-[(S)-N-(4-benzoylbenzoyl)-2-amino-3-phenylpropanoyl]-4-(3-acetylbenzoyl)-1,4-diazabutane bis trifluoroacetate.
M/S (FAB) [M+H]=674.
$^1$H NMR(DMSO) δ=2.50 (s, 3H), 3.02 (dd, 1H), 3.15 (dd, 1H), 3.22–3.54 (m, 4H), 4,78 (m, 1H), 7.19 (t, 1H), 7.37 (t, 2H), 7.31–7.48 (m, 7H), 7.52 (t, 1H), 7.60 (d, 2H), 7,74 (br s, 4H), 7.90 (d, 1H), 8.09 (d, 2H), 8.19 (d, 1H), 8.26 (s, 1H), 8.37 (br t, 1H), 8.62 (br t, 1H), 8.79 9d, 1H), 9.68 (s, 1H), 10.69 (s, 1H)ppm.

MES 10093: (4-E)-Guanylhydrazone of 1-[(S)-N-(4-benzoylbenzoyl)-2-amino-3-phenylpropanoyl]-4-(3-acetylbenzoyl)-1,4-diazabutane trifluoroacetate.
M/S (FAB) [M+H]=618
$^1$H NMR(DMSO) δ=2.31 (s, 3H), 3.00 (dd, 1H), 3.16 (dd, 1H), 3.25–3.4-(m, 4H), 4.69 (m, 1H), 7.17 (dt, 1H), 7.26 (t, 2H), 7.33 (d, 2H), 7.50 (t, 1H), 7.57 (t, 2H), 7.66 (br s, 4H), 7.68–7.78 (m, 3H), 7.87 (d, 1H), 7.94 (d, 2H), 8.17 (d, 1H), 8.50 (s, 1H), 8.32 9br t, 1H), 8.58 (br t, 1H), 8.82 (d, 1H), 10.56 (s, 1H)ppm.

EXAMPLE 11

Treatment of Inflammation in Vivo

The compounds of the present invention can be assessed for their in vivo efficacy in treating inflammation. For example, a standard animal model of inflammation is utilized to directly test the efficacy of a candidate compound as an anti-inflammatory agent. Paw swelling induced by injection of the irritant carrageenan into murine footpads is a standard technique used to detect clinically useful anti-inflammatory compounds.

In one particular system, C3H/HeN mice are divided into two groups. One groups receives the vehicle of the candidate compound only through intraperitoneal injection, in each of its hindpaws (control 1), while the other group of mice receives the candidate compound and vehicle through intraperitoneal injection in each of its hindpaws. Paw edema is induced by injection of 50 microliters of 1% Lambda-carrageenan in HEPES 25 mM, pH 7.4, into the planter surface of the left hindpaw of each mouse (test paw, receiving candidate compound and carraggeenan; and control 2, receiving candidate compound vehicle and carraggeenan), while the right paw is injected with 50 microliters of HEPES alone (control 3). Three hours after paw injection, inflammation is measured by determining the thickness of each paw using a caliper. A candidate compound that decreases carraggeenan-induced paw inflammation more than the vehicle control may be useful in clinical applications for the treatment or prevention of inflammatory or other TNFα-mediated conditions.

EXAMPLE 12

Effect of Candidate Compounds on Fatal Endotoxic Shock

Candidate inhibitors of TNFα secretion may also be tested in vivo for their ability to prevent the lethal toxicity of lipopolysaccharide (LPS). In this system, a candidate compound or vehicle control is administered to BALB/c mice and 1.5 hours later LPS is intraperitoneally injected into the mice in an amount sufficient to induce lethality due to endotoxic shock in 50% of the control mice within 72 hours. The ability of a candidate compound to decrease the frequency of death indicates that the compound decreases TNFα secretion in vivo. Such compounds are useful in the treatment or prevention of fatal endotoxic shock and of other TNFα-mediated conditions.

Other Embodiments

From the foregoing description, it will be apparent that variations and modifications may be made to the invention described herein to adopt it to various usages and conditions.

All publications mentioned in this specification are herein incorporated by reference to the same extent as if each independent publication or patent application was specifically and individually indicated to be incorporated by reference.

What is claimed is:

1. A compound having one of the following formulas:

(1)

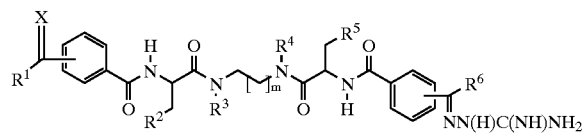

or a derivative or salt thereof, wherein
- $R^1$ and $R^6$ are independently selected from the group consisting of an alkyl and an aryl group;
- $R^2$ and $R^5$ are independently selected from the group consisting of hydrogen, an alkyl, and an aryl group;
- $R^3$ and $R^4$ are independently selected from the group consisting of hydrogen and an alkyl group;
- X is oxygen or $H_2N(HN)C(H)NN-$; and
- m is at least one;

(2)

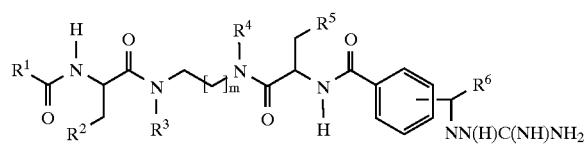

or a derivative or salt or salt thereof, wherein
- $R^1$ and $R^6$ are independently selected from the group consisting of an alkyl and an aryl group;
- $R^2$ and $R^5$ are independently selected from the group consisting of hydrogen, an alkyl, and an aryl group;

- $R^3$ and $R^4$ are independently selected from the group consisting of hydrogen and an alkyl; and
- m is at least one;

(5)

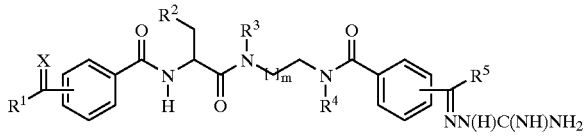

or a derivative or salt or salt thereof, wherein
- $R^1$ and $R^5$ are independently selected from the group consisting an aryl and an alkyl group;
- $R^2$ is hydrogen, an alkyl, or aryl group;
- $R^3$ and $R^4$ are independently selected from the group consisting of hydrogen and an alkyl group;
- X is oxygen or $H_2N(HN)C(H)NN-$; and
- m is at least one;

(6)

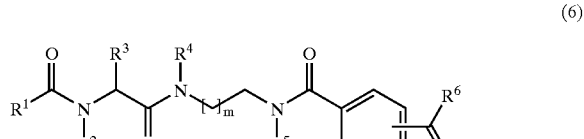

or a derivative or salt or salt thereof, wherein
- $R^1$ and $R^6$ are independently selected from the group consisting of an alkyl and an aryl group;
- $R^3$ is hydrogen, an alkyl, or an aryl group;

$R^2$, $R^4$, and $R^5$ are independently selected from the group consisting of hydrogen and an alkyl; and
m is at least one.
2. The compound of claim 1, wherein said compound is
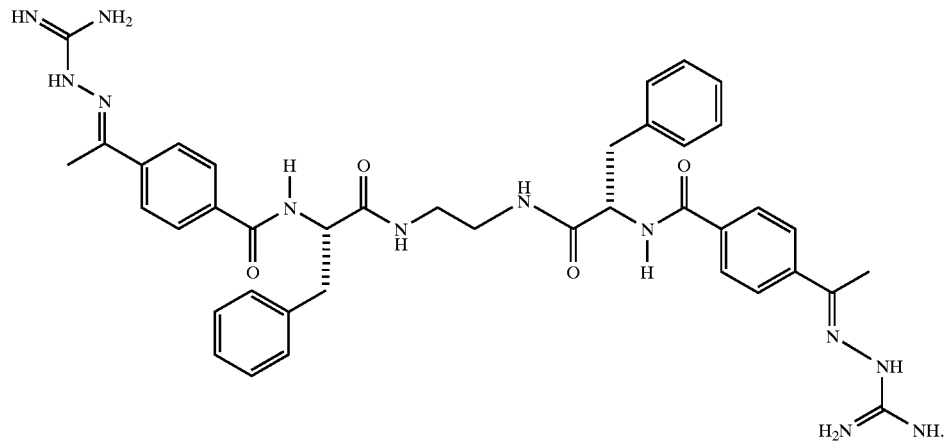
3. The compound of claim 1, wherein said compound is
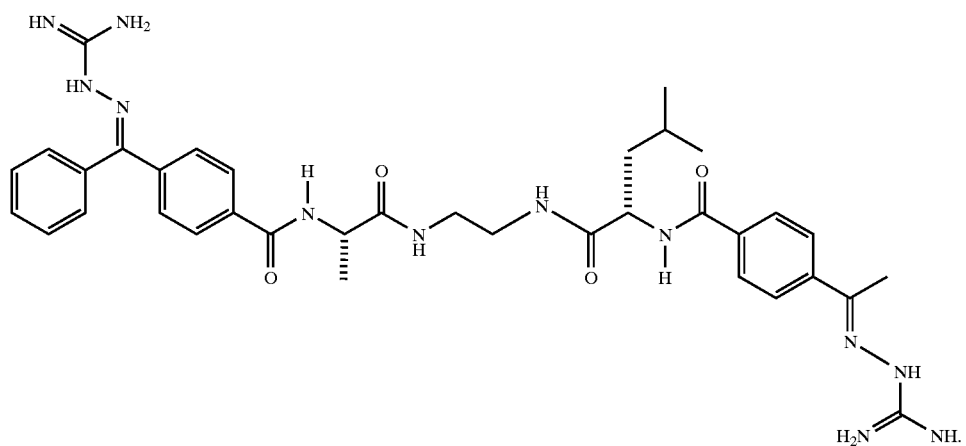
4. The compound of claim 1, wherein said compound is
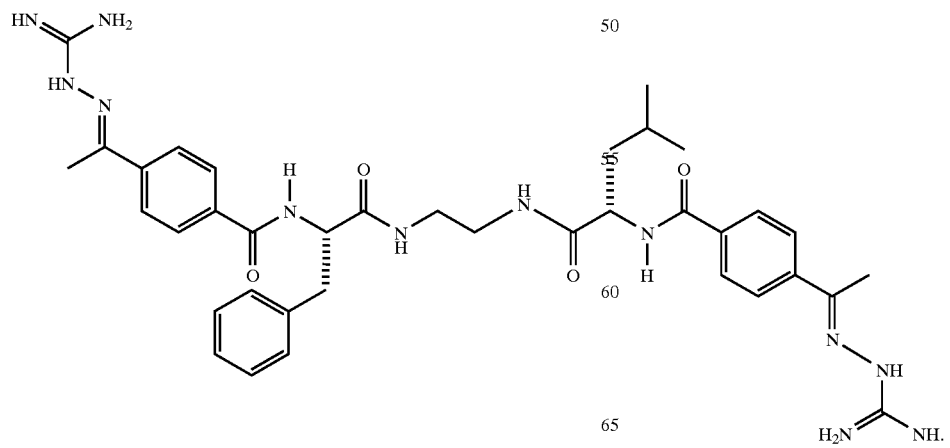

5. The compound of claim 1, wherein said compound is
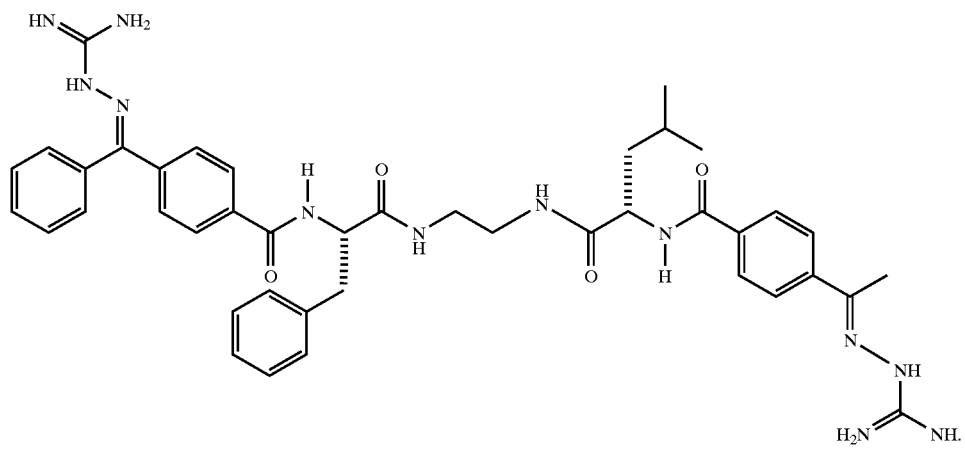
6. The compound of claim 1, wherein said compound is
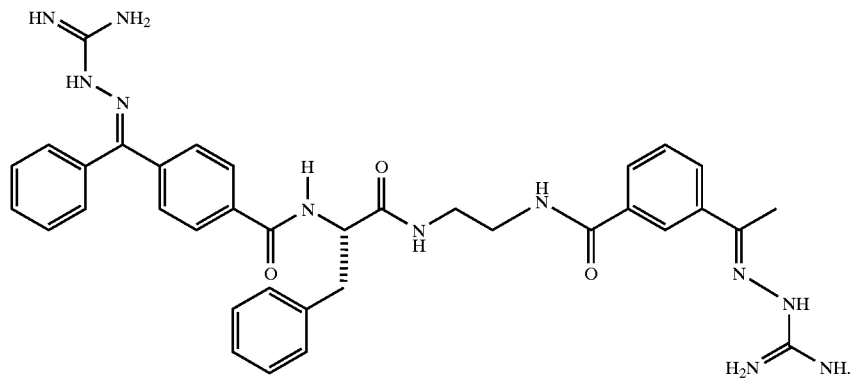
7. The compound of claim 1, wherein said compound is
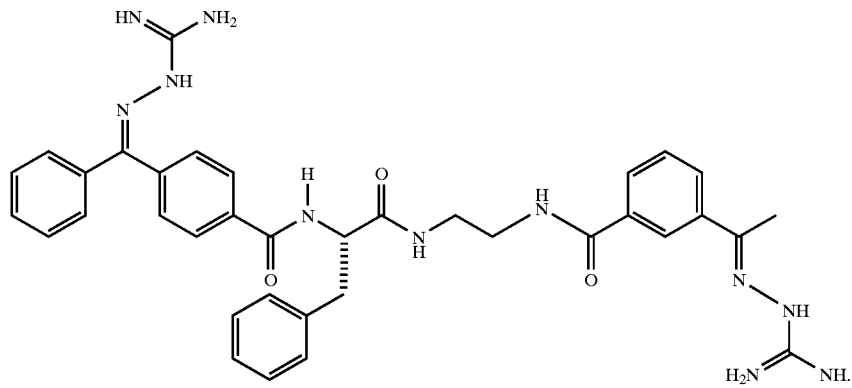

8. The compound of claim 1, wherein said compound is
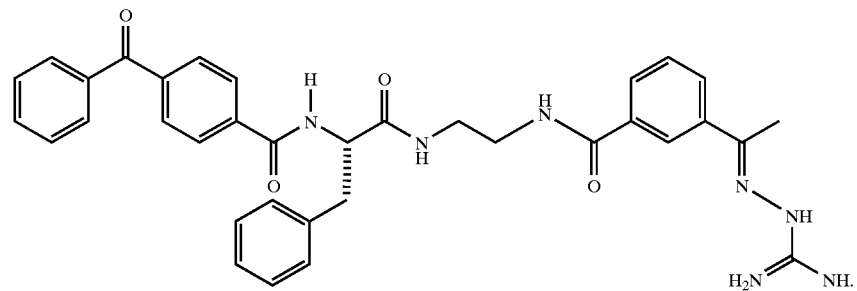

UNITED STATES PATENT AND TRADEMARK OFFICE
CERTIFICATE OF CORRECTION

| | | |
|---|---|---|
| PATENT NO. | : 6,872,850 B2 | |
| APPLICATION NO. | : 10/117955 | |
| DATED | : March 29, 2005 | |
| INVENTOR(S) | : Giordano et al. | |

It is certified that error appears in the above-identified patent and that said Letters Patent is hereby corrected as shown below:

Column 2, line 58, replace "$R^2$ or $R^6$" with -- $R^1$ or $R^6$--.

Column 4, line 30, after "4-methoxy-benzyl group" insert --,--.

Column 7, line 34, replace "al least" with --at least--.

Column 14, line 37, replace "using" with --used--.

Column 17, line 55, replace "be optionally may" with --may optionally be--.

Column 18,
　　Line 7, after "increased" insert --risk--; and
　　Line 15, after "topical" insert --,--.

Column 19, line 1, replace "assaying of a" with --assaying a--.

Column 21, line 30, replace "compounds" with --compound--.

Column 23, line 31, Table 2, 4$^{th}$ column, after " ( % of DMSO control" insert -- ) --.

Column 23, line 5, Figure of Bisguanylhydrazones of MES11461, replace

"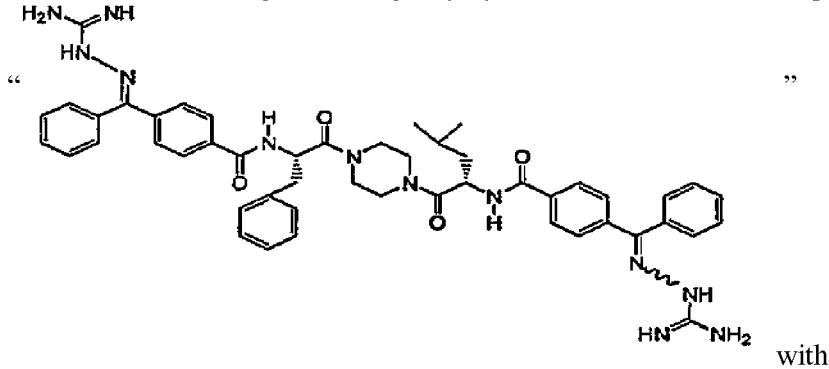"

with

--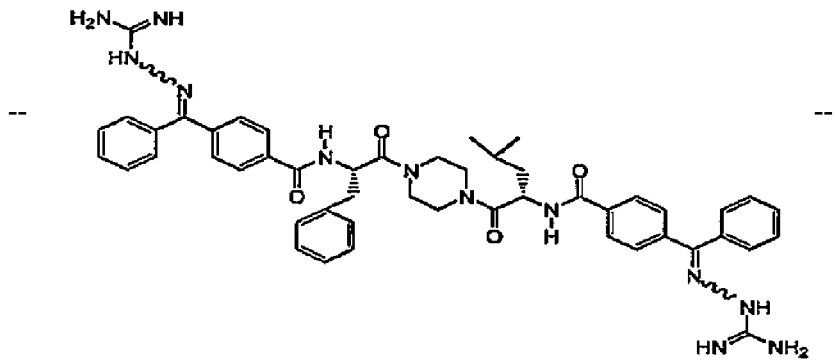--

UNITED STATES PATENT AND TRADEMARK OFFICE
CERTIFICATE OF CORRECTION

PATENT NO. : 6,872,850 B2
APPLICATION NO. : 10/117955
DATED : March 29, 2005
INVENTOR(S) : Giordano et al.

It is certified that error appears in the above-identified patent and that said Letters Patent is hereby corrected as shown below:

Column 28,
    Line 33, Table 8, 5th column, replace " ( % of DMSO control 5R"
       with -- ( % of DMSO control 5B--; and
    Line 38, Table 8, 2nd column, replace "B" with --E--.

Column 31,
    Line 33, Table 11, 4th column, replace " ( % of DM80 control) "
       with -- ( % of DMSO control) --;
    Line 38, Table 11, 2nd column, replace "4-B" with --4-E--; and
    Line 39, Table 11, 2nd column, replace "4-B" with --4-E--.

Column 33, line 53, Scheme I, replace "NMH" with --NMM--.

Column 35, line 55, replace "$R_1$-$R^4$" with --$R_1$-$R_4$--.

Column 37,
    Line 58, replace "taken, ." With --taken.--; and
    Line 59, replace "product," with --product.--.

Column 38,
    Line 17, replace " (2X2 mL) ." with -- (2X2 mL) --; and
    Line 21, replace "product," with --product.--.

Column 39, line 12, Scheme II, replace "NMH" with --NMM--.

Column 43,
    Line 8, replace "(m, 9H," with -- (m, 9H) , --; and
    Line 62, replace "9 m, 6H), 1.50 (m, 1H), 1.71 9" with --(m, 6H), 1.50 (m, 1H), 1.71)--.

Column 44,
    Line 62, replace "5.16 9 (dd, 1H)" with --5.16 (dd, 1H) --; and
    Line 64, replace "9.07 9t, 1H) " with --9.07 (t, 1H) --.

Column 45, line 22, replace "1.50 (m,1H0," with --1.50 (m,1H) , --.

Column 46,
    Line 35, replace "4,78" with --4.78-- ;
    Line 38, replace "8.79 9d, 1H)" with --8.79 (d, 1H)--; and
    Line 48, replace "8.32 9br t, 1H)" with --8.32 (br t, 1H) --.

UNITED STATES PATENT AND TRADEMARK OFFICE
CERTIFICATE OF CORRECTION

PATENT NO.        : 6,872,850 B2
APPLICATION NO. : 10/117955
DATED             : March 29, 2005
INVENTOR(S)      : Giordano et al.

Page 3 of 9

It is certified that error appears in the above-identified patent and that said Letters Patent is hereby corrected as shown below:

Column 49, line 63, replace "or salt or salt" with --or salt--.

Column 50,
  Line 46, replace "or salt or salt" with --or salt--; and
  Line 64, replace "or salt or salt" with --or salt--.

Column 51, Claim 2, replace

"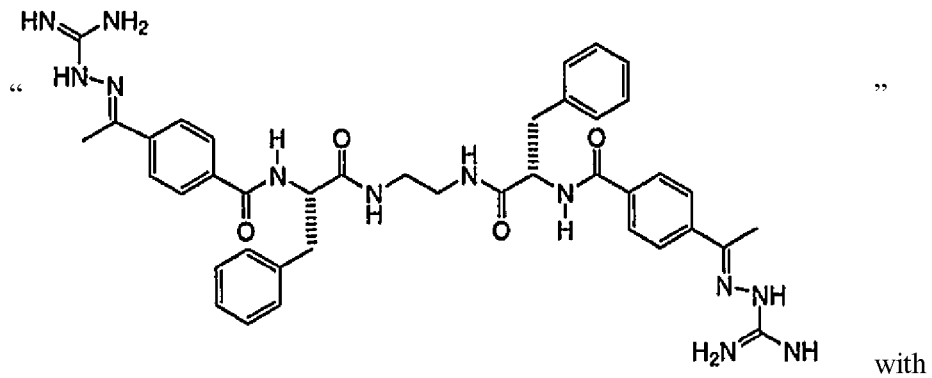" with

--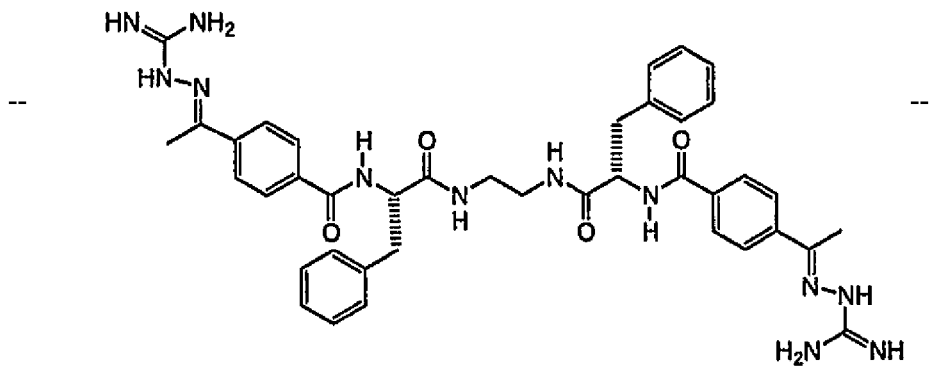--

UNITED STATES PATENT AND TRADEMARK OFFICE
CERTIFICATE OF CORRECTION

PATENT NO. : 6,872,850 B2
APPLICATION NO. : 10/117955
DATED : March 29, 2005
INVENTOR(S) : Giordano et al.

Page 4 of 9

It is certified that error appears in the above-identified patent and that said Letters Patent is hereby corrected as shown below:

Column 51, Claim 3, replace

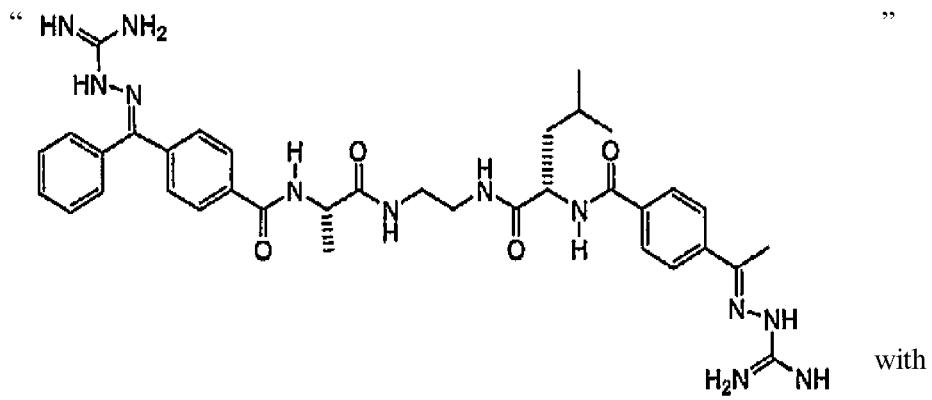

" " with

-- --

UNITED STATES PATENT AND TRADEMARK OFFICE
CERTIFICATE OF CORRECTION

PATENT NO.       : 6,872,850 B2                                    Page 5 of 9
APPLICATION NO.  : 10/117955
DATED            : March 29, 2005
INVENTOR(S)      : Giordano et al.

It is certified that error appears in the above-identified patent and that said Letters Patent is hereby corrected as shown below:

Column 51, Claim 4, replace

"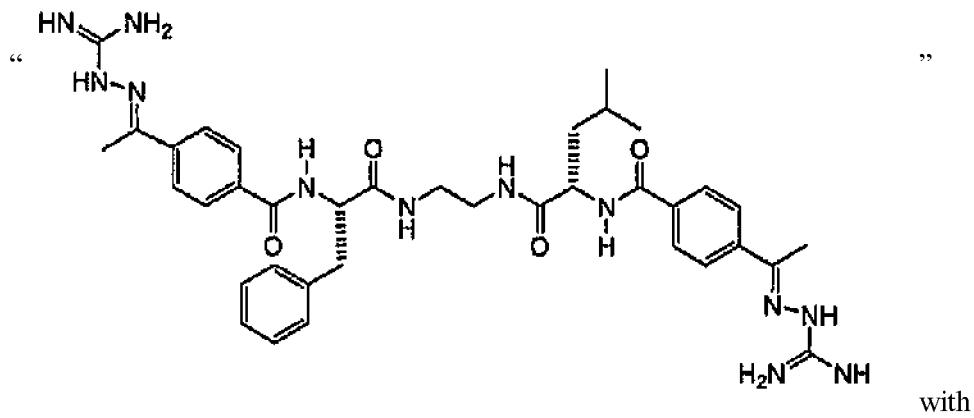"

with

--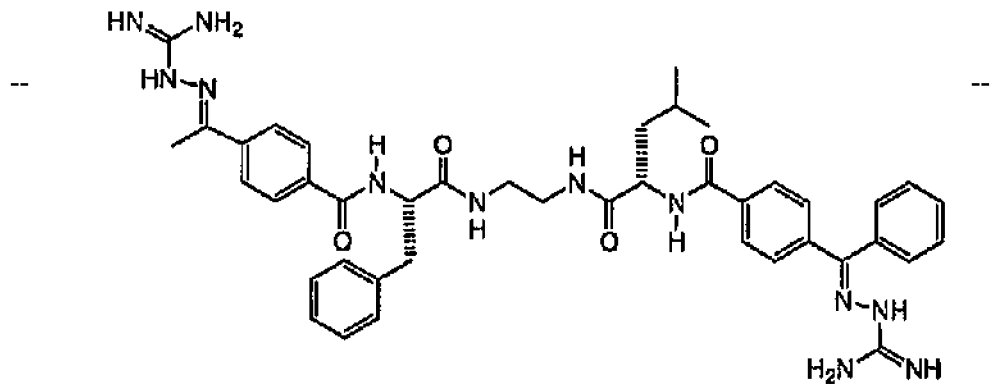--

UNITED STATES PATENT AND TRADEMARK OFFICE
CERTIFICATE OF CORRECTION

PATENT NO. : 6,872,850 B2  Page 6 of 9
APPLICATION NO. : 10/117955
DATED : March 29, 2005
INVENTOR(S) : Giordano et al.

It is certified that error appears in the above-identified patent and that said Letters Patent is hereby corrected as shown below:

Column 53, Claim 5, replace

"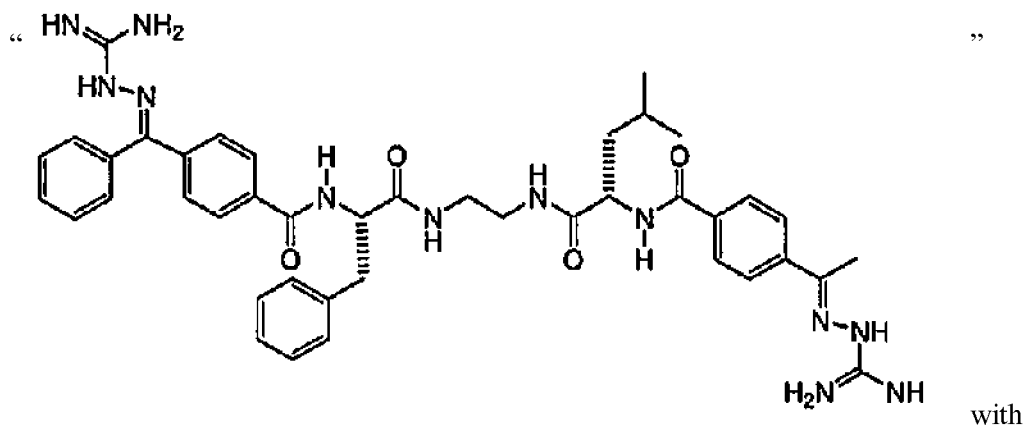"

with

--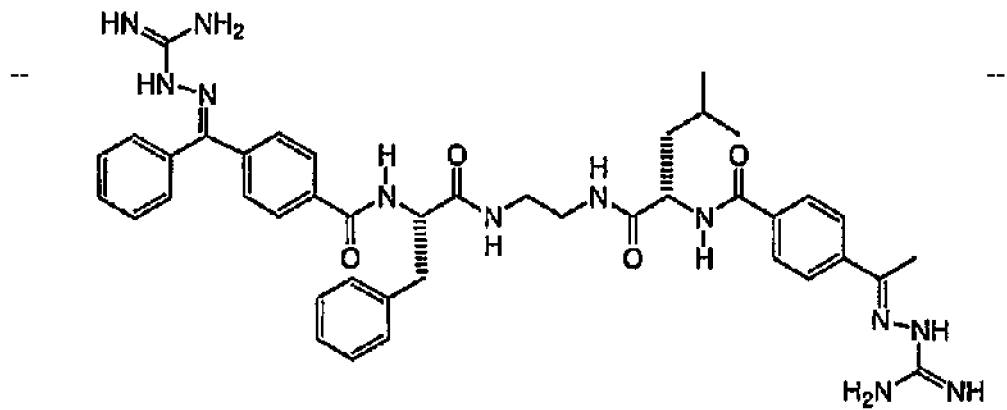--

UNITED STATES PATENT AND TRADEMARK OFFICE
CERTIFICATE OF CORRECTION

PATENT NO.        : 6,872,850 B2                                    Page 7 of 9
APPLICATION NO.   : 10/117955
DATED             : March 29, 2005
INVENTOR(S)       : Giordano et al.

It is certified that error appears in the above-identified patent and that said Letters Patent is hereby corrected as shown below:

Column 53, Claim 6, replace

"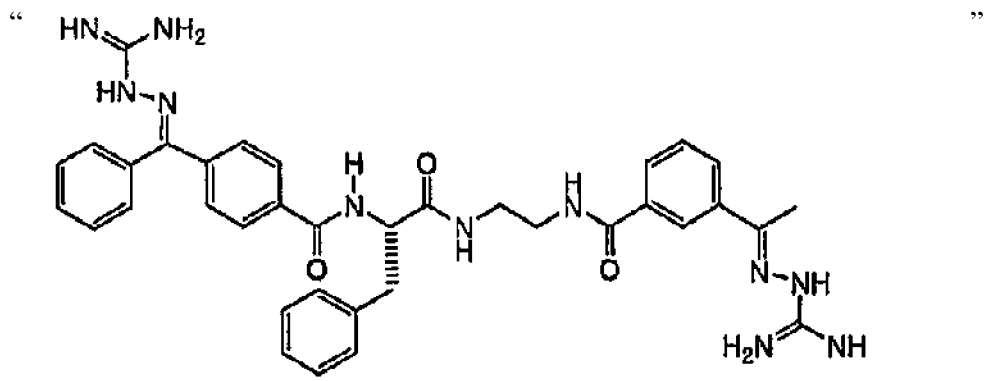" with

-- 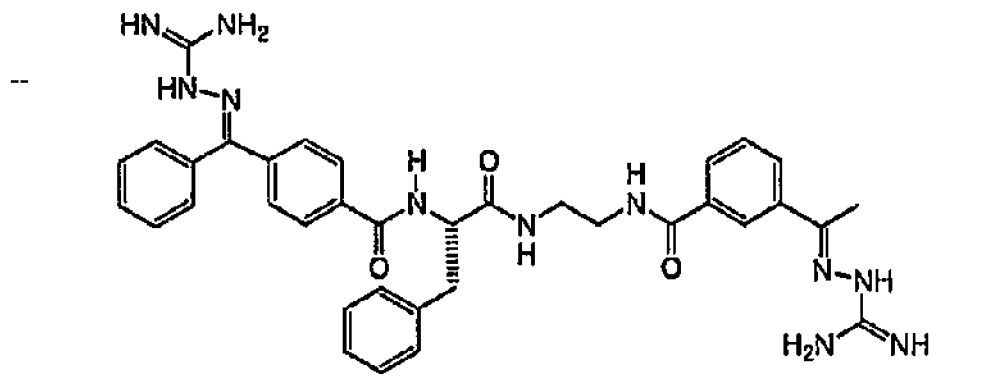 --

UNITED STATES PATENT AND TRADEMARK OFFICE
CERTIFICATE OF CORRECTION

PATENT NO. : 6,872,850 B2  Page 8 of 9
APPLICATION NO. : 10/117955
DATED : March 29, 2005
INVENTOR(S) : Giordano et al.

It is certified that error appears in the above-identified patent and that said Letters Patent is hereby corrected as shown below:

Column 53, Claim 7, replace

" 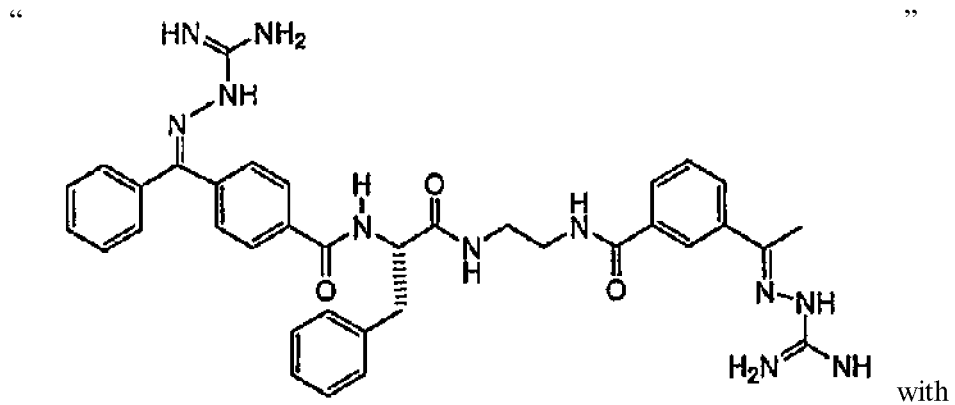 with

-- 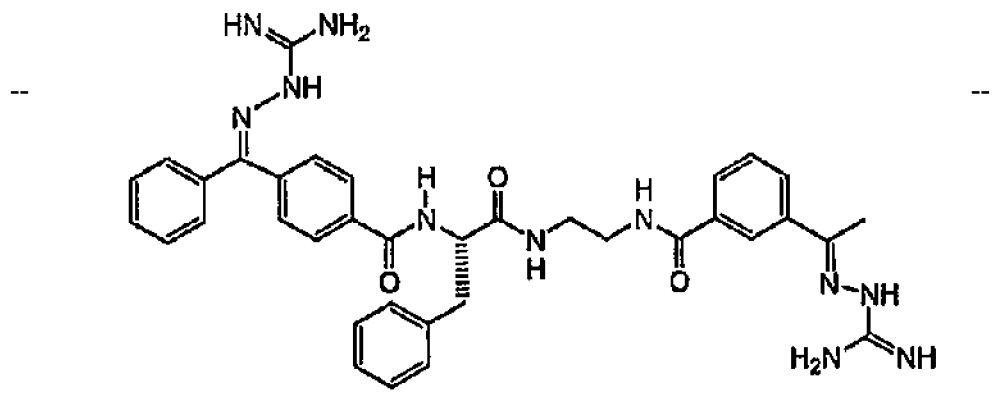 --

UNITED STATES PATENT AND TRADEMARK OFFICE
CERTIFICATE OF CORRECTION

PATENT NO. : 6,872,850 B2 Page 9 of 9
APPLICATION NO. : 10/117955
DATED : March 29, 2005
INVENTOR(S) : Giordano et al.

It is certified that error appears in the above-identified patent and that said Letters Patent is hereby corrected as shown below:

Column 55, Claim 8, replace

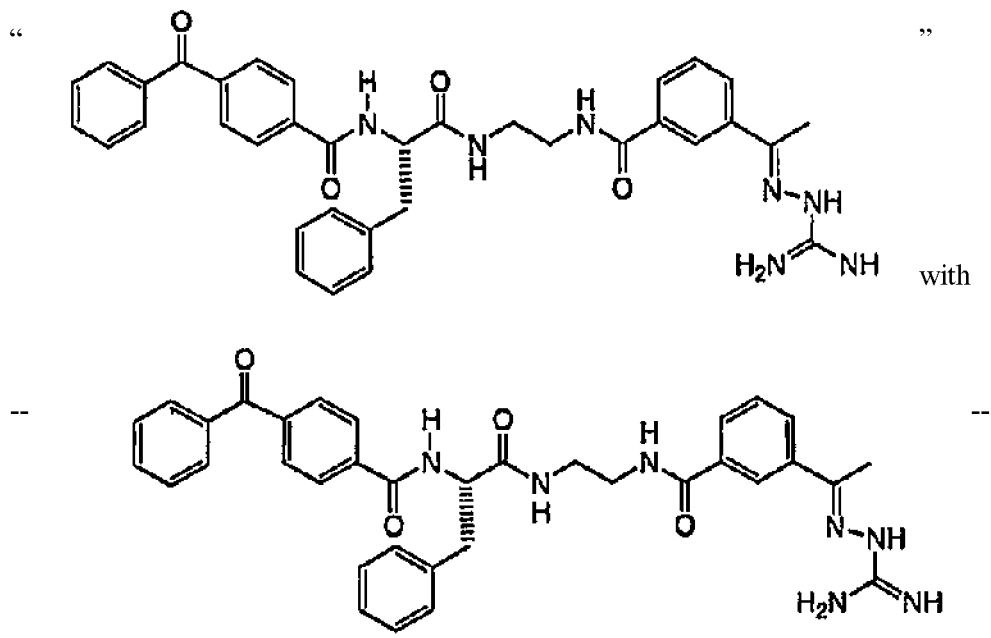

Signed and Sealed this

Third Day of July, 2007

JON W. DUDAS
*Director of the United States Patent and Trademark Office*